(12) United States Patent
Stapleton et al.

(10) Patent No.: US 10,233,490 B2
(45) Date of Patent: Mar. 19, 2019

(54) METHODS FOR ASSEMBLING AND READING NUCLEIC ACID SEQUENCES FROM MIXED POPULATIONS

(71) Applicant: METABIOTECH CORPORATION, Sunnyvale, CA (US)

(72) Inventors: James A. Stapleton, Eugene, OR (US); Timothy Whitehead, East Grand Rapids, MI (US)

(73) Assignee: Metabiotech Corporation, Sunnyvale, CA (US)

(*) Notice: Subject to any disclaimer, the term of this patent is extended or adjusted under 35 U.S.C. 154(b) by 475 days.

(21) Appl. No.: 14/947,988

(22) Filed: Nov. 20, 2015

(65) Prior Publication Data

US 2016/0152972 A1    Jun. 2, 2016

Related U.S. Application Data

(60) Provisional application No. 62/083,057, filed on Nov. 21, 2014.

(51) Int. Cl.
*C12Q 1/68* (2018.01)
*C12Q 1/6869* (2018.01)
*C12Q 1/6806* (2018.01)

(52) U.S. Cl.
CPC ......... *C12Q 1/6869* (2013.01); *C12Q 1/6806* (2013.01)

(58) Field of Classification Search
None
See application file for complete search history.

(56) References Cited

U.S. PATENT DOCUMENTS

| | | |
|---|---|---|
| 5,476,930 A | 12/1995 | Letsinger et al. |
| 5,780,613 A | 7/1998 | Letsinger et al. |
| 7,115,400 B1 | 10/2006 | Adessi et al. |
| 7,315,019 B2 | 1/2008 | Turner et al. |
| 7,582,420 B2 | 9/2009 | Oliphant et al. |
| 7,901,891 B2 | 3/2011 | Drmanac |
| 7,955,794 B2 | 6/2011 | Shen et al. |
| 8,003,354 B2 | 8/2011 | Shen et al. |
| 8,298,767 B2 | 10/2012 | Brenner et al. |
| 8,563,274 B2 | 10/2013 | Brenner et al. |
| 8,603,749 B2 | 12/2013 | Gillevet |
| 8,652,779 B2 | 2/2014 | Turner et al. |
| 8,653,779 B2 | 2/2014 | Yashiro et al. |
| 8,673,562 B2 | 3/2014 | Drmanac |
| 8,679,756 B1 | 3/2014 | Brenner et al. |
| 8,765,375 B2 | 7/2014 | Drmanac |

(Continued)

FOREIGN PATENT DOCUMENTS

| | | |
|---|---|---|
| AU | 2011274090 A1 | 2/2013 |
| EP | 2463386 A2 | 6/2012 |

(Continued)

OTHER PUBLICATIONS

Hayashi et al., Highly accurate genome sequences of *Escherichia coli* K-12 strains MG1655 W3110. Molecular systems biology, 2006.

(Continued)

*Primary Examiner* — Samuel C Woolwine
(74) *Attorney, Agent, or Firm* — Wilson Sonsini Goodrich & Rosati

(57) ABSTRACT

The disclosure relates to methods for obtaining nucleic acid sequence information by constructing a nucleic acid library and reconstructing longer nucleic acid sequences by assembling a series of shorter nucleic acid sequences.

30 Claims, 12 Drawing Sheets

Specification includes a Sequence Listing.

(56) References Cited

U.S. PATENT DOCUMENTS

| | | |
|---|---|---|
| 8,765,379 B2 | 7/2014 | Drmanac |
| 8,765,382 B2 | 7/2014 | Drmanac |
| 8,771,957 B2 | 7/2014 | Drmanac |
| 8,771,958 B2 | 7/2014 | Drmanac |
| 8,829,171 B2 | 9/2014 | Steemers et al. |
| 8,835,358 B2 | 9/2014 | Fodor et al. |
| 8,932,812 B2 | 1/2015 | Hogers et al. |
| 9,023,769 B2 | 5/2015 | Drmanac et al. |
| 9,034,580 B2 | 5/2015 | Cantor |
| 9,074,242 B2 | 7/2015 | Larson et al. |
| 9,085,798 B2 | 7/2015 | Chee |
| 9,102,980 B2 | 8/2015 | Brenner et al. |
| 9,127,307 B2 | 9/2015 | Adler, Jr. et al. |
| 9,150,852 B2 | 10/2015 | Samuels et al. |
| 9,260,753 B2 | 2/2016 | Xie et al. |
| 9,290,809 B2 | 3/2016 | Fodor et al. |
| 9,404,156 B2 | 8/2016 | Hicks et al. |
| 9,453,262 B2 | 9/2016 | Gillevet et al. |
| 9,476,095 B2 | 10/2016 | Vogelstein et al. |
| 9,514,272 B2 | 12/2016 | Kermani et al. |
| 9,524,369 B2 | 12/2016 | Drmanac et al. |
| 9,574,230 B2 | 2/2017 | Van Eijk et al. |
| 9,637,785 B2 | 5/2017 | Drmanac et al. |
| 2012/0190663 A1 | 7/2012 | Gornik et al. |
| 2013/0054151 A1 | 2/2013 | Kermani et al. |
| 2013/0224751 A1 | 8/2013 | Olson et al. |
| 2013/0237432 A1 | 9/2013 | Li et al. |
| 2014/0018246 A1 | 1/2014 | Drmanac et al. |
| 2014/0034497 A1 | 2/2014 | Davis et al. |
| 2014/0256568 A1 | 9/2014 | Link |
| 2015/0057163 A1 | 2/2015 | Rotem et al. |
| 2015/0057947 A1 | 2/2015 | Drmanac et al. |
| 2015/0087535 A1 | 3/2015 | Patel |
| 2015/0094961 A1 | 4/2015 | Kermani et al. |
| 2015/0148239 A1 | 5/2015 | Peter et al. |
| 2015/0259674 A1 | 9/2015 | Steelman et al. |
| 2016/0026758 A1 | 1/2016 | Jabara et al. |
| 2016/0040228 A1 | 2/2016 | De Wit et al. |
| 2016/0076023 A1 | 3/2016 | Quake et al. |

FOREIGN PATENT DOCUMENTS

| | | |
|---|---|---|
| EP | 2599877 A1 | 6/2013 |
| WO | WO-2004070005 A2 | 8/2004 |
| WO | WO-2007010252 A1 | 1/2007 |
| WO | WO-2008076406 A2 | 6/2008 |
| WO | WO-2011074960 A1 | 6/2011 |
| WO | WO-2012000445 A1 | 1/2012 |
| WO | WO-2012061832 A1 | 5/2012 |
| WO | WO-2014171898 A2 | 10/2014 |
| WO | WO-2015084802 A1 | 6/2015 |

OTHER PUBLICATIONS

Maniatis, et al. Molecular Cloning: A Laboratory Manual, Cold Spring Harbor, N.Y., pp. 280-281 (1982).

"Bankevich, et al. SPAdes: a new genome assembly algorithm and its applications to single-cell sequencing. J Comput Biol. May 2012;19(5):455-77. doi: 10.1089/cmb.2012.0021. Epub Apr. 16, 2012.".

"Scythe—A Bayesian adapter trimmer (version 0.994 BETA). Accessed online Jan. 20, 2016. https://github.com/vsbuffalo/scythe".

Dieffenbach, et al. PCR Primer: A Laboratory Manual, ed. Cold Spring Harbor Laboratory Press, 1995.

"FASTX-Toolkit. FASTQ/A short-reads pre-processing tools. Accessed online Jan. 20, 2016. http://hannonlab.cshl.edu/fastx_toolkit/".

"Shendure, et al. Accurate multiplex polony sequencing of an evolved bacterial genome. Science. Sep. 9, 2005;309(5741):1728-32. Epub Aug. 4, 2005.".

"Jiang, et al. Skewer: a fast and accurate adapter trimmer for next-generation sequencing paired-end reads. BMC Bioinformatics, 2014, 15:182, Published Jun. 12, 2014.".

"Margulies, et al. Genome sequencing in microfabricated high-density picolitre reactors. Nature. Sep. 15, 2005;437(7057):376-80. Epub Jul. 31, 2005.".

"Souza, et al. Long-term experimental evolution in *Escherichia coli*. V. Effects of recombination with immigrant genotypes on the rate of bacterial evolution. Journal of Evolutionary Biology. 1997;10:743-769.".

"Peng, et al. Generation of long insert pairs using a Cre-LoxP Inverse PCR approach. PLoS One. 2012;7(1):e29437. doi: 10.1371/journal.pone.0029437. Epub Jan. 9, 2012.".

"Rothberg, et al. An integrated semiconductor device enabling non-optical genome sequencing. Nature. Jul. 20, 2011;475(7356):348-52. doi: 10.1038/nature10242.".

"Rungpragayphan, et al. High-throughput, cloning-independent protein library construction by combining single-molecule DNA amplification with in vitro expression. J Mol Biol. Apr. 26, 2002;318(2):395-405.".

Sambrook et al., Molecular Cloning: A Laboratory Manual, 2nd edition, Cold Spring Harbor Laboratory Press (1989).

"Stapleton, et al. A cell-free microtiter plate screen for improved [FeFe] hydrogenases. PLoS One. May 10, 2010;5(5):e10554. doi: 10.1371/journal.pone.0010554.".

"Trimmomatic: A flexible read trimming tool for Illumina NGS data. USADELLA.org website. Accessed online Jan. 20, 2016. http://www.usadellab.org/cms/?page=trimmomatic".

"Zerbino, et al. Velvet Poster: de novo assembly using very short reads. European Bioinformatics Institute.".

SEQUENCE LISTING

```
<160> NUMBER OF SEQ ID NOS: 35

<210> SEQ ID NO 1
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (27)..(42)
<223> OTHER INFORMATION: a, c, t, g, unknown or other

<400> SEQUENCE: 1
nnncctacac gacgctcttc cgatctnnnn nnnnnnnnnn nnccaggaat agttatgtgc      60
attaatgaat ggcgcc                                                     76

<210> SEQ ID NO 2
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (27)..(42)
<223> OTHER INFORMATION: a, c, t, g, unknown or other

<400> SEQUENCE: 2
nnncctacac gacgctcttc cgatctnnnn nnnnnnnnnn nncc                      44

<210> SEQ ID NO 3
<211> LENGTH: 41
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(39)
<223> OTHER INFORMATION: a, c, t, g, unknown or other

<400> SEQUENCE: 3
cctacacgac gctcttccga tctnnnnnnn nnnnnnnnnc c                          41

<210> SEQ ID NO 4
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (27)..(42)
<223> OTHER INFORMATION: a, c, t, g, unknown or other
<220> FEATURE:
<221> NAME/KEY: modified_base
<222> LOCATION: (47)..(62)
<223> OTHER INFORMATION: a, c, t, g, unknown or other
<220> FEATURE:
<221> NAME/KEY: modified_base
<222> LOCATION: (86)..(88)
<223> OTHER INFORMATION: a, c, t, g, unknown or other

<400> SEQUENCE: 4
nnncctacac gacgctcttc cgatctnnnn nnnnnnnnnn nnccggnnnn nnnnnnnnnn      60
nnagatcgga agagcgtcgt gtaggnnn                                         88

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(16)
<223> OTHER INFORMATION: a, c, t, g, unknown or other
<220> FEATURE:
<221> NAME/KEY: modified_base
<222> LOCATION: (21)..(36)
<223> OTHER INFORMATION: a, c, t, g, unknown or other

<400> SEQUENCE: 5
nnnnnnnnnn nnnnnnccgg nnnnnnnnnn nnnnnn                                36

<210> SEQ ID NO 6
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (27)..(42)
<223> OTHER INFORMATION: a, c, t, g, unknown or other

<400> SEQUENCE: 6
nnncctacac gacgctcttc cgatctnnnn nnnnnnnnnn nnatcacgca ggaatagtta    60
tgtgcattaa tgaatggcgc c                                             81

<210> SEQ ID NO 7
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (27)..(42)
<223> OTHER INFORMATION: a, c, t, g, unknown or other

<400> SEQUENCE: 7
nnncctacac gacgctcttc cgatctnnnn nnnnnnnnnn nnatcacgc               49

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(39)
<223> OTHER INFORMATION: a, c, t, g, unknown or other

<400> SEQUENCE: 8
cctacacgac gctcttccga tctnnnnnnn nnnnnnnnna tcacgc                  46

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(16)
<223> OTHER INFORMATION: a, c, t, g, unknown or other

<400> SEQUENCE: 9
nnnnnnnnnn nnnnnnatca cgc                                           23

<210> SEQ ID NO 10
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (27)..(42)

<223> OTHER INFORMATION: a, c, t, g, unknown or other

<400> SEQUENCE: 10
nnncctacac gacgctcttc cgatctnnnn nnnnnnnnnn nnatcacgc          49

<210> SEQ ID NO 11
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (27)..(42)
<223> OTHER INFORMATION: a, c, t, g, unknown or other
<220> FEATURE:
<221> NAME/KEY: modified_base
<222> LOCATION: (57)..(72)
<223> OTHER INFORMATION: a, c, t, g, unknown or other
<220> FEATURE:
<221> NAME/KEY: modified_base
<222> LOCATION: (96)..(98)
<223> OTHER INFORMATION: a, c, t, g, unknown or other

<400> SEQUENCE: 11
nnncctacac gacgctcttc cgatctnnnn nnnnnnnnnn nnatcacgcg cgtgatnnnn     60
nnnnnnnnnn nnagatcgga agagcgtcgt gtaggnnn                            98

<210> SEQ ID NO 12
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(16)
<223> OTHER INFORMATION: a, c, t, g, unknown or other
<220> FEATURE:
<221> NAME/KEY: modified_base
<222> LOCATION: (31)..(46)
<223> OTHER INFORMATION: a, c, t, g, unknown or other

<400> SEQUENCE: 12
nnnnnnnnnn nnnnnnatca cgcgcgtgat nnnnnnnnnn nnnnnn              46

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cctacacgac gctcttccga tct                                      23

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aggaatagtt atgtgcatta atgaatgg                                              28

<210> SEQ ID NO 15
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' phosphate group
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (30)..(45)
<223> OTHER INFORMATION: a, c, t, g, unknown or other

<400> SEQUENCE: 15
nnngttcaga gttctacagt ccgacgatcn nnnnnnnnnn nnnnnccagg aatagttatg          60
tgcattaatg aatggccgc                                                       79

<210> SEQ ID NO 16
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' phosphate group
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (27)..(42)
<223> OTHER INFORMATION: a, c, t, g, unknown or other

<400> SEQUENCE: 16
nnncctacac gacgctcttc cgatctnnnn nnnnnnnnnn nnacaggaat agttatgtgc          60
attaatgaat ggccgc                                                          76

<210> SEQ ID NO 17
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' phosphate group
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (27)..(42)
<223> OTHER INFORMATION: a, c, t, g, unknown or other

<400> SEQUENCE: 17
nnncctacac gacgctcttc cgatctnnnn nnnnnnnnnn nnacaattcc tatcgttcac          60
gtcgtgtcgc catttagtgt ccagtctga                                            89

```
<210> SEQ ID NO 18
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' phosphate group
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (27)..(42)
<223> OTHER INFORMATION: a, c, t, g, unknown or other

<400> SEQUENCE: 18
nnncctacac gacgctcttc cgatctnnnn nnnnnnnnnn nnccaggaat agttatgtgc      60
attaatgaat ggcgcc                                                     76

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(9)
<223> OTHER INFORMATION: Internal deoxyuracil base
<220> FEATURE:
<221> NAME/KEY: modified_base
<222> LOCATION: (18)..(18)
<223> OTHER INFORMATION: Internal deoxyuracil base
<220> FEATURE:
<221> NAME/KEY: modified_base
<222> LOCATION: (28)..(28)
<223> OTHER INFORMATION: 3' deoxyuracil base
<220> FEATURE:
<221> NAME/KEY: misc_feature
<222> LOCATION: (29)..(30)
<223> OTHER INFORMATION: Phosphorothioate linkage

<400> SEQUENCE: 19
ccattcatua atgcacauaa ctattccugg                                      30

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(9)
<223> OTHER INFORMATION: Internal deoxyuracil base
<220> FEATURE:
<221> NAME/KEY: modified_base
<222> LOCATION: (18)..(18)
<223> OTHER INFORMATION: Internal deoxyuracil base
<220> FEATURE:
<221> NAME/KEY: modified_base
```

<222> LOCATION: (28)..(28)
<223> OTHER INFORMATION: Internal deoxyuracil base

<400> SEQUENCE: 20
ccattcatua atgcacauaa ctattccug                               29

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(9)
<223> OTHER INFORMATION: Internal deoxyuracil base
<220> FEATURE:
<221> NAME/KEY: modified_base
<222> LOCATION: (16)..(16)
<223> OTHER INFORMATION: Internal deoxyuracil base
<220> FEATURE:
<221> NAME/KEY: modified_base
<222> LOCATION: (23)..(23)
<223> OTHER INFORMATION: Internal deoxyuracil base
<220> FEATURE:
<221> NAME/KEY: misc_feature
<222> LOCATION: (24)..(25)
<223> OTHER INFORMATION: Phosphorothioate linkage

<400> SEQUENCE: 21
acacgacgug aacgauagga atugt                                   25

<210> SEQ ID NO 22
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (12)..(13)
<223> OTHER INFORMATION: Phosphorothioate linkage

<400> SEQUENCE: 22
ccgagaattc cat                                                13

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' phosphate group

<400> SEQUENCE: 23
tggaattctc gggtgccaag g                                       21

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
caagcagaag acggcatacg agat                                        24

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gtgactggag ttccttggca cccgagaatt cca                              33

<210> SEQ ID NO 26
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (57)..(58)
<223> OTHER INFORMATION: Phosphorothioate linkage

<400> SEQUENCE: 26
aatgatacgg cgaccaccga gatctacact ctttccctac acgacgctct tccgatct   58

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
acactctttc cctacacgac gctcttcc                                    28

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' phosphate group
<220> FEATURE:
<221> NAME/KEY: misc_feature
<222> LOCATION: (1)..(2)
<223> OTHER INFORMATION: Phosphorothioate linkage

<400> SEQUENCE: 28
atcggaagag cacacgtct                                              19

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (33)..(34)
<223> OTHER INFORMATION: Phosphorothioate linkage

<400> SEQUENCE: 29
gtgactggag ttcagacgtg tgctcttccg atct                              34

<210> SEQ ID NO 30
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aatgatacgg cgaccaccga gatctacacg ttcagagttc tacagtccga             50

<210> SEQ ID NO 31
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gtgactggag ttcagacgtg tgctcttccg atcccattca ttaatgcaca taactattcc  60

<210> SEQ ID NO 32
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (31)..(46)
<223> OTHER INFORMATION: a, c, t, g, unknown or other
<220> FEATURE:
<221> NAME/KEY: modified_base
<222> LOCATION: (104)..(104)
<223> OTHER INFORMATION: a, c, t, g, unknown or other

<400> SEQUENCE: 32
ccattcatta atgcacataa ctattcctgg nnnnnnnnnn nnnnnngatc gtcggactgt  60
agaactctga acttttttt tttttttttt tttttttttt ttvn                   104

<210> SEQ ID NO 33
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (35)..(50)
<223> OTHER INFORMATION: a, c, t, g, unknown or other
<220> FEATURE:
<221> NAME/KEY: modified_base
<222> LOCATION: (75)..(76)
<223> OTHER INFORMATION: Ribo-G
<220> FEATURE:
<221> NAME/KEY: modified_base
<222> LOCATION: (77)..(77)
<223> OTHER INFORMATION: Locked nucleic acid

<400> SEQUENCE: 33

```
gcggccattc attaatgcac ataactattc ctgtnnnnnn nnnnnnnnnn agatcggaag      60
agcgtcgtgt aggtggg                                                    77
```

<210> SEQ ID NO 34
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34

```
cgctcttccg atct                                                       14
```

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35

```
caggaatagt tatgtgcatt aatgaatggc gcc                                  33
```

METHODS FOR ASSEMBLING AND READING NUCLEIC ACID SEQUENCES FROM MIXED POPULATIONS

CROSS-REFERENCE

This application claims the benefit of U.S. Provisional Patent Application Ser. No. 62/083,057, filed Nov. 21, 2014, which is entirely incorporated herein by reference.

SEQUENCE LISTING

The instant application contains a Sequence Listing which has been submitted electronically in ASCII format and is hereby incorporated by reference in its entirety. Said ASCII copy, created on Feb. 4, 2016, is named 46679701201.txt and is 14,291 bytes in size.

STATEMENT OF GOVERNMENT INTEREST

This invention was made with government support under GM099291 awarded by the National Institutes of Health. The government has certain rights in the invention.

BACKGROUND

The transition from traditional Sanger-style sequencing methods to next-generation sequencing methods has lowered the cost of sequencing, yet significant limitations of next-generation sequencing methods remain. In one respect, available sequencing platforms generate sequencing reads that, while numerous, are relatively short and can require computational reassembly into full sequences of interest. Available assembly methods can be slow, laborious, expensive, computationally demanding, and/or unsuitable for populations of similar individuals (e.g., viruses). This is especially true for sequencing of complex genomes. Assembly is challenging, in part due to the ever-swelling sequencing datasets associated with assembly of short reads. Such datasets can place a large strain on computer clusters. For example, de novo assembly can require that sequencing reads (or k-mers derived from them) be stored in random access memory (RAM) simultaneously. For large datasets this requirement is not trivial. Moreover, even when assembly is possible, crucial haplotype information often cannot be recovered. Indeed, inherent limitations of available technologies obstruct improvements to overcoming the shortcomings of status quo sequencing technologies. Thus, there exists a need for improved sequencing methods and associated assembly techniques that reduce the time and/or computational requirements necessary to obtain accurate sequences.

SUMMARY

The disclosure provides a new method for obtaining nucleic acid sequence information. In various aspects, the method permits the sequencing of target nucleic acids by assembling intermediate and long nucleic acid sequences from short nucleic acid sequences. In various aspects, the method solves a problem associated with current nucleic acid sequencing methods, wherein important information about the origin of each short nucleic acid sequence is lost. In various aspects, the method is useful in haplotyping because it allows for identification and differentiation of mutations on the same or different chromosomes. In various aspects, the method is quicker and more accurate than other methods for obtaining nucleic acid sequence information.

In some aspects, the disclosure relates to methods for obtaining nucleic acid sequence information from a nucleic acid molecule by assembling a series of short nucleic acid sequences into longer nucleic acid sequences.

In one embodiment described herein is a method for obtaining nucleic acid sequence information from a nucleic acid molecule by assembling a series of nucleic acid sequences into a (i.e., one or more) longer nucleic acid sequence. In some aspects, the longer nucleic acid sequence or sequences are intermediate or long nucleic acid sequences. The methods described here allow subsets of the larger number of short reads collected during a sequencing run to be independently assembled into the full sequence of the intermediate-length molecule from which the "barcoded" group of short reads derived. These "sub-assembled" sequences are referred to as "synthetic long reads," because while like a true long read they represent the contiguous sequence of a particular individual nucleic acid molecule, they are synthesized from a collection of short reads that are grouped by a shared "barcode" sequence tag.

In one embodiment, the disclosure provides a method for obtaining nucleic acid sequence information from a nucleic acid molecule comprising a target nucleotide sequence by assembling a series of nucleic acid sequences into a (one or more) longer nucleic acid sequences, said method comprising: attaching a first adapter comprising an outer polymerase chain reaction (PCR) primer region, an inner sequencing primer region, and a central barcode region to each end of a plurality of linear nucleic acid molecules to form barcode-tagged molecules; replicating the barcode-tagged molecules to obtain a library of barcode-tagged nucleic acid molecules; breaking the barcode-tagged molecules, thereby generating linear, barcode-tagged fragments comprising the barcode region at one end and a region of unknown sequence at the other end; circularizing the linear, barcode-tagged fragments comprising the barcode region at one end and a region of unknown sequence from an interior portion of the target nucleotide sequence at the other end, thereby bringing the barcode region into proximity with the region of unknown sequence; fragmenting the circularized, barcode-tagged fragments into linear, barcode-tagged fragments; attaching a second adapter to each end of the linear, barcode-tagged fragments to form double adapter-ligated barcode-tagged nucleic acid fragments; replicating all or part of the double adapter-ligated barcode-tagged nucleic acid fragments; sequencing the double adapter-ligated barcode-tagged nucleic acid fragments; sorting a series of sequenced nucleic acid fragments into independent groups; and assembling each group of reads or short reads into a (one or more) longer nucleic acid sequence.

In some aspects, the method further comprises fragmenting a nucleic acid molecule into a plurality of shorter, linear nucleic acid sequences comprising target nucleotide sequences prior to attaching the first adapter. Such fragmenting is necessary, in some aspects, when the nucleic acid molecule is genomic DNA.

In some aspects of the method, the first adapter attached at the 5' end comprises a different barcode than the first adapter attached at the 3' end. In some aspects, the first adapter attached at the 5' end and the first adapter attached at the 3' end comprises the same barcode.

In some aspects of the method, the barcode-tagged sequences are replicated to obtain many copies of each barcode-tagged sequence. In some aspects, the replication is carried out using a primer complementary to the PCR primer region. In some aspects, the replication, or nucleic acid amplification, is carried out by any suitable nucleic acid amplification method. In various aspects, nucleic acid amplification methods include, but are not limited to, PCR, quantitative PCR, quantitative fluorescent PCR (QF-PCR), multiplex fluorescent PCR (MF-PCR), real time PCR (RT-PCR), single cell PCR, restriction fragment length polymorphism PCR (PCR-RFLP), PCK-RFLPIRT-PCR-IRFLP, hot start PCR, nested PCR, in situ polony PCR, in situ rolling circle amplification (RCA), bridge PCR, picotiter PCR, and emulsion PCR. Other suitable amplification methods include, but are not limited to, ligase chain reaction (LCR), transcription amplification, self-sustained sequence replication, selective amplification of target nucleic acids, consensus sequence primed polymerase chain reaction (CP-PCR), arbitrarily primed polymerase chain reaction (AP-PCR), degenerate oligonucleotide-primed PCR (DOP-PCR), and nucleic acid-based sequence amplification (NABSA). In particular aspects, the nucleic acid amplification is carried out by PCR.

In some aspects, the method further comprises of removing the PCR primer region from the barcode-tagged sequences. In some aspects, removing the PCR primer region is carried out before the circularizing the barcode-tagged fragments. In some aspects, removing the PCR primer region is carried out before breaking the barcode-tagged sequences at random locations. In some aspects, removing the PCR primer region is carried out after breaking the barcode-tagged sequences at random locations.

In some aspects of the method, breaking the barcode-tagged sequences is carried out by an enzyme. In some aspects, the breaking is carried out at random locations on the nucleic acid sequences.

In some aspects, the second adapter comprises, consists essentially of, or consists of two annealed nucleic acid strands of different lengths, wherein the strand attached at the 5' ends of a linear, barcode-tagged fragment is of a different length than the strand attached at the 3' ends of a linear, barcode-tagged fragment, wherein one end of the second adapter is double stranded to facilitate ligation and the other end of the second adapter comprises a 3' single-stranded overhang, and wherein only the longer of the two oligonucleotides comprises a sequence complementary to a second sequencing primer and comprises sufficient length to allow annealing of that primer.

In some aspects, replicating the double adapter-ligated barcode-tagged nucleic acid fragments is carried out using two primers, the first of which is complementary to a constant sequence from the barcode-containing adapter, and the second of which is complementary to the overhanging sequence of the asymmetric adapter, and which together add sequences necessary for nucleic acid sequencing.

In some aspects, sequencing the double adapter-ligated barcode-tagged nucleic acid fragments is carried out beginning with the barcode region followed by the target sequence.

In some aspects of the method, sorting the series of sequenced nucleic acid fragments into independent groups is based on shared barcodes.

In some aspects, assembling each group is carried out independent of all other groups.

In various aspects, the method further comprises a (one or more) selecting the plurality of linear nucleic acid sequences on the basis of size. In some aspects, this selecting by size is carried out prior to attaching the first adapter or after attaching the first adapter but prior to nucleic acid amplification. In some aspects, selecting the fragments on the basis of size is carried out prior to sequencing.

In some aspects, the enzyme or enzyme mixture that breaks the linear, tagged nucleic acid fragments is double-stranded DNA fragmentase. In some aspects, the enzyme or enzyme mixture that breaks the linear, tagged nucleic acid fragments is KAPA Frag Enzyme. In some aspects, the enzyme or enzyme mixture that breaks the linear, tagged nucleic acid fragments is a transposase.

In various aspects of the method, the PCR primer region is removed from the tagged, amplified nucleic acid fragments. In some aspects, the PCR primer region is removed by an enzyme or enzyme mixture that excises uracils and breaks the phosphate backbone. In some aspects, the PCR primer comprises methylated nucleotides and the PCR primer region is removed by restriction enzymes specific for methylated sequences. In some aspects, all or part of the PCR primer comprises RNA and the primer region is removed by enzymes specific for RNA.

In some aspects, nucleic acid sequence information is obtained for a longer nucleic acid sequence comprising a length of at least about 500 bases. In some aspects, nucleic acid sequence information is obtained for an intermediate or a long nucleic acid sequence. In some aspects, nucleic acid sequence information is obtained for a nucleic acid sequence comprising a length of at least about 1000 bases. In some aspects, nucleic acid sequence information is obtained for a nucleic acid sequence comprising a length of at least 1000 or more bases. In some aspects, nucleic acid sequence information is obtained for a nucleic acid sequence comprising a length from about 1 kilobase to about 20 kilobases. In some aspects, nucleic acid sequence information is obtained for a nucleic acid sequence comprising a length of up to about 12 kilobases.

In some aspects, the nucleic acid sequence information comprises greater than about 95% fidelity to the target nucleotide sequence.

In some aspects, the target nucleotide sequence originates from genomic DNA. In some aspects, the target nucleotide sequence is a non-genomic nucleic acid.

In some aspects, the nucleic acid sequence information is obtained in less than three days.

In some aspects, the method is carried out in a single tube. In some aspects, samples for barcode pairing are prepared in parallel in a second tube.

An additional aspect of the disclosure provides a method for sequencing a nucleic acid molecule. The method includes: (a) providing a plurality of clonal nucleic acid molecules each having the same barcode sequence attached in proximity to a first end; (b) for each nucleic acid molecule, fragmenting the nucleic acid molecule adjacent to a random portion of the nucleic acid molecule to provide a second end; (c) for each nucleic acid molecule, joining the first end with the second end to provide a circularized nucleic acid molecule having the barcode sequence adjacent to the random portion of the nucleic acid sequence; (d) for each nucleic acid molecule, sequencing the barcode and the random portion of the nucleic acid molecule; and (e) assembling the sequence of the nucleic acid molecule from the plurality of random portions of the nucleic acid molecule. In some embodiments, the method is performed with a plurality of clonal nucleic acid populations each having a different barcode sequence attached thereto, and a separate sequence is assembled in (e) for each of the barcode sequences.

An additional aspect of the disclosure provides a method that comprises: (a) providing a plurality of target nucleic acid molecules; (b) providing a plurality of adapter fragments, each comprising a first region that is identical for each of the adapter fragments and a second region that is unique for each of the adapter fragments; (c) attaching the adapter fragments of (b) to the target nucleic acid molecules of (a) to create a plurality of adapter-ligated target molecules; (d) amplifying the adapter-ligated target molecules of (c); (e) fragmenting the amplified molecules of (d); (f) circularizing the fragmented molecules of (e); (g) fragmenting the circularized molecules of (f); and (h) sequencing the fragmented molecules of (g).

Another aspect of the disclosure provides a method that comprises: (a) providing a plurality of target nucleic acid molecules; (b) providing a plurality of adapter fragments, each comprising a first region that is identical for each of the adapter fragments and a second region that is unique for each of the adapter fragments; (c) attaching the adapter fragments of (b) to the target nucleic acid molecules of (a) to create a plurality of adapter-ligated target molecules; (d); (e) amplifying the adapter-ligated target molecules of (c); (f) fragmenting the amplified molecules of (d); (g) circularizing the fragmented molecules of (e); and (h) sequencing the circularized molecules of (f).

In some aspects, the attaching in (c) is performed by polymerase chain reaction (PCR). In some aspects, the attaching in (c) is performed by ligation.

Another aspect of the disclosure provides a method comprising: (a) sequencing a plurality of nucleic acids located at positions on an array; and (b) measuring a phenotype of a molecule at the positions on the array.

An additional aspect of the disclosure provides a method comprising sequencing a genetic component of the members of a polypeptide display library.

An additional aspect of the disclosure provides a method for generating a plurality of linked sequence-phenotype pairs, the method comprising: (a) applying to an array, a library of mutant proteins associated with their encoding nucleic acid, wherein the library is applied with essentially one mutant per array position; (b) measuring the phenotype of the protein at each array position; and (c) sequencing at least part of the nucleic acid associated with the protein at each array position, thereby generating a linked sequence-phenotype pair at each array position.

An additional aspect of the disclosure provides a method for generating a plurality of linked sequence-phenotype pairs, the method comprising: (a) applying to an array, a library of mutant nucleic acids, wherein the library is applied with essentially one mutant per array position; (b) measuring the phenotype of the nucleic acid at each array position; and (c) sequencing at least part of the nucleic acid at each array position, thereby generating a linked sequence-phenotype pair at each array position.

An additional aspect of the disclosure provides a method for generating a plurality of linked sequence-phenotype pairs, the method comprising: (a) applying to an array, a library of mutant nucleic acids, wherein the library is applied with essentially one mutant per array position; (b) expressing the proteins encoded by the nucleic acids on the array; (c) measuring the phenotype of the proteins at each array position; and (d) sequencing at least part of the nucleic acid at each array position, thereby generating a linked sequence-phenotype pair at each array position.

An additional aspect of the disclosure provides a method for generating a plurality of linked sequence-phenotype pairs, the method comprising: (a) synthesizing a plurality of nucleic acids at fixed positions on an array; (b) expressing the proteins encoded by the nucleic acids on the array; and (c) measuring the phenotype of the protein at each array position, thereby generating a linked sequence-phenotype pair at each array position.

An additional aspect of the disclosure provides a method for generating a plurality of linked sequence-phenotype pairs, the method comprising: (a) applying to an array of immobilized nucleic acids, a library of mutant proteins associated with their encoding nucleic acid, wherein the immobilized nucleic acids hybridize with the nucleic acids that are associated with the mutant proteins; and (b) measuring the phenotype of the protein at each array position, thereby generating a linked sequence-phenotype pair at each array position.

In some aspects, the method further comprises analyzing the linked sequence-phenotype pairs to determine: (i) a sequence that expresses or has a high probability of expressing a protein having a desired phenotype; and/or (ii) a plurality of sequences, wherein at least one of the sequences has a high probability of expressing a protein having a desired phenotype; and/or (iii) the effect of individual sequence mutations on the phenotype of the protein expressed from the sequence; and/or (iv) the effect of a group of sequence mutations on the phenotype of the protein expressed from the sequence; and/or (v) a set of allowed mutations at a sequence position, wherein the protein expressed from the sequence has an acceptable phenotype.

In some aspects, the method further comprises analyzing the linked sequence-phenotype pairs to determine: (1) a nucleic acid molecule that has a high probability of having a desired phenotype; and/or (2) a plurality of nucleic acid molecules, wherein at least one of the molecules that has a high probability of having a desired phenotype; and/or (3) the effect of individual sequence mutations on the phenotype of a nucleic acid molecule; and/or (4) the effect of a group of sequence mutations on the phenotype of a nucleic acid molecule; and/or (5) a set of allowed mutations at a sequence position, wherein the nucleic acid molecule has an acceptable phenotype. In some aspects, the method is used to evolve a protein to a desired phenotype.

An additional aspect of the disclosure provides a method of directed evolution, the method comprising: (a) from a first plurality of sequences, generating a first plurality of linked sequence-phenotype pairs (e.g., via a method for sequencing a nucleic acid molecule described herein); (b) analyzing the first linked sequence-phenotype pairs to design a plurality of second sequences, wherein at least one of the second sequences has a high probability of expressing a protein having a desired phenotype; (c) optionally generating and analyzing a second plurality of linked sequence-phenotype pairs according to the methods of any of the claims; and (d) optionally iterating this cycle as many times as necessary to isolate a protein with the desired phenotype.

An additional aspect of the disclosure provides a method of directed evolution, the method comprising: (a) generating a library of mutant polypeptides associated with their encoding nucleic acids; (b) applying the library to an array, whereby there is essentially one mutant per array position; (c) measuring the phenotype of the mutant polypeptide at each array position; (d) sequencing at least part of the nucleic acid at each array position; and (e) analyzing the linked phenotype data and sequence data, wherein the linked data informs mutations suitable for evolving the polypeptide toward a desired phenotype.

An additional aspect of the disclosure provides an apparatus comprising an array, wherein the array is capable of sequencing nucleic acids and measuring a phenotype of a protein.

An additional aspect of the disclosure provides an apparatus comprising a member that collects linked sequence-phenotype data from an array of nucleic acid-protein pairs.

In some aspects, the array comprises at least $10^4$ positions. In some aspects, the array comprises at least $10^5$ positions. In some aspects, the array comprises at least $10^6$ positions. In some aspects, the array comprises at least $10^7$ positions. In some aspects, the array comprises at least $10^8$ positions. In some aspects, the array comprises one or more sensors. In some aspects, the array is interrogated by one or more sensors. In some aspects, the one or more sensors comprise a chemical field-effect transistor (chemFET) sensor. In some aspects, the sensors measure a signal associated with at least one of fluorescence, pH change and luminescence. In some aspects, the signal is proportional to a phenotype or relatable to a phenotype by a calibration curve. In some aspects, the signal is a change in temperature at a given array position.

In some aspects, the mutant proteins are associated with their encoding nucleic acid by attachment to a microbead. In some aspects, the mutant proteins are associated with their encoding nucleic acid by ribosome display. In some aspects, the mutant proteins are associated with their encoding nucleic acid by RNA display. In some aspects, the mutant proteins are associated with their encoding nucleic acid by DNA display.

In some aspects, the phenotype is enzyme rate. In some aspects, the phenotype is enzyme specificity. In some aspects, the phenotype is binding affinity. In some aspects, the phenotype is binding specificity.

In some aspects, a method further comprises contacting proteins to a plurality of solutions comprising substrates at a plurality of concentrations. In some aspects, a method further comprises contacting proteins to a plurality of solutions comprising ligands at a plurality of concentrations. In some aspects, a method further comprises measuring the phenotype at a plurality of temperatures. In some aspects, the phenotype is stability when exposed to a chemical condition or a temperature. In some aspects, the protein is expressed using cell-free protein synthesis.

In some aspects, the protein is expressed in an emulsion. In some aspects, the nucleic acid is amplified in an emulsion PCR. In some aspects, the protein is labeled at a defined stoichiometry, wherein the label is used to determine the number of proteins at the array position. In some aspects, the protein associates with a known stoichiometry of probe molecule on the array. In some aspects, the probe molecule is an antibody linked to a fluorescent molecule, an enzyme, or an enzymatic substrate. In some aspects, the nucleic acid is sequenced more than once. In some aspects, the nucleic acid is sequenced a plurality of times starting from various positions along the nucleic acid sequence. In some aspects, the nucleic acid is amplified in an emulsion PCR, wherein a plurality of secondary nucleic acid molecules are created corresponding to different portions of the nucleic acid, wherein the secondary nucleic acid molecules are sequenced.

With respect to aspects of the disclosure that have been described as a set or genus, every individual member of the set or genus is intended, individually, as an aspect of the disclosure, even if, for brevity, every individual member has not been specifically mentioned herein. When aspects of the disclosure are described herein as being selected from a genus, it should be understood that the selection can include mixtures of two or more members of the genus. Similarly, with respect to aspects of the disclosure described herein as a range, such as a range of values, every sub-range within the range is considered an aspect of the disclosure.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also "FIG." and "FIGs." herein), of which:

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Aspects of the disclosure described with "a" or "an" should be understood to include "one or more" unless the context clearly requires a narrower meaning.

The disclosure provides an improved method for obtaining nucleic acid sequence information. In various aspects, the method permits the quicker and more accurate assembly of intermediate and long read lengths of target nucleic acids from short nucleic acid sequences.

The disclosure also provides methods for obtaining nucleic acid sequence information by reconstructing intermediate and/or long nucleic acid sequences from the assembly of short or intermediate nucleic acid sequences.

Figure 1A:
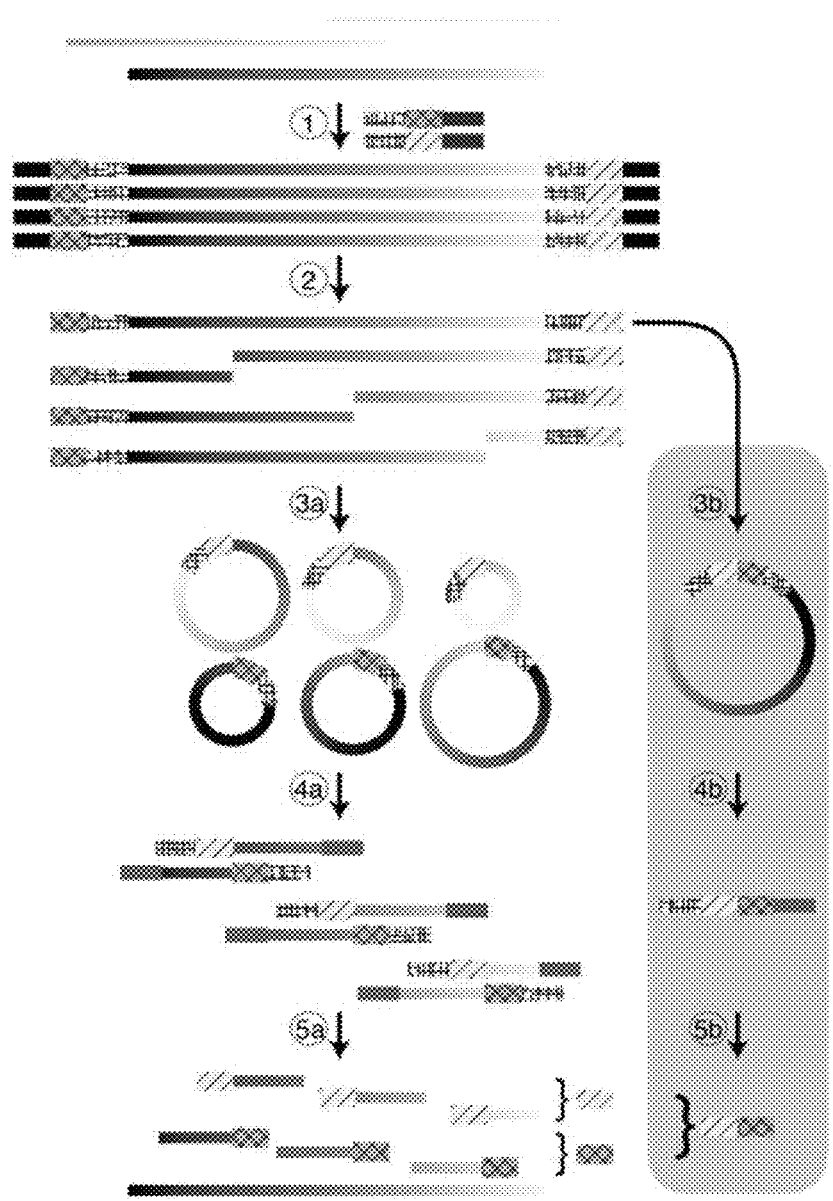
FIG. 1A shows a schematic illustration of an example method for assembling sequences of individual nucleic acid molecules.
Figure 1B:
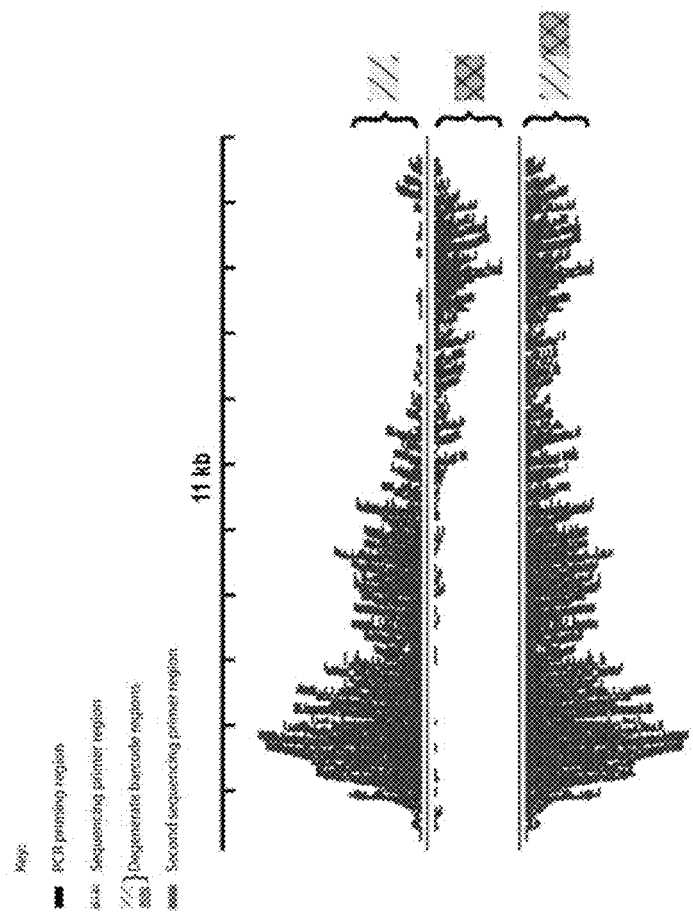
FIG. 1B shows example data that barcode pairing can improve assembly lengths.

FIG. 1A and FIG. 1B provide an illustration of an example embodiment of the disclosure, and shows how barcode pairing (as described herein) improves sequence assembly of long nucleic acid sequences. FIG. 1A shows a schematic illustration of a method for assembling sequences of individual nucleic acid molecules. Mixed target molecules are tagged with tripartite adapters comprising an outer PCR priming region (black bar), an inner region containing a sequencing primer region (burlap bars), and a central degenerate barcode region (diagonal bars and diamond bars). PCR is carried out generating many copies of each tagged molecule (1 in FIG. 1A). The priming region is removed by enzymatic digestion and a single break (on average) is made in each copy of the tagged molecule (2 in FIG. 1A). Tagged nucleic acid molecules are circularized (3a in FIG. 1A) bringing the newly exposed end of the fragment into proximity with the barcode. Circularized, tagged nucleic acid molecules are linearized; a second sequencing primer/adapter (grey bar) is added; and sequencing-ready libraries are prepared (4a in FIG. 1A). Sequence reads begin with the barcode sequence and continue into the unknown region. Short reads are grouped by common barcodes to assemble the original target molecule (5a in FIG. 1A). A barcode-pairing protocol (grey box) is used to resolve the two distinct barcodes affixed to each original target molecule. Circularization of unbroken copies (3b in FIG. 1A) brings the two barcodes together. Subsequent sequencing reads contain both barcode sequences (4b in FIG. 1A), allowing the two barcode-defined groups to be collapsed into a single group (5b in FIG. 1A).

Figure 1C:
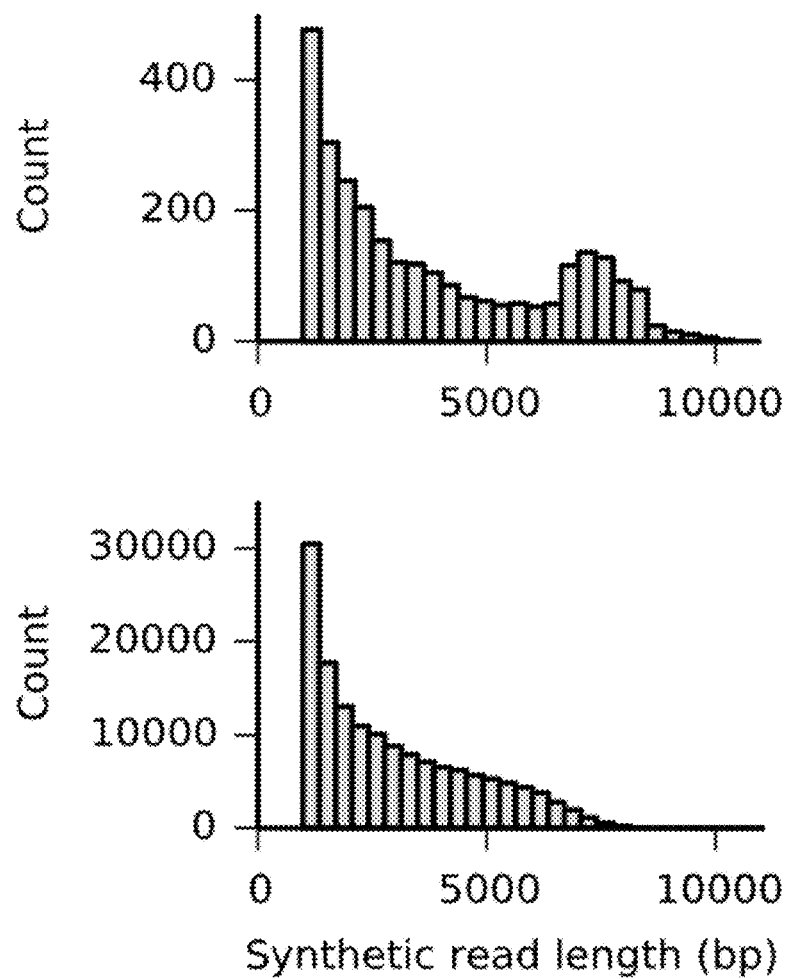
FIG. 1C provides example length histograms of the contiguous sequences ("contigs") assembled from genomic reads (minimum lengths of about 1000 bps) from *E. coli* MG1655 (top panel) and *Gelsemium sempervirens* (bottom panel)

FIG. 1B shows that barcode pairing cam improve assembly lengths. Reads associated with two distinct barcodes are shown aligned to the MG1655 reference genome. Individually, each group of reads (top) assembles into a contiguous sequence ("contig") about 6 kb in length. Barcode pairing merges the groups (bottom), increasing and smoothing coverage across the region to allow assembly of the full 10-kb target sequence. FIG. 1C provides length histograms of the contigs assembled from genomic reads (minimum length of about 1000 bp) from *E. coli* MG1655 (top panel) and *Gelsemium sempervirens* (bottom panel). The N50 length of the synthetic reads for *E. coli* MG1655 is 6.0 kb, and the longest synthetic read (contig) in this example is 11.6 kb. The N50 length of the synthetic reads is 4.0 kb.

Figure 2:
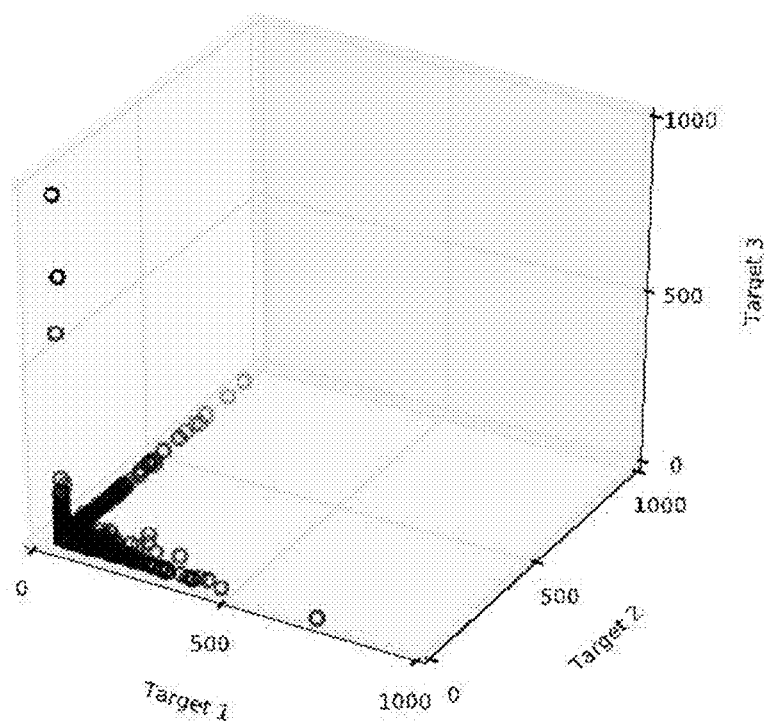
FIG. 2 shows an example three-dimensional scatter plot (inset) showing barcode fidelity in sequencing results from a mixture of three homologous 3-kb plasmids (i.e., three target nucleic acid molecules)

FIG. 2 shows an example three-dimensional scatter plot (inset) showing barcode fidelity in sequencing results from a mixture of three homologous 3-kb plasmids (i.e., three target nucleic acid molecules). The reads associated with each barcode were searched for short sequences unique to each variant. Each point represents a different barcode (about 8000 total) and its position indicates the number of times sequences unique to each of three mixed target molecules were found within that set of barcode-grouped reads. Counting the barcodes associated with each target molecule provides a measurement of mixture composition. Although Target 3 was rare in the mixture, the barcodes that tagged Target 3 had as many counts as barcodes tagging more abundant targets.

Figure 3:
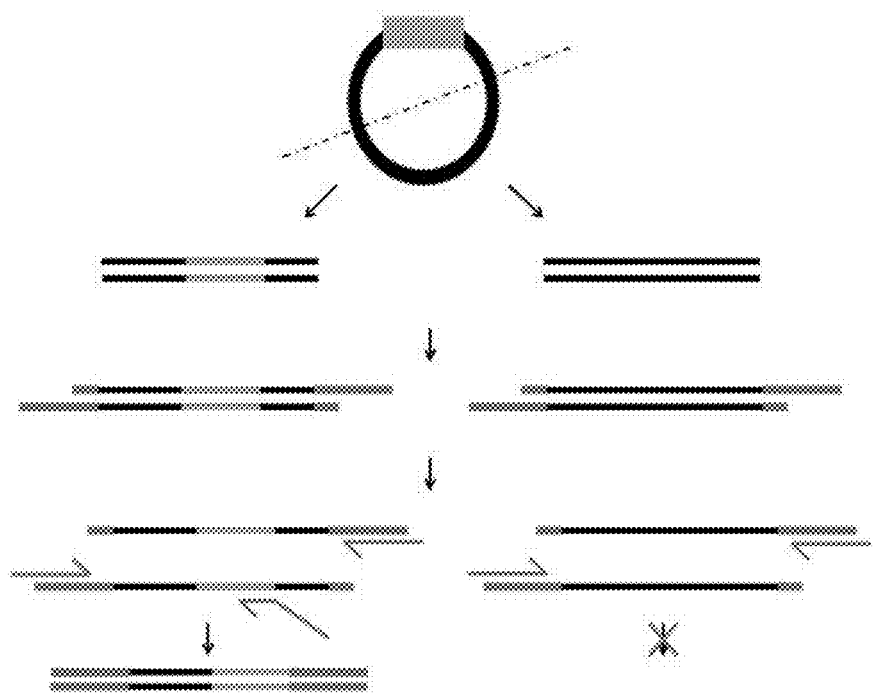
FIG. 3 is a detailed schematic of an example conversion of sheared circular DNA into a sequencing-ready library.

FIG. 3 is a detailed schematic of an aspect of the disclosure showing example conversion of sheared circular DNA into a sequencing-ready library. Circularized DNA (black) containing barcode and annealing sequences (grey) is fragmented (dotted line) into molecules of about 500 bp in length. Some of the resulting molecules will contain a barcode and others will not. Asymmetric adapters are ligated to each end of the molecules. Limited-cycle PCR is performed with a first primer complementary to the asymmetric adapter and a second primer complementary to the internal annealing sequence from the tripartite adapter. The primers add the full sequencing adapter sequences to the PCR product. Only molecules containing internal annealing sequences and barcodes are exponentially amplified in the PCR.

Figure 4:
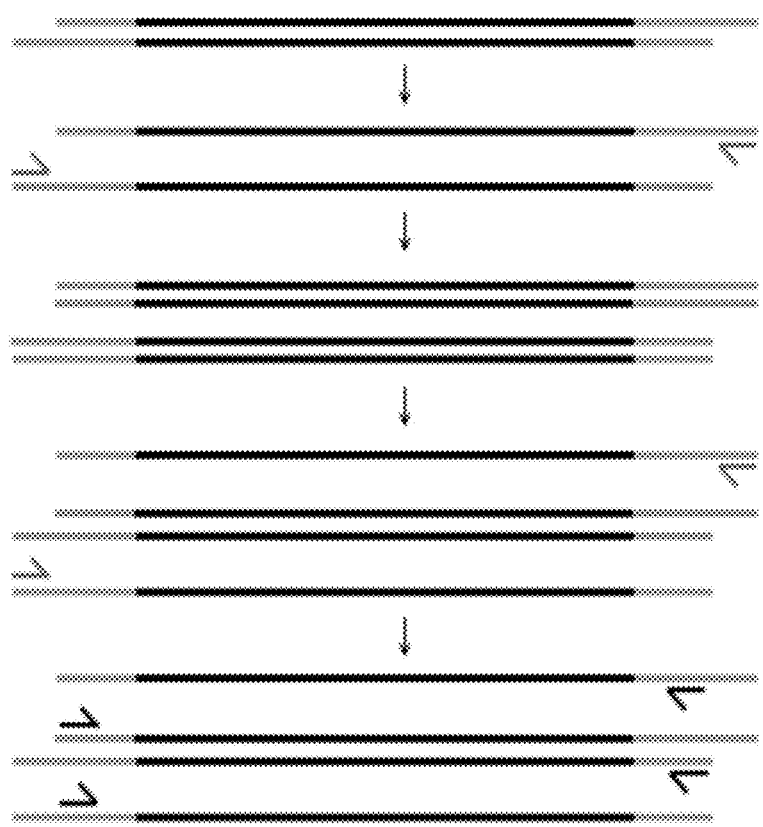
FIG. 4 is a schematic diagram showing example linear amplification of nucleic acid sequence prior to exponential PCR to reduce amplification bias.

FIG. 4 is a schematic diagram of an aspect of the disclosure showing example linear amplification of nucleic acid sequence prior to exponential PCR to reduce amplification bias. In some aspects, the tripartite adapter is designed with an overhang containing an annealing region for a linear amplification primer (grey arrow). Each round of thermocycling in the presence of this primer copies the original adapter ligated molecules. However, the newly synthesized copies will not themselves be copied because they do not have the annealing site for the linear amplification primer. Exponential PCR can be triggered by the addition of a second primer (black arrow).

Figure 5:
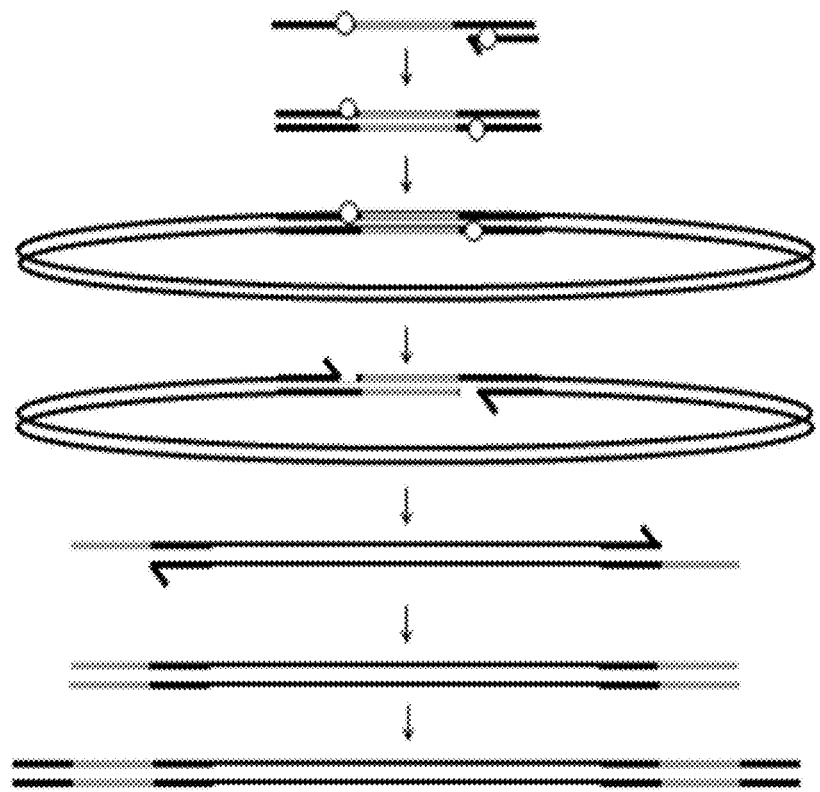
FIG. 5 is a schematic diagram showing an example approach used to attach the same barcode to both ends of a target molecule.

FIG. 5 is a schematic diagram of an aspect of the disclosure showing an example approach used to attach the same barcode to both ends of a target molecule. An oligonucleotide is synthesized containing a uracil base (white circle) and a degenerate barcode region (grey region). A second oligonucleotide is synthesized to contain a uracil base and to be complementary to a region of the first oligonucleotide. The second oligonucleotide anneals to the first and is extended by a DNA polymerase, copying the barcode region and forming a double-stranded molecule. The target molecule is circularized around the double-stranded adapter. USER enzyme excises the uracil bases, creating nicks in each strand, and opening the circular molecule into a linear molecule. DNA polymerase extends the new 3' ends, copying the single-stranded barcode regions to create a fully double-stranded molecule. An additional adapter containing a PCR primer annealing sequence is ligated to both ends of the linear molecule. The end result is a linear molecule with the same barcode on both ends.

Figure 6:
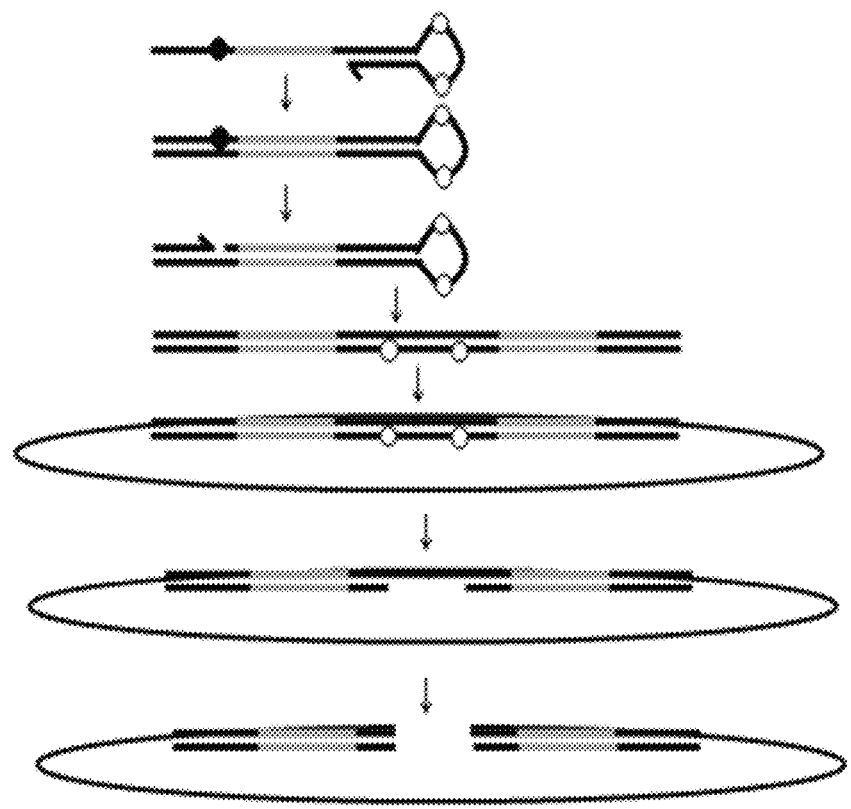
FIG. 6 is a schematic diagram of showing another example approach used to attach the same barcode to both ends of a target molecule, by creating a circularizing barcode adapter containing two full copies of the same degenerate barcode.

FIG. 6 is a schematic diagram of an aspect of the disclosure showing another example approach used to attach the same barcode to both ends of a target molecule, by creating a circularizing barcode adapter containing two full copies of the same degenerate barcode. An oligonucleotide (i.e., "oligo") is synthesized to contain a nicking endonuclease site (black circle), a degenerate barcode (grey), a self-priming hairpin, and two or more uracil bases (white circles). The self-priming 3' end is extended with DNA polymerase, copying the barcode sequence. The DNA is nicked at the newly double-stranded nicking endonuclease site, creating a free 3' end. The free 3' end is extended by a strand-displacing DNA polymerase, which copies the barcode sequence yet again. The target molecule is circularized around the barcode adapter by ligation. In some aspects, USER enzyme excises two or more uracils from the original synthetic strand, creating a single-strand gap. S1 nuclease or mung bean nuclease degrades the single-stranded DNA, opening the circle into a linear molecule with identical barcodes at both ends.

Figure 7:
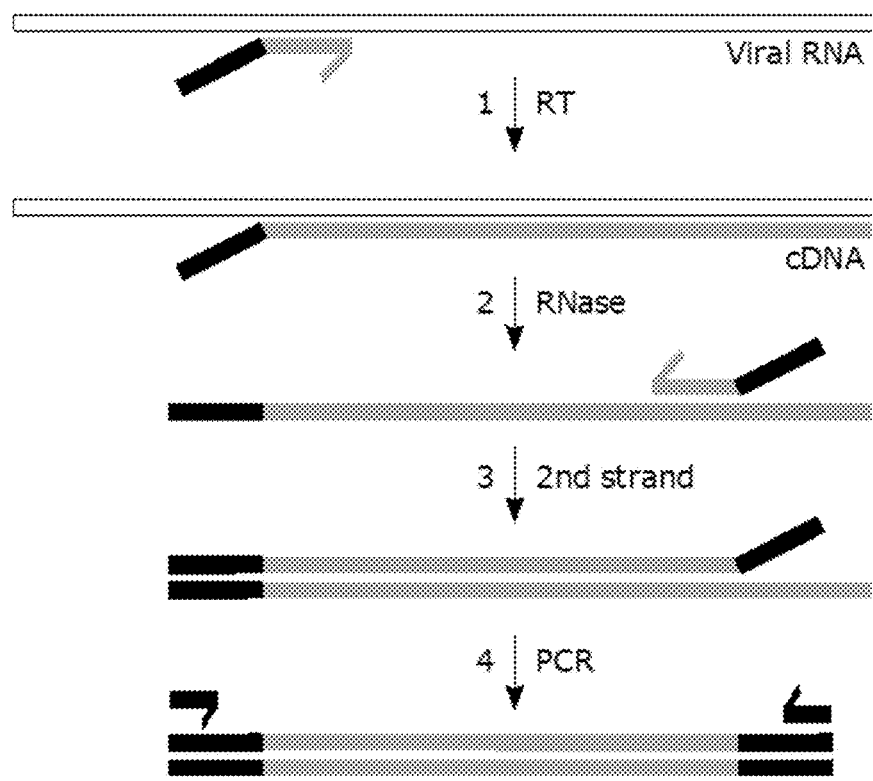
FIG. 7 is a schematic diagram showing an example approach for incorporating barcodes to full-length cDNA during reverse-transcription.

FIG. 7 is a schematic diagram of an aspect of the disclosure showing an example approach for incorporating barcodes to full-length cDNA during reverse-transcription. (1) RNA (white) is reverse transcribed (RT) from a primer comprising an annealing portion (grey) and a tripartite overhang portion (black) containing a barcode. (2) Following 1st strand synthesis, the RNA is degraded by RNase treatment and excess primers are removed. (3) A second tripartite barcode-containing primer is added and the 2nd strand is synthesized. (4) Excess primers are removed, and full-length cDNA is exponentially amplified by PCR with a third primer (black arrows) complimentary to adapters on both strands.

Figure 8A:
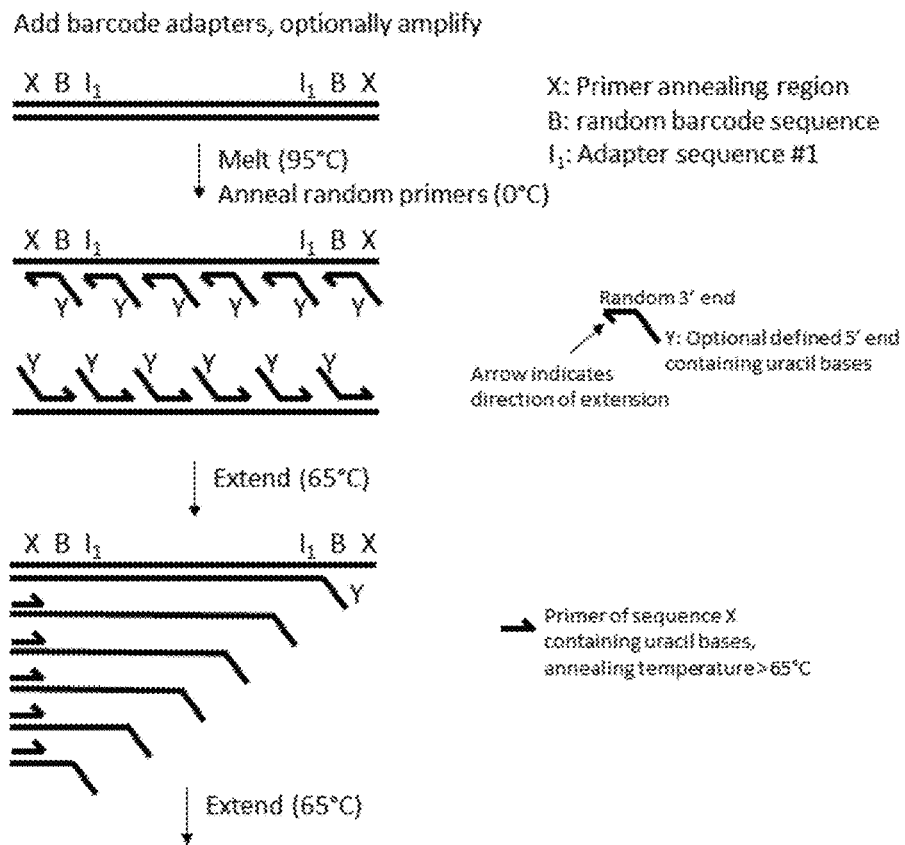
FIG. 8A is a schematic diagram of an example method for fragment generation based on extension of random primers.
Figure 8B:
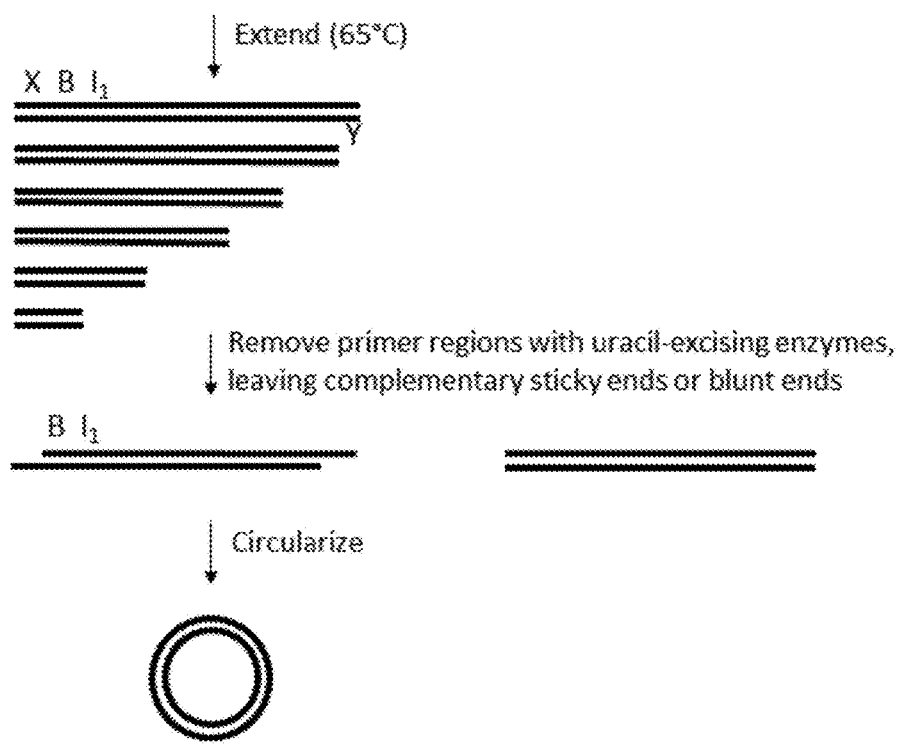
FIG. 8B continues from FIG. 8A and completes the example method of fragment generation based on extension of random primers.

FIG. 8A and FIG. 8B schematically depict an alternate, example approach to creating fragments that relies on extension of random primers rather than breaking full-length copies. Following adapter attachment and optional PCR, the strands are denatured and random primers are annealed along the length of the target molecule. The primers can be designed with a random sequence at the 3' end (e.g., $N_4$ to $N_8$) and optionally a defined sequence at the 5' end that is the reverse complement of the sequence at the ends of the target molecule (denoted by "X" in the figure) and contains uracil bases. Extension of the random primers with a strand-displacing polymerase creates single-stranded fragments with one random end defined by the annealing site of the random primer and a second end defined by the termination of extension at end of the target fragment. Second-strand synthesis with an additional primer with a sequence corresponding to X and containing one or more uracil bases can create double-stranded fragments. Both extension rounds can be performed at a relatively high temperature to prevent further annealing of the random primers. The double-stranded fragments can be circularized by blunt-end ligation, or if the X-complementary overhangs were used, USER enzyme mix (New England Biolabs) can be used to excise the uracil-containing regions to produce sticky ends to increase circularization efficiency.

Nucleic Acids and Nucleic Acid Libraries

A nucleic acid or nucleic acid molecule, as used herein, can include any nucleic acid of interest. In some embodiments, nucleic acids include, but are not limited to, DNA, RNA, peptide nucleic acid, morpholino nucleic acid, locked nucleic acid, glycol nucleic acid, threose nucleic acid, mixtures thereof, and hybrids thereof. In some aspects, a nucleic acid is a "primer" capable of acting as a point of initiation of synthesis along a complementary strand of nucleic acid when conditions are suitable for synthesis of a primer extension product.

In some aspects, the nucleic acid serves as a template for synthesis of a complementary nucleic acid, e.g., by base-complementary incorporation of nucleotide units. For example, in some aspects, a nucleic acid comprises naturally occurring DNA (including genomic DNA), RNA (including mRNA), and/or comprises a synthetic molecule including, but not limited to, complementary DNA (cDNA) and recombinant molecules generated in any manner. In some aspects, the nucleic acid is generated from chemical synthesis, reverse transcription, DNA replication or a combination of these generating methods. In some aspects, the linkage between the subunits is provided by phosphates, phosphonates, phosphoramidates, phosphorothioates, or the like, or by nonphosphate groups, such as, but not limited to, peptide-type linkages utilized in peptide nucleic acids (PNAs). In some aspects, the linking groups are chiral or achiral. In some aspects, the polynucleotides have any three-dimensional structure, encompassing single-stranded, double-stranded, and triple helical molecules that are, e.g., DNA, RNA, or hybrid DNA/RNA molecules, and double-stranded with single-stranded regions (for example, stem- and loop-structures).

In some aspects, nucleic acids are obtained from any source. In various aspects, nucleic acid molecules are obtained from a single organism or from populations of nucleic acid molecules obtained from natural sources that include one or more organisms. Sources of nucleic acid molecules include, but are not limited to, organelles, cells, tissues, organs, and organisms. In some aspects, when cells are used as sources of nucleic acid molecules, the cells are derived from any prokaryotic or eukaryotic source. Such cells include, but are not limited to, bacterial cells, fungal cells, plant cells (including vegetable cells), protozoan cells, and animal cells. Such animal cells include, but are not limited to, insect cells, nematode cells, avian cells, fish cells, amphibian cells, reptilian cells, and mammalian cells. In some aspects, the mammalian cells include human cells.

Nucleic acids can be obtained using any suitable method, including those described by Maniatis et al., Molecular Cloning: A Laboratory Manual, Cold Spring Harbor, N.Y., pp. 280-281 (1982). In some aspects, nucleic acids are obtained as described in U.S. Patent Application Publication No. US2002/0190663. Nucleic acids obtained from biological samples typically are fragmented to produce suitable fragments for analysis.

In some aspects, a nucleic acid of interest or "target nucleic acid" or "target nucleotide sequence" to be sequenced is fragmented or sheared to a desired length. The terms "fragmenting," "shearing," or "breaking" are used interchangeably in various aspects herein to mean cutting or cleaving the nucleic acid into at least two or more smaller pieces or fragments. In various aspects, a nucleic acid is shortened, or broken into fragments of shorter lengths, in the preparation of a high quality sequencing library or "target library," which is important in next-generation sequencing (NGS). In various embodiments, a "target library" or "target nucleic acid library" is created. The target library comprises fragments of a target nucleic acid of interest. The term "target nucleic acid" or "target nucleotide" or "target nucleotide sequence" is used herein interchangeably to refer to the nucleic acid or nucleotide to be sequenced.

In various aspects, a nucleic acid is fragmented or shortened by physical, chemical, or enzymatic shearing. In various aspects, physical fragmentation is carried out by acoustic shearing, sonication, or hydrodynamic shear. In many aspects, acoustic shearing and sonication are popular physical methods used to shear DNA. In some aspects, the Covaris® instrument (Covaris, Woburn, Mass.) is an acoustic device used for breaking DNA into fragments of about 100 bp to about 5000 bp. In other aspects, the Bioruptor® (Denville, N.J.) is a sonication device utilized for shearing chromatin, DNA and disrupting tissues. Small volumes of DNA are sheared to about 150 to about 1 kb in length. Hydroshear (Digilab, Marlborough, Mass.) utilizes hydrodynamic forces to shear DNA. In some aspects, DNA is sheared by nebulizers (Life Tech, Grand Island, N.Y.), which atomize liquid using compressed air, and results in shearing DNA into fragments of about 100 bp to about 3000 bp in seconds. In various aspects, enzymatic fragmentation or shearing is carried out by fragmentase (NEB, Ipswich, Mass.), KAPA Frag Enzyme (KAPA, Wilmington, Mass.), DNase I, non-specific nuclease, transposase, another restriction endonuclease, or Nextera tagmentation technology (Illumina, San Diego, Calif.). In various aspects, chemical fragmentation is carried out. Chemical fragmentation includes, but is not limited to, exposure to heat and divalent metal cations. Chemical shear is typically reserved for the breakup of long RNA fragments, and is typically performed through the heat digestion of RNA with a divalent metal cation (magnesium or zinc). In some aspects, the length of the RNA (about 115 nucleotides to about 350 nucleotides) is adjusted by increasing or decreasing the time of incubation. In some aspects, a nucleic acid molecule is shortened with an exonuclease.

In various aspects, the size of the nucleic acid fragment is a key factor for library construction and sequencing. In various aspects, a sequencing platform and read length is chosen to be compatible with fragment size. In some aspects, size selection of nucleic acids is performed to remove very short fragments or very long fragments.

In various aspects, fragmentation is carried out in various stages of the method disclosed herein. For example, in some aspects, there are three fragmentation rounds. For example, in some aspects, if genomic DNA is used as a starting material (rather than mRNA or a PCR product), genomic DNA is fragmented in a first fragmentation into pieces of about 8 kb to about 10 kb. Those fragments of about 8 kb to about 10 kb are tagged and amplified. The amplified copies, in various aspects, are further fragmented in a second fragmentation, ideally breaking them one time somewhere along their length into fragments of various lengths. These fragments of various lengths are circularized, and the circles are fragmented again in a third fragmentation to fragments of about 300 bases to about 800 bases.

In various aspects, therefore, fragment size is about 0.1 kilobase (kb), about 0.15 kb, about 0.2 kb, about 0.25 kb, about 0.3 kb, about 0.35 kb, about 0.4 kb, about 0.45 kb, about 0.5 kb, about 0.55 kb, about 0.6 kb, about 0.65 kb, about 0.7 kb, about 0.75 kb, about 0.8 kb, about 0.85 kb, about 0.9 kb, about 0.95 kb, about 1.0 kb, about 1.5 kb, about 2.0 kb, about 2.5 kb, about 3.0 kb, about 3.5 kb, about 4.0 kb, about 4.5 kb, about 5.0 kb, about 5.5 kb, about 6.0 kb, about 6.5 kb, about 7.0 kb, about 7.5 kb, about 8.0 kb, about 8.5 kb, about 9.0 kb, about 9.5 kb, about 10 kb, about 11 kb, about 12 kb, about 13 kb, about 14 kb, about 15 kb, about 16 kb, about 17 kb, about 18 kb, about 19 kb, about 20 kb, about 30 kb, about 40 kb, about 50 kb, about 60 kb, about 70 kb, about 80 kb, about 90 kb, about 100 kb, about 1000 kb, or longer.

In various aspects, size selection is carried out. In some aspects, size-selection is used, after shearing genomic DNA into large fragments, to separate desirable nucleic acid fragments of a size of about 8 kb to about 10 kb from smaller fragments, which would preferentially amplify during PCR and ultimately yield synthetic reads of limited usefulness. In some aspects, size selection is used after fragmentation of PCR products to enrich the library for fragments of a particular size to compensate for diminished circularization efficiency of fragments depending on size. In some aspects, circularization efficiency is reduced if fragment length is too long.

In some aspects, size selection is carried out using length-dependent binding to solid phase reversible immobilization (SPRI®, Beckman Coulter) beads. In other aspects, size selection is carried out using agarose or polyacrylamide electrophoresis gel purification and isolation. Size selection via gel electrophoresis purification and isolation may be performed manually or with an automated system such as BluePippen (Sage Science, Beverly, Mass.) or E-gels (Thermo Fisher Scientific)

The term "long nucleotide sequence," "long nucleic acid sequence," or "long read" as used herein refers to any nucleic acid sequence equal to or greater than 20,000 bases (or 20,000 nucleotides, or 20 kilobases, or 20 kb). In some aspects, the long nucleotide sequence is between approximately 20000 bases to approximately 500,000 bases. In some aspects, the long nucleotide sequence is between approximately 25000 bases to approximately 100,000 bases. In some aspects, the long nucleotide sequence is about 20000 bases, about 25000 bases, about 30000 bases, about 35000 bases, about 40000 bases, about 45000 bases, about 50000 bases, about 55000 bases, about 60000 bases, about 65000 bases, about 70000 bases, about 75000 bases, about 80000 bases, about 85000 bases, about 90000 bases, about 95000 bases, about 100,000 bases, about 150,000 bases, about 200,000 bases, about 250,000 bases, about 300,000 bases, about 350,000 bases, about 400,000 bases, about 450,000 bases, or about 500,000 bases.

The term "intermediate nucleotide sequence," "intermediate nucleic acid sequence," or "intermediate read" as used herein refers to any nucleic acid sequence greater than 1000 bases and less than 20,000 bases. In some aspects, the intermediate nucleotide sequence is between approximately 1500 bases and approximately 15000 bases. In some aspects, the intermediate nucleotide sequence is between approximately 2000 bases to approximately 12000 bases. In some aspects, the intermediate nucleotide sequence is between approximately 3000 bases to approximately 11000 bases. In some aspects, the intermediate nucleotide sequence is between approximately 4000 bases to approximately 10000 bases. In some aspects, the intermediate nucleotide sequence is about 1050 bases, about 1100 bases, about 1150 bases, about 1200 bases, about 1250 bases, about 1300 bases, about 1350 bases, about 1400 bases, about 1450 bases, about 1500 bases, about 1550 bases, about 1600 bases, about 1650 bases, about 1700 bases, about 1750 bases, about 1800 bases, about 1850 bases, about 1900 bases, about 1950 bases, about 2000 bases, about 2100 bases, about 2200 bases, about 2300 bases, about 2400 bases, about 2500 bases, about 3000 bases, about 3500 bases, about 4000 bases, about 4500 bases, about 5000 bases, about 5500 bases, about 6000 bases, about 6500 bases, about 7000 bases, about 7500 bases, about 8000 bases, about 8500 bases, about 9000 bases, about 9500 bases, about 10000 bases, about 11000 bases, about 12000 bases, about 13000 bases, about 14000 bases, about 15000 bases, about 16000 bases, about 17000 bases, about 18000 bases, about 19000 bases, or less than about 20000 bases.

The term "short nucleotide sequence," "short nucleic acid sequence," or "short read" as used herein refers to any nucleic acid sequence less than or equal to 1000 bases or 1000 nucleotides. In some aspects, the short nucleotide sequence is between approximately 25 bases to approximately 1000 bases. In some aspects, the short nucleotide sequence is between approximately 50 bases to approximately 750 bases. In some aspects, the short nucleotide sequence is between approximately 75 bases to approximately 500 bases. In some aspects, the short nucleotide sequence is about 25 bases, about 50 bases, about 75 bases, about 100 bases, about 125 bases, about 150 bases, about 175 bases, about 200 bases, about 250 bases, about 275 bases, about 300 bases, about 325 bases, about 350 bases, about 375 bases, about 400 bases, about 425 bases, about 450 bases, about 475 bases, about 500 bases, about 525 bases, about 550 bases, about 575 bases, about 600 bases, about 675 bases, about 700 bases, about 725 bases, about 750 bases, about 775 bases, about 800 bases, about 825 bases, about 850 bases, about 875 bases, about 900 bases, about 925 bases, about 950 bases, about 975 bases, or about 1000 bases.

Adapters and Adapter Attachment

An "adapter" as used herein is a relatively short, nucleic acid molecule which is attached to a nucleic acid molecule in various aspects of the disclosure. In some aspects, an adapter comprises a variety of sequence elements including, but not limited to, an amplification primer annealing sequence or complement thereof, a sequencing primer annealing sequence or complements thereof, a barcode sequence, a common sequence shared among multiple different adapters or subsets of different adapters, a restriction enzyme recognition sites, an overhang complementary to a target polynucleotide overhang, a probe binding site (e.g., for attachment to a sequencing platform), a random or near-random sequence (e.g., a nucleotide selected at random from a set of two or more different nucleotides at one or more positions, with each of the different nucleotides selected at one or more positions represented in a pool of adapters comprising the random sequence), and combinations thereof. In some aspects, two or more sequence elements are non-adjacent to one another (e.g., separated by one or more nucleotides), adjacent to one another, partially overlapping, or completely overlapping. In some aspects, adapters contain overhangs designed to be complementary to a corresponding overhang on the molecule to which ligation is desired. In some aspects, a complementary overhang is one or more nucleotides in length including, but not limited to, 1, 2, 3, 4, 5, 6, 7, 8, 9, 10, 11, 12, 13, 14, 15, or more nucleotides in length. In some aspects, a complementary overhang comprises a fixed or a random sequence.

In some aspects, the adapter is a "tripartite adapter" comprising a polymerase chain reaction (PCR) primer region, a sequencing primer region, and a barcode region. In some further aspects, the tripartite adapter comprises an outer PCR primer region (or amplification primer region or sequence), an inner sequencing primer region (or sequence), and a central barcode region (or sequence). Barcodes are important in solving the problem of information loss resulting from the shearing of a target nucleic acid into sequencing-compatible fragments. In some aspects, each barcode is specific to the individual intermediate-length nucleic acid molecule from which a given short sequenced nucleic acid molecule is derived and is used to identify the source of the short nucleic acid. In various aspects, therefore, a given barcode is exclusively associated with a single target molecule. Thus, the term "barcode fidelity" as used herein refers to a particular barcode being exclusively associated with a single target molecule. With perfect barcode fidelity, every read tagged with that barcode is derived from that single target molecule and contains nucleotide sequence from that single target molecule alone. Thus, when being assembled (e.g., in a computational pipeline), reads sharing a barcode sequence are distinguished from the background of reads without that particular barcode, and are grouped together and assembled to recreate the sequence of the original longer molecule. A "computational pipeline" or "processing pipeline" is a system for processing sequencing data and assembling the short nucleic acid sequence data into synthetic long nucleic acids.

In some aspects, short defined sequences are designed to follow and/or precede the barcode sequence in the sequencing reads to positively distinguish true barcode sequences from spurious sequences. In some aspects, these constant sequences are selected to promote incorporation of biotinylated deoxyribonucleotides (e.g., biotin-dCTP) into the fragmented molecules during end-repair.

In some aspects, an amplification primer annealing sequence also serves as a sequencing primer annealing sequence. In some aspects, sequence elements are located at or near the ligating end, at or near the non-ligating end, or in the interior of the adapter. In some aspects, when an adapter oligonucleotide is capable of forming secondary structure, such as a hairpin, sequence elements are located partially or completely outside the secondary structure, partially or completely inside the secondary structure, or in between sequences participating in the secondary structure. For example, in some aspects, when an adapter oligonucleotide comprises a hairpin structure, sequence elements are located partially or completely inside or outside the hybridizable sequences (the "stem"), including in the sequence between the hybridizable sequences (the "loop").

In some aspects, the first adapter oligonucleotides in a plurality of first adapter oligonucleotides having different barcode sequences comprise a sequence element common among all first adapter oligonucleotides in the plurality. In some aspects, all second adapter oligonucleotides comprise a sequence element common among all second adapter oligonucleotides that is different from the common sequence element shared by the first adapter oligonucleotides. In some aspects, a difference in sequence elements is any such difference, wherein at least a portion of different adapters do not completely align, for example, due to changes in sequence length, deletion, or insertion of one or more nucleotides, or a change in the nucleotide composition at one or more nucleotide positions (such as a base change or base modification).

In some aspects, partial sequencing primer sequences (e.g., like those available from Illumina) are included adjacent to the random barcode sequence in the barcode adapter. In some aspects, the partial sequence anneals in downstream PCR to a longer oligonucleotide that adds a full sequencing primer sequence (e.g., like those available from Illumina). Alternatively, in some aspects, other sequences are used with a corresponding custom sequence primer in place of a standard sequencing primer mixture.

In some aspects, the adapter comprises sequencing primer sequence proximal to the barcode. This positioning of the sequencing primer and the barcode provides two main benefits. First, because the sequencing read (e.g., Illumina) begins with the sequence directly downstream of the sequencing primer sequence, the barcode sequence is always located at the beginning of one of the two paired-end sequencing reads (e.g., Illumina). After the barcode sequence, the read continues directly into an unknown region derived from the middle of the target molecule. This positioning of the barcode and sequencing primer ensures that the random barcode is easily identifiable, and avoids wasting sequencing capacity by repeatedly sequencing the region on the upstream side of the barcode (which is always derived from the end of the original target molecule).

Second, the presence of a primer sequence (e.g., Illumina) adjacent to the barcode sequence provides a simple way to distinguish nucleic acid fragments containing barcodes from fragments that do not contain barcodes. In some aspects, these latter fragments arise when a copy of the amplified target molecule is broken more than once, creating two end fragments with barcode sequences and one or more middle fragments without barcodes. In these instances, sequencing barcode-free fragments wastes sequencing capacity, because they contain no barcode sequence to link them to a parent nucleic acid molecule. In some aspects, only end fragments containing barcode sequences contain the primer sequences (e.g., Illumina) that are used to selectively amplify these sequences by PCR.

In some aspects, an asymmetric adapter is ligated to both ends of a nucleic acid fragment (see FIG. 3). In some aspects, this ligation of an asymmetric adapter takes place following fragmentation, circularization, and shearing. In some aspects, this asymmetric adapter comprises two oligonucleotides, one of which is longer than the other. In some aspects, the shorter oligonucleotide is complementary to the longer oligonucleotide and, upon annealing, creates a ligation-competent adapter with a 3' dT-tail suitable for specific ligation to the A-tailed fragment. In some aspects, the adapter sequence is complementary to a PCR primer that adds a second sequencing primer sequence (e.g., Illumina) by overlap-extension PCR, but only the longer of the two oligonucleotides is long enough to productively anneal to this primer during PCR. As a result, following ligation of an asymmetric adapter to both ends of a fragment, each of the two strands of the fragment has an annealing-competent sequence at only one end. The second PCR primer in the reaction anneals to the partial sequence (e.g., Illumina) contained within the fragment adjacent to the barcode. As a result, the only exponentially amplified PCR product is the desired nucleic acid fragment, which begins with one sequence (e.g., Illumina), followed by the barcode sequence and unknown sequence from the center of the target molecule, and ends with the second sequence (e.g., Illumina). Fragments of about 500 bp are converted into a sequenceable library by adding any requisite binding sequences (e.g., Illumina flowcell binding sequences) to the ends of the fragments.

In some aspects, library preparation is similar to library preparation carried out with commercial (e.g., Illumina) reagents (e.g., which is done with forked or Y-shaped adapters that ensure that the PCR-amplified products all have adapter 1 on one end and adapter 2 on the other end); however, in the method of the disclosure one of the forks of the Y-shaped adapter is omitted because the fragments of interest already contain an annealing site for one of the two sequencing primers. Therefore, in some aspects, one primer anneals to the remaining fork, and the other primer anneals to a site in the interior of the fragment. In some aspects, therefore, (e.g., Illumina) sequences are used to ensure compatibility with standard sequencing reagents (e.g., Illumina) used in the sequencing methods. In some aspects, therefore, sequencing is carried out using a number or variety of sets of sequences (e.g., TruSeq kit, Small RNA kit, and the like, any of which are useful in various aspects described herein.

In some aspects, an adapter comprises a region that is identical among all members of the adapter population and a degenerate barcode region that is unique to each member of the population. In general, a barcode comprises a nucleic acid sequence that when observed together with a polynucleotide serves as an identifier of the sample or molecule from which the polynucleotide was derived. As used herein, the term "barcode" refers to a nucleic acid sequence that allows some feature of a polynucleotide with which the barcode is associated to be identified. In some aspects, the feature of the polynucleotide to be identified is the sample or molecule from which the polynucleotide is derived. In some aspects, barcodes are at least 3, 4, 5, 6, 7, 8, 9, 10, 11, 12, 13, 14, 15, 16, or more nucleotides in length. In some aspects, barcodes are shorter than 10, 9, 8, 7, 6, 5, or 4 nucleotides in length. In some aspects, barcodes associated with some polynucleotides are of different lengths than barcodes associated with other polynucleotides. In general, barcodes are of sufficient length and comprise sequences that are sufficiently different to allow the identification of samples based on barcodes with which they are associated. In some aspects, a barcode, and the sample source with which it is associated, is identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some aspects, each barcode in a plurality of barcodes differ from every other barcode in the plurality by at least two nucleotide positions, for example, by at least 2, 3, 4, 5, 6, 7, 8, 9, 10, or more positions. In some aspects, both a first adapter and a second adapter comprise at least one of a plurality of barcode sequences. In some aspects, barcodes for second adapter oligonucleotides are selected independently from barcodes for first adapter oligonucleotides.

In some aspects, the tripartite adapter further comprises an index sequence to facilitate multiplexing of more than one sample for simultaneous preparation and sequencing. As opposed to the barcode region, the index region is not degenerate but defined, and a set of distinct oligonucleotides are synthesized such that each contain a different index sequence. Index sequences are long enough to uniquely distinguish them from one another, or long enough to uniquely distinguish them even if one or more errors are made during sequencing. In some aspects, typical lengths for the index sequence are 2-8 bases. In some aspects, the index sequence is located to one side or the other of the degenerate barcode region, between the two priming regions, and is read along with the barcode in a single or a paired-end read. In other aspects, the index sequence is 5' of the sequencing primer region in the synthesized oligonucleotide and 3' of an additional sequence that anneals to oligonucleotides attached to the sequencing flowcell (or that anneals to a primer that adds such a sequence during PCR). In this aspect, the adapter is designed to mimic the structure of a sequencing-ready molecule, and the index is read by a separate index read on a sequencing machine (e.g., Illumina).

In some aspects, as an alternative to downstream linkage of two distinct barcode sequences ligated to the two ends of the target molecule, both ends of the target molecule are tagged with the same barcode sequence.

In some aspects, a single circularization barcode adapter is ligated to the target molecule in lieu of two end adapters. In some aspects, the two ends of this adapter ligate to the two ends of the same target molecule to form a circular molecule.

In some aspects, the adapter contains a single barcode sequence, which is flanked in the 5' direction on each strand by uracil bases (see FIG. 5). In some aspects, after circularization, the USER™ enzyme mix (Uracil-Specific Excision Reagent) Enzyme (NEB) excises uracils and breaks the phosphate backbone. The term "USER enzyme" as used herein refers to USER™ (NEB), which is a mixture of Uracil DNA glycosylase (UDG) and the DNA glycosylase-lyase Endonuclease VIII. UDG catalyzes the excision of a uracil base, forming an abasic (apyrimidinic) site while leaving the phosphodiester backbone intact. The lyase activity of Endonuclease VIII breaks the phosphodiester backbone at the 3' and 5' sides of the abasic site so that base-free deoxyribose is released. Each strand is thereby broken 5' of the barcode sequence, opening the circular molecule into a linear molecule with 5' single-stranded overhangs at each end that contain the same barcode sequence. In some aspects, extension of the 3' ends by, e.g., Klenow exo-DNA polymerase copies the barcode sequence at each end, creating a fully double-stranded DNA molecule with the same barcode sequence at both ends. Klenow exo-DNA polymerase extension also leaves single dA-tails useful for ligating additional adapters containing sequences that serve as PCR primer annealing sites for subsequent PCR amplification.

In some aspects, a single circularizing adapter that contains two double-stranded copies of the same barcode sequence is ligated to the target molecule (see FIG. 6). In some aspects, such an adapter is prepared by synthesizing an oligonucleotide containing a degenerate barcode region and a region that forms a self-priming hairpin, extending the self-primed 3' end with DNA polymerase, nicking the newly double-stranded molecule with a nicking endonuclease at a site near the 5' end of the original oligonucleotide, and extending the exposed 3' end with a strand-displacing DNA polymerase. In some aspects, after circularizing ligation to a target molecule, the adapter is cut at a specific site between the two copies of the barcode by a restriction enzyme or a combination of USER enzyme and a nuclease that specifically digests single-stranded DNA, such as S1 nuclease or mung bean nuclease.

In some aspects, an adapter comprising two copies of the same barcode is used. After circularization around the adapter, USER enzyme or another nuclease breaks the adapter between the barcode copies, yielding a linear molecule with the same barcode at both ends. A schematic of this approach is set out in FIG. 6. In some aspects, simultaneous fragmentation and adapter addition are carried out. In particular aspects, this simultaneous process is carried out by the use of transposases, which are discussed herein below in more detail.

In some aspects, adapter oligonucleotides are any suitable length. In some aspects, the length of the adapter is at least sufficient to accommodate the one or more sequence elements of which the adapter comprises. In some aspects, adapters are about, less than about, or more than about 10, about 15, about 20, about 25, about 30, about 35, about 40, about 45, about 50, about 55, about 60, about 65, about 70, about 75, about 80, about 90, about 100, about 120, about 140, about 160, about 180, about 200, about 300, about 400, about 500, about 600, about 700, about 800, about 900, or more nucleotides in length. In more particular aspects, adapters are 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length.

Adapter attachment can be carried out in any suitable manner. In some aspects, an adapter is attached to each end of each member of the target library. In some aspects, an adapter is attached to only one end of each member of the target library. In some aspects, an adapter is attached to the nucleic acid following end-repair and any of dT-tailing, dA-tailing, dG-tailing, or dC-tailing. Tailing can be performed by Klenow exo⁻ polymerase or Taq polymerase to add a single tailing nucleotide, or by terminal transferase to add multiple tailing nucleotides. In some aspects, the adapter is attached by ligation. The term "ligation" as used herein, with respect to two polynucleotides, refers to the covalent attachment or joining of two separate polynucleotides to produce a single larger polynucleotide with a contiguous backbone. Methods for joining two polynucleotides include without limitation, enzymatic and non-enzymatic (e.g., chemical) methods. Examples of ligation reactions that are non-enzymatic include the non-enzymatic ligation techniques described in U.S. Pat. Nos. 5,780,613 and 5,476,930, which are herein incorporated by reference. In some embodiments, an adapter oligonucleotide is joined to a target polynucleotide by a ligase, for example a DNA ligase or RNA ligase. Multiple ligases, each having characterized reaction conditions include, without limitation NAD-dependent ligases including tRNA ligase, Taq DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and genetically engineered variants thereof.

In some aspects, an adapter is ligated to each end of each double-stranded fragment of the target library. In particular aspects, a first tripartite adapter comprising an outer PCR primer region, an inner sequencing primer region, and a central barcode region is attached to each end of a short, linear nucleic acid sequence of the fragment library to form multiple barcode-tagged fragments or sequences, wherein the first adapter attached at the one end comprises a different barcode than the first adapter attached at the other end.

In some aspects, the addition of adapters occurs in a mixed solution and does not require physical separation of the nucleic acid in order to add the adapter. Thus, in various aspects, adapters are added to up to a million or more nucleic acids.

In some aspects, ligation is between polynucleotides having hybridizable sequences, such as complementary overhangs. The term "complementary" as used herein refers to a nucleic acid sequence of bases that can form a double-stranded nucleic acid structure by matching base pairs. In some aspects, ligation is between polynucleotides comprising two blunt ends. In some aspects, a 5' phosphate is utilized in a ligation reaction. In some aspects, a 5' phosphate is provided by the target polynucleotide, the adapter oligonucleotide, or both. In some aspects, 5' phosphates are added to or removed from polynucleotides to be joined, as needed. Methods for the addition or removal of 5' phosphates include without limitation enzymatic and chemical processes. Enzymes useful in the addition and/or removal of 5' phosphates include, but are not limited to, kinases, phosphatases, and polymerases.

Nucleic Acid Amplification and Amplification Bias

In some embodiments, adapter-tagged target molecules are amplified using any suitable amplification method. Amplification as used herein refers to production of additional copies of a nucleic acid sequence, and can be carried out using PCR or any other suitable amplification technology (e.g., Dieffenbach and Dveksler, PCR Primer, a Laboratory Manual, Cold Spring Harbor Press, Plainview, N.Y. [1995]). Examples of suitable nucleic acid amplification methods include, but are not limited to, PCR, quantitative PCR, quantitative fluorescent PCR (QF-PCR), multiplex fluorescent PCR (MF-PCR), real time PCR (RTPCR), single cell PCR, restriction fragment length polymorphism PCR (PCR-RFLP), PCK-RFLPIRT-PCR-IRFLP, hot start PCR, nested PCR, in situ polony PCR, in situ rolling circle amplification (RCA), bridge PCR, picotiter PCR, and emulsion PCR. Other suitable amplification methods include, but are not limited to, ligase chain reaction (LCR), transcription amplification, self-sustained sequence replication, selective amplification of target nucleic acids, consensus sequence primed polymerase chain reaction (CP-PCR), arbitrarily primed polymerase chain reaction (AP-PCR), degenerate oligonucleotide-primed PCR (DOP-PCR), and nucleic acid-based sequence amplification (NABSA).

In some aspects, PfuCx Turbo DNA polymerase (Agilent Technologies, La Jolla, Calif.) or KAPA HiFi Uracil+ DNA Polymerase (Kapa Biosystems, Inc., Wilmington, Mass.) is used for PCR. These polymerase enzymes are compatible with uracil-containing primers, yet feature a proofreading activity that reduces the error rate relative to Taq polymerases. In some aspects, polymerase mixtures optimized for "long-range" PCR are used. These polymerase mixtures usually contain a mixture of Taq polymerase with a proofreading polymerase. Examples include LongAmp Taq (NEB) and MasterAmp Extra-long (Epicentre). In some aspects, a single primer is used for PCR. Using a single primer has been shown to discourage the accumulation of primer dimers during PCR. In some other aspects, two or more primers are used for PCR.

In some aspects, PCR bias or "amplification bias" can be a significant challenge when amplifying complex, heterogeneous libraries that result from shearing genomic DNA. In some aspects, each barcode-tagged sequence in the library is amplified to a similar extent. In some aspects, if a subset of the target molecules dominate the PCR, fragments derived from those molecules are sequenced disproportionately frequently, and the yield of the sequencing reaction suffers. In some aspects, while some level of amplification bias is unavoidable, steps are taken to minimize impact of amplification bias. In some aspects, bias is minimized by supplementing the PCR reaction with betaine, DMSO, or other known additive(s), or combinations thereof, to reduce the sequence dependence of amplification efficiency, promoting a more even distribution of amplified products.

In some aspects, PCR suppression effects are minimized. In some aspects, an identical sequence is ligated at both ends of a nucleic acid. In some aspects, upon denaturation during PCR, complementary ends anneal to form a hairpin, potentially reducing the efficiency of PCR. In some aspects, ligating the same adapter to both ends of the target molecule results in identical PCR primer-annealing, and primer-annealing sequences (e.g., Illumina primer-annealing sequences) contribute to PCR suppression hairpins, particularly when the two random barcode sequences in the adapters happen to be partially complementary. To minimize this effect, distinct PCR primer-annealing sequences and/or distinct primer-annealing sequences (e.g., Illumina) are included in the adapters that are attached to the two ends of the target molecule. In various aspects, steps are taken to avoid having identical adapters on both ends of the DNA, because when the DNA becomes single stranded the ends can anneal to form a "panhandle" structure that blocks PCR primer annealing. In some aspects, this addition of primer annealing sequences is accomplished by adding a mixture of different adapters into the ligation mixture (in which case 1/n of the ligation products will have the same adapter on both ends, where n is the number of distinct adapters in the mixture). In other aspects, PCR suppression is promoted by the use of longer adapters in order to suppress amplification of shorter fragments in favor of longer fragments.

In some aspects, a "forked" or "Y" adapter comprising two oligonucleotides that are only partially complementary is used. In some aspects, such oligonucleotides anneal to form an adapter that is double stranded and ligation competent at one end, but forks into two non-complementary single strands at the other end. This type of adapter is often used in standard sequencing methods (e.g., Illumina) and may be used in some aspects of the disclosure. The benefit is that subsequent PCR with primers complementary to the two strands yields products with one of the two fork sequences at one end and the other fork sequence at the other end, which is otherwise not possible at 100% efficiency when ligating adapters to a library of unknown sequences. Standard sequencing protocols (e.g., Illumina) use a mixture of sequencing primers that contains primers compatible with different library preparation kits. Two primer mixtures are used: a "universal" primer mix that produces the first read, and an "index" primer mix that produces the second or paired-end read. Therefore, by ligating two distinct universal primer-annealing sequences or two distinct index primer-annealing sequences to the target, PCR suppression hairpins can be avoided while preserving the ability of fragments derived from each end to be sequenced with the same standard (e.g., Illumina) primer mixture.

In some additional aspects, amplification bias is reduced by a linear amplification stage prior to exponential amplification (see FIG. 4). During the linear PCR amplification phase, only the initially present (original) molecules, and not the newly synthesized copies, are copied by PCR. In some aspects, the copying of only the original nucleic acid molecules is accomplished by ligating barcode-containing adapters with 3' overhangs to the ends of the target molecule, such that only one of the two strands at each end of the ligated target molecule is capable of annealing to a PCR primer at a set annealing temperature. In some aspects, exponential amplification is triggered by a change in the annealing temperature or the addition of a nested primer.

In some aspects, amplification bias is minimized by replacing PCR with rolling-circle amplification (RCA) or hyperbranching rolling-circle amplification (HRCA). HRCA has been used in whole-genome amplification techniques and has been shown to amplify mixed populations with less bias than PCR. In some aspects, a circularization adapter is ligated to the target, such that the two ends of the adapter ligate to the ends of the same target molecule to form a circular molecule. In some aspects, the adapter contains a single barcode sequence, which is flanked in the 5' direction on each strand by nicking endonuclease recognition sequences. In some aspects, after circularization, HRCA amplifies the molecule in an exponential manner. In some aspects, the resulting double-stranded DNA concatamers are broken, such as, for example, by mechanical shearing or dsDNA fragmentase. In some aspects, the nucleic acids are then treated with a nicking endonuclease, which introduces single-strand breaks on each side of the barcode. In some aspects, each strand of the barcoded section becomes a 5' overhang at the end of the resulting fragments, and Klenow or another polymerase is used to fill in these ends, copying the barcode to create a blunt end ready for circularization.

In some aspects, two loop adapters are ligated to the ends of the target to create a circular "dumbbell" structure that is amplified by HRCA. The resulting concatamers are sheared and digested by a nicking endonuclease.

In some aspects, in place of mechanical or enzymatic fragmentation, random fragments are generated during amplification by PCR or rolling-circle amplification with random (degenerate) or partially random oligonucleotide primers (e.g., see FIG. 8A and FIG. 8B).

In some aspects, interior regions of the amplified target molecule are exposed prior to circularization by fragmentation using a double-stranded DNA fragmentase enzyme mixture (NEB). This enzyme mixture is a mixture of two enzymes that creates random breaks in double-stranded DNA. In some aspects, KAPA Frag Enzyme is used for fragmentation. Unlike exonucleases, fragmentation enzymes preserve both ends of the DNA molecule, both of which give rise to productive circular molecules. Unlike mechanical shearing, fragmentation enzymes introduce breaks along the length of the DNA molecule independent of the distance from an end of the molecule or independent of the size of the molecule. Additionally, in some aspects, the number of breaks per kilobase is adjusted for different target molecule lengths by diluting the enzyme mixture or adjusting the reaction time. Typically, reaction time takes about 15 minutes, but is adjusted accordingly, in various aspects, depending on the amount of DNA, the length of the DNA (e.g., the goal is one break per molecule, regardless of its length), and the concentration of the enzyme.

In some aspects, adapter-tagged target molecules are amplified by PCR using a single, uracil-containing oligonucleotide primer that is complementary to a constant region of the adapter lying outside of the barcode sequence, such that the barcode is copied by the extension of the primer. In some aspects, amplification creates many copies of each target molecule such that each copy of the same target molecule is attached to the same barcode sequence unique to that target molecule. In some aspects, the PCR primer sequence is removed from the end of each nucleic acid target molecule. In some other aspects, the PCR primer sequence is removed by digestion with a USER enzyme, followed by end blunting with Klenow fragment polymerase and/or T4 DNA polymerase.

In some aspects, amplified copies of the target molecules are randomly fragmented to create molecules with a barcode sequence at one end and a region of unknown sequence at the other end. In some aspects, the fragmented nucleic acid molecules are end-repaired to create blunt ends. In some aspects, biotinylated nucleotides are incorporated into the repaired ends. In some aspects, the fragmented nucleic acid molecules are circularized. In some aspects, circularizing the fragmented molecules is carried out by blunt-end ligation to bring the barcode sequence into proximity with the unknown region of sequence from the interior of the original target molecule. In some aspects, the circularized molecules are fragmented to create linear molecules. In some aspects, biotinylated molecules are attached to streptavidin-coated beads to facilitate handling and purification. In some aspects, an asymmetric adapter is ligated to each end of the linear molecules.

In some aspects, adapter-ligated fragments are amplified or copied. In some aspects, amplification is carried out by PCR using two oligonucleotide primers, the first of which is complementary to a constant sequence from the barcode-containing adapter, and the second of which is complementary to the overhanging sequence of the asymmetric adapter, and which together add sequences necessary for sequencing.

Circularization and Fragmentation

In some aspects, fragmented nucleic acids are circularized. Circularization of a nucleic acid can be carried out in any suitable manner. In some aspects, circularization is carried out by blunt-end ligation. In some aspects, this approach is used to minimize the intervening sequence between the barcode sequence and the unknown sequence region. In various aspects, sequencing such intervening sequence(s) in every sequencing read wastes capacity and decreases efficiency. In some aspects, the efficiency of blunt-end ligation circularization is low, particularly for long DNA molecules. In some aspects, circularization efficiency is improved, including by the use of a bridging oligonucleotide or adapter, by the creation of complementary sticky ends at the ends of the fragment, or by the use of recombinases (Peng et al., PLoS One 7(1): e29437, 2012).

In some aspects, a circularization adapter is used to circularize fragmented PCR copies that already have been barcoded. In some aspects, the circularized molecule is amplified by PCR. In some aspects, the circularized molecule is amplified by RCA.

In some aspects, barcode-tagged fragments comprising the barcode region at one end and a region of unknown sequence from an interior portion of the target nucleotide sequence at the other end are circularized, thereby bringing the barcode region into proximity with the region of unknown sequence.

Fragmentation (or fragmenting) of nucleic acid molecules is carried out in various aspects of the disclosure. For example, in some aspects, the methods of the disclosure comprise multiple fragmenting steps. Fragmenting of nucleic acids can be carried out by any suitable method. In some aspects, the circularized, barcode-tagged nucleic acid molecules are fragmented into linear fragments, some of which contain barcodes.

In some aspects, fragmenting of the circularized molecules is carried out by an acoustic shearing device (e.g., Covaris S2), and/or by Nextera™ transposases (Epicentre, Madison, Wis.) to combine shearing and the addition of asymmetric adapters. In some aspects, transposase technology, such as that used in the Nextera™ system (Epicentre), streamlines processing because transposases simultaneously fragment DNA and introduce adapter sequences at the newly exposed ends. Thus, transposases, in various aspects, replace fragmentation or shearing, end repair, end tailing, and adapter ligation with a single step. In some aspects, therefore, transposases are used in fragmentation. For example, in some aspects, transposes are used, e.g., for (1) fragmentation of genomic or other extremely large DNA molecules into target fragments 1-20 kb in length with concomitant attachment of tripartite adapters; (2) fragmentation of long target fragments with optional concomitant attachment of adapters designed to improve circularization efficiency; and (3) fragmentation of circularized DNA with concomitant attachment of asymmetric adapters. Accordingly, in some aspects, transposases are used to decrease the time necessary to prepare DNA samples for sequencing.

Sequencing and Sequence Assembly

Various embodiments described herein relate to methods using high-throughput sequencing. In some aspects, the term "bulk sequencing," "massively parallel sequencing," or "next-generation sequencing (NGS)" refers to any high-throughput sequencing technology that parallelizes the DNA sequencing process. For example, in some aspects, bulk sequencing methods are typically capable of producing more than one million nucleic acid sequence reads in a single assay. In some aspects, the terms "bulk sequencing," "massively parallel sequencing," and "NGS" refer only to general methods, not necessarily to the acquisition of greater than one million sequence tags in a single run.

In some aspects, sequencing is carried out on any suitable sequencing platform, such as reversible terminator chemistry (e.g., Illumina), pyrosequencing using polony emulsion droplets, e.g., 454 sequencing (e.g., Roche), ion semiconductor sequencing (Ion Torrent™, Life Technologies), single molecule sequencing (e.g., SMRT, Pacific Biosciences, Menlo Park, Calif.), SOLiD sequencing (Applied Biosystems), massively parallel signature sequencing, and the like.

Various embodiments described herein relate to methods of generating overlapping sequence reads and assembling them into a contiguous nucleotide sequence ("contig") of a nucleic acid of interest. In some aspects, assembly algorithms align and merge overlapping sequence reads generated by methods described herein to provide a contiguous sequence of a nucleic acid of interest. In some aspects, nucleic acid sequence reads sharing the same barcode sequences are identified and grouped. In some aspects, each group of reads (i.e., grouped by a shared barcode sequence) is assembled into one or more longer contiguous sequences.

In some aspects, grouping of sequences is carried out by a computer program. For example, in various aspects, numerous sequence assembly algorithms or sequence assemblers are utilized, taking into account the type and complexity of the nucleic acid of interest to be sequenced (e.g., genomic DNA, PCR product, plasmid, and the like), the number and/or length of nucleic acids or other overlapping regions generated, the type of sequencing methodology performed, the read lengths generated, whether assembly is de novo assembly of a previously unknown sequence or mapping assembly against a reference sequence, and the like. In additional aspects, an appropriate data analysis tool is selected based on the function desired, such as alignment of sequence reads, base-calling and/or polymorphism detection, de novo assembly, assembly from paired or unpaired reads, or genome browsing and annotation.

In some aspects, overlapping sequence reads are assembled into contigs or the full or partial contiguous sequence of the nucleic acid of interest by sequence alignment, computationally or manually, whether by pairwise alignment or multiple sequence alignment of overlapping sequence reads.

In some aspects, overlapping sequence reads are assembled by sequence assemblers including, but not limited to ABySS, AMOS, Arachne WGA, CAP3, PCAP, Celera WGA Assembler/CABOG, CLC Genomics Workbench, CodonCode Aligner, Euler, Euler-sr, Forge, Geneious, MIRA, miraEST, NextGENe, Newbler, Phrap, TIGR Assembler, Sequencher, SeqMan NGen, SHARCGS, SSAKE, Staden gap4 package, VCAKE, Phusion assembler, Quality Value Guided SRA (QSRA), Velvet (algorithm) (Zerbino et al., Genome Res. 18(5): 821-9, 2008), SPAdes, and the like.

In certain aspects, algorithms suited for short-read sequence data may be used including, but not limited to, Cross_match, ELAND, Exonerate, MAQ, Mosaik, RMAP, SHRiMP, SOAP, SSAHA2, SXOligoSearch, ALLPATHS, Edena, Euler-SR, SHARCGS, SHRAP, SSAKE, VCAKE, Velvet, PyroBayes, PbShort, and ssahaSNP.

In some aspects, the methods provided herein provide for the assembly of a contig or full continuous sequence of the nucleic acid of interest at lengths in excess of about 1 kb, about 2 kb, about 3 kb, about 4 kb, about 5 kb, about 6 kb, about 7 kb, about 8 kb, about 9 kb, about 10 kb, about 11 kb, about 12 kb, about 13 kb, about 14 kb, about 15 kb, about 16 kb, about 17 kb, about 18 kb, about 19 kb, about 20 kb, about 25 kb, about 30 kb, about 35 kb, about 40 kb, about 45 kb, or about 50 kb. In certain aspects, the methods provided herein provide for the assembly of a target nucleic acid with a length of about 0.1 kb, about 0.2 kb, about 0.3 kb, about 0.4 kb, about 0.5 kb, about 0.6 kb, about 0.7 kb, about 0.8 kb, about 0.9 kb, about 1.0 kb, about 1.1 kb, about 1.2 kb, about 1.3 kb, about 1.4 kb, about 1.5 kb, about 1.6 kb, about 1.7 kb, about 1.8 kb, about 2.0 kb, about 2.1 kb, about 2.2 kb, about 2.3 kb, about 2.4 kb, about 2.5 kb, about 2.6 kb, about 2.7 kb, about 2.8 kb, about 2.9 kb, about 3.0 kb, about 3.1 kb, about 3.2 kb, about 3.3 kb, about 3.4 kb, about 3.5 kb, about 3.6 kb, about 3.7 kb, about 3.8 kb, about 3.9 kb, about 4.0 kb, about 4.1 kb, about 4.2 kb, about 4.3 kb, about 4.4 kb, about 4.5 kb, about 4.6 kb, about 4.7 kb, about 4.8 kb, about 4.9 kb, about 5.0 kb, about 5.2 kb, about 5.3 kb, about 5.4 kb, about 5.5 kb, about 5.6 kb, about 5.7 kb, about 5.8 kb, about 5.9 kb, about 6.0 kb, about 6.1 kb, about 6.2 kb, about 6.3 kb, about 6.4 kb, about 6.5 kb, about 6.6 kb, about 6.7 kb, about 6.8 kb, about 6.9 kb, about 7.0 kb, about 7.1 kb, about 7.2 kb, about 7.3 kb, about 7.4 kb, about 7.5 kb, about 7.6 kb, about 7.7 kb, about 7.8 kb, about 7.9 kb, about 8.0 kb, about 8.1 kb, about 8.2 kb, about 8.3 kb, about 8.4 kb, about 8.5 kb, about 8.6 kb, about 8.7 kb, about 8.8 kb, about 8.9 kb, about 9.0 kb, about 9.1 kb, about 9.2 kb, about 9.3 kb, about 9.4 kb, about 9.5 kb, about 9.6 kb, about 9.7 kb, about 9.8 kb, about 9.9 kb, about 10.0 kb, about 10.5 kb, about 11.0 kb, about 11.5 kb, about 12.0 kb, about 12.5 kb, about 13.0 kb, about 13.5 kb, about 14.0 kb, about 14.5 kb, about 15.0 kb, about 15.5 kb, about 16.0 kb, about 16.5 kb, about 17.0 kb, about 17.5 kb, about 18.0 kb, about 18.5 kb, about 19.0 kb, about 19.5 kb, about 20.0 kb, about 20.5 kb, about 21.0 kb, about 21.5 kb, about 22.0 kb, about 22.5 kb, about 23.0 kb, about 23.5 kb, about 24.0 kb, about 24.5 kb, about 25.0 kb, about 30.0 kb, about 35.0 kb, about 40.0 kb, about 45.0 kb, about 50.0 kb, about 55.0 kb, about 60.0 kb, about 65.0 kb, about 70.0 kb, about 75.0 kb, about 80.0 kb, about 85.0 kb, about 90.0 kb, about 95.0 kb, or about 100 kb, or greater.

Alternatively, in some aspects, the methods provided herein provide for the assembly of a contig or full continuous sequence of the nucleic acid of interest at lengths of less than about 1 kb, about 900 bp, about 800 bp, about 700 bp, about 600 bp, or about 500 bp, or lesser.

In some aspects, the methods provided herein provide for the assembly of a contig or full continuous sequence of the nucleic acid of interest with very high per base accuracy or fidelity. The term "accuracy" or "fidelity" as used herein refers to the degree to which the measurement conforms to the correct, actual, or true value of the measurement. For example, in some aspects, accuracy or fidelity of the disclosed method is greater than about 80%, about 90%, about 95%, about 99%, about 99.5%, about 99.9%, about 99.95%, about 99.99%, about 99.999%, or greater. In some aspects, sequencing errors affecting per base and average accuracy of sequence information due to the underlying sequencing platform are substantially or completely corrected by majority calls by the assembly methods and systems described herein, e.g., such as a computer acting as an assembler. In some aspects, an output with a single long read is produced from putting together multiple long reads.

In particular aspects, the methods provided herein provide for the assembly of the nucleic acid of interest with about 100% accuracy, about 99.99% accuracy, about 99.98% accuracy, about 99.97% accuracy, about 99.96% accuracy, about 99.95% accuracy, about 99.94% accuracy, about 99.93% accuracy, about 99.92% accuracy, about 99.91% accuracy, about 99.90% accuracy, about 98.99% accuracy, about 98.98% accuracy, about 98.97% accuracy, about 98.96% accuracy, about 98.95% accuracy, about 98.94% accuracy, about 98.93% accuracy, about 98.92% accuracy, about 98.91% accuracy, about 98.90% accuracy, about 98.89% accuracy, about 98.88% accuracy, about 98.87% accuracy, about 98.86% accuracy, about 98.85% accuracy, about 98.84% accuracy, about 98.83% accuracy, about 98.82% accuracy, about 98.81% accuracy, about 98.80% accuracy, about 98.79% accuracy, about 98.78% accuracy, about 98.77% accuracy, about 98.76% accuracy, about 98.75% accuracy, about 98.74% accuracy, about 98.73% accuracy, about 98.72% accuracy, about 98.71% accuracy, about 98.70% accuracy, about 98.69% accuracy, about 98.68% accuracy, about 98.67% accuracy, about 98.66% accuracy, about 98.65% accuracy, about 98.64% accuracy, about 98.63% accuracy, about 98.62% accuracy, about 98.61% accuracy, about 98.60% accuracy, about 98.5% accuracy, about 98.0% accuracy, about 97.5% accuracy, about 97.0% accuracy, about 96.5% accuracy, about 96.0% accuracy, about 95.5% accuracy, about 95.0% accuracy, about 94.5% accuracy, about 94.0% accuracy, about 93.5% accuracy, about 93.0% accuracy, about 92.5% accuracy, about 92.0% accuracy, about 91.5% accuracy, about 91.0% accuracy, about 90.5% accuracy, about 90.0% accuracy, about 89.% accuracy, about 88% accuracy, about 87% accuracy, about 86% accuracy, about 85% accuracy, about 84% accuracy, about 83% accuracy, about 82% accuracy, about 81% accuracy, or about 80% accuracy.

In some aspects, the methods provided herein provide for the assembly of a contig or full continuous sequence of the nucleic acid of interest with an error rate of about 0.001%, about 0.002%, about 0.003%, about 0.004%, about 0.005%, about 0.006%, about 0.007%, about 0.008%, about 0.009%, about 0.010%, about 0.011%, about 0.012%, about 0.013%, about 0.014%, about 0.015%, about 0.016%, about 0.017%, about 0.018%, about 0.019%, about 0.020%, about 0.025%, about 0.030%, about 0.035%, about 0.040%, about 0.045%, about 0.050%, about 0.055%, about 0.060%, about 0.065%, about 0.070%, about 0.075%, about 0.080%, about 0.085%, about 0.090%, about 0.095%, about 0.10%, about 0.15%, about 0.20%, about 0.25%, about 0.30%, about 0.35%, about 0.40%, about 0.45%, about 0.50%, about 0.55%, about 0.60%, about 0.65%, about 0.70%, about 0.75%, about 0.80%, about 0.85%, about 0.90%, about 0.95%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.5%, about 6.0%, about 6.5%, about 7.0%, about 7.5%, about 8.0%, about 8.5%, about 9.0%, about 9.5%, about 10.0%, about 15%, or about 20%.

In some aspects, the methods described herein take less than 5 days, less than 4 days, less than 3 days, less than 2 days, or less than 1 day. In particular aspects, methods described herein take about 3 days, because the methods comprise elements that run overnight (i.e., PCR amplification and ligation). In some aspects, methods are shortened (or sped up) by the use of faster PCR thermocyclers and faster polymerases, and/or by using higher concentrations of ligase. Such improvements, in some aspects, shorten the protocol to two days. Further improvements, including the use of Nextera™ transposon, as described herein above, also eliminates protocol components, speeds up the protocol, and shortens overall method time.

In some aspects, the methods described herein are much simpler and more convenient than other methods. For example, in some aspects, the methods of the disclosure are carried out in a single tube, thus involving less handling, and eliminating the need to split the library into multiple-well plates.

In some aspects, the methods of the disclosure facilitate haplotyping of chromosomes of polyploid species. A haplotype is a collection of specific alleles (e.g., particular DNA sequences) in a cluster of tightly-linked genes on a chromosome that are likely to be inherited together. In other words, a haplotype is the group of genes that a progeny inherits from one parent. A cell or a species is "polyploid" if it contains more than two haploid (n) sets of chromosomes. In other words, the chromosome number for the cell or species is some multiple of n greater than the 2n content of diploid cells. For example, triploid (3n) and tetraploid cell (4n) cells are polyploid. In some aspects, the methods of the disclosure are useful in haplotype reconstruction from sequence data, or by haplotype assembly.

Methods of the Disclosure

For example, in one example embodiment, fragments of nucleic acid are assembled into distinct nucleic acid sequences by fragmenting a target nucleic acid molecule and attaching the same random nucleic acid barcode to each short sequencing-ready nucleic acid fragment that derives from the nucleic acid molecule. To each end of each fragment in the starting library is ligated a first "tripartite" adapter comprising an outer PCR annealing region, a central random barcode sequence, and an inner sequencing primer region. The adapter-ligated library is then diluted, and about one million molecules (or more or fewer) are amplified by PCR using a primer complementary to the PCR annealing region on the adapter. In various aspects, the library is diluted by orders of magnitude greater or lesser than the million molecules, depending on the goal of the sequencing and the resources available. For example, the complexity depends upon the amount of sequencing and the length of the target. In some aspects, about 10,000 or more molecules are amplified; whereas, in some aspects about 1,000,000 or more molecules are amplified. In some aspects, dilution of the library ensures that enough reads are derived from each molecule to allow full assembly. Each of the about one million library sequences is copied many times with PCR. The PCR annealing region is removed from each 5' end of the amplified nucleic acid with USER™ enzyme, which cuts the DNA backbone at uracil bases designed into the PCR primer. The barcode sequences are thus positioned at the ends of each molecule. An enzyme mixture called dsDNA fragmentase is then used to randomly cut each copy in a different location. The ends of the nucleic acid are repaired (blunted) in the presence of biotin-dCTP, which results in biotinylation of the ends of the nucleic acid molecules. In some aspects, dC nucleotides are designed into the tripartite adapter to ensure successful biotinylation. The nucleic acid is then circularized, bringing the barcode sequence at one end into proximity with an unknown sequence region randomly selected from the length of the starting molecule. The circularized nucleic acid is again fragmented, this time by shearing (including, in some aspects, mechanical or acoustic shearing), to obtain molecules of a desired length. In some aspects, the desired nucleic acid length is about 300 bp to about 800 bp, but this may be modified depending on the sequencing instrument used and the goals of the sequencing. In some aspects, the nucleic acid fragments containing the barcodes are bound to streptavidin-coated magnetic beads, end-repaired, dA-tailed, and ligated to another adapter. This "second" adapter comprises two oligonucleotides of different lengths, such that when annealed the shorter oligonucleotide has a 3' dT overhang and the longer oligonucleotide, which corresponds to a second sequencing primer annealing sequence, has a longer 3' overhang. In some aspects, only the longer oligonucleotide (and not the subsequently synthesized reverse complement of the shorter adapter) is able to subsequently anneal to the PCR primer. The beads are added to a PCR mixture containing primers that anneal to the two sequencing primer regions (one of which was added by the first adapter, the other by the second adapter). PCR exponentially amplifies only the region of the template from the first sequencing primer, in the direction of the barcode and the sequence of interest, through the second adapter, and adds sequences that allow annealing to the sequencing flow cell. In some aspects, the resulting nucleic acid molecules are size-selected. In some aspects, size selection and, therefore, tighter size distribution leads to better sequencing results.

If size selected, the size selection is carried out by the Agencourt AMPure XP system (Beckman Coulter, Brea, Calif.), or by gel purification. The nucleic acid molecules are then sequenced, using a single-end read or paired-end reads. The sequencing data from the first read contains the barcode sequence followed by sequence from the original fragment. In some aspects, it also is possible to switch the method so that the barcode is on the second read. All sequences with identical barcodes are grouped, and each group is assembled into the full-length sequence independent of the others. In various aspects, this method is adapted for use on any of the available high-throughput sequencing platforms.

In a further aspect, the embodiment outlined above generates two barcode-defined groups of reads corresponding to each original target molecule, defined by the two distinct barcode sequences in the adapters that are ligated to the two ends of the target molecule. Each target molecule is thus "tagged" with two different barcode sequences. Fragments containing one of the two barcode sequences are pooled and assembled separately from those containing the other barcode sequence. In some aspects, the two barcode sequences are linked by a supplemental experimental preparation and/or computational analysis, allowing all reads containing either of the barcode sequences to be pooled and assembled together. In some aspects, the length of the target molecules that are sequenced is thereby doubled, the efficiency of the method is increased, and the problem of decreasing circularization efficiency with increasing molecule length is partially offset. In some aspects, a subset of the PCR-amplified, barcode adapter-ligated target molecules is not fragmented. In some aspects, a subset is physically separated from the fragmented population, and this separated fraction is not subjected to fragmentation. In other aspects, fragmentation of the population is incomplete, and those molecules that escape fragmentation are used for barcode linking. In some aspects, circularization of intact molecules brings the two barcode sequences ligated to that target molecule into proximity. In some aspects, the region containing the two barcode sequences is separated from the target molecule by PCR or restriction endonuclease digestion, converted into sequencing-ready molecules by the addition of appropriate adapter sequences, and sequenced in the same sequencing run as the main library or in a separate run. In the bioinformatic processing pipeline, these linked barcode sequence pairs are identified, and groups of reads tagged with each of the barcode sequences are merged into a single group for assembly into the longer sequence.

In some aspects of the methods described herein, barcode sequences are linked. In some aspects, the linked barcode sequences allow the two barcode-defined groups of reads to be merged by circularizing a small percentage of the products of the first PCR amplification while forgoing fragmentation, such that the barcode sequences at each end are brought into proximity with one another. In some aspects, the circularized full-length molecules remain in the same mixture as the circularized fragmented molecules. In some aspects, both types of molecule are processed together and sequenced in the same sequencing reaction. In various aspects, sequencing reads capturing paired barcode sequences are identified computationally. In some aspects, when this approach is used, it is desirable to use a mixture of tripartite adapters containing distinct sequencing primer regions to avoid hairpin formation. Alternatively, forked adapters are used so that the two ends of the target molecules receive different sequencing primer sequences. In some aspects, a portion of the circularized mixture is removed (before or after fragmentation) and used to prepare samples for barcode pairing. In some aspects, the circularized molecules (which may or may not have previously been fragmented to open the circles) are digested with a restriction endonuclease that recognizes a specific site in the constant regions of the barcode adapter (e.g., in one aspect, the restriction endonuclease SapI recognizes a site in the sequence of the Illumina TruSeq adapter sequence). In some aspects, asymmetric adapters are ligated to the newly exposed sticky end or ends. In some aspects, the adapter-ligated fragments are amplified by PCR using two oligonucleotide primers, the first of which is complementary to a constant sequence from the barcode-containing adapter, and the second of which is complementary to the overhanging sequence of the asymmetric adapter, and which together add sequences for sequencing on a sequencing instrument (e.g., Illumina). In some aspects, forked or Y-shaped adapters are ligated to the newly exposed end or ends. In some aspects, the adapter-ligated fragments are amplified by PCR using two oligonucleotide primers, one of which is complementary to a sequence on one fork of the adapter and the other of which is complementary to a sequence on the second fork of the adapter. The type of adapters used depends on what barcode adapter design is used. In some aspects, the two barcode sequences are identified in the sequencing data. In some aspects, the two groups of reads in the primary sequencing data set defined by each of the linked barcodes are merged and assembled into longer sequences. In most aspects, the short constant sequences bordering the barcodes identify true barcode pairs from spurious sequences.

In a particular aspect, the disclosure provides a method for obtaining nucleic acid sequence information from a nucleic acid molecule by assembling a series of short nucleic acid sequences into longer nucleic acid sequences (i.e. intermediate or long nucleic acid sequences). In most aspects, the method comprises some, if not all, of fragmenting the nucleic acid molecule comprising a nucleic acid sequence or a genomic nucleic acid sequence into a plurality of linear nucleic acid sequences; attaching a first adapter to the linear nucleic acid sequence, the first adapter comprising an outer polymerase chain reaction (PCR) primer region (or nucleic acid amplification region), an inner sequencing primer region, and a central barcode region to each end of the linear nucleic acid sequences to form barcode-tagged sequences, wherein the first adapter attached at one end comprises a different barcode than the first adapter attached at the other end; replicating the barcode-tagged sequences, e.g., by PCR, to obtain a library of barcode-tagged sequences using a primer complementary to the PCR primer region; removing the PCR primer region from the barcode-tagged sequences; breaking the barcode-tagged sequences at random locations using an enzyme that generates linear, barcode-tagged fragments comprising the barcode region at one end and a region of unknown sequence at the other end; circularizing the linear, barcode-tagged fragments comprising the barcode region at one end and a region of unknown sequence from an interior portion of the target nucleotide sequence at the other end, thereby bringing the barcode region into proximity with the region of unknown sequence; fragmenting the circularized, barcode-tagged fragments into linear, barcode-tagged fragments; attaching a second adapter comprising two oligonucleotides of different lengths to each end of the linear, barcode-tagged fragments to form double adapter-ligated barcode-tagged nucleic acid fragments, wherein one end of the second adapter is double stranded to facilitate ligation and the other end of the second adapter comprises a 3' single-stranded overhang, and wherein only the longer of the two oligonucleotides comprises a sequence complementary to a second sequencing primer and comprises sufficient length to allow annealing of that primer; replicating the double adapter-ligated barcode-tagged nucleic acid fragments by PCR using two primers, the first of which is complementary to a constant sequence from the barcode-containing adapter, and the second of which is complementary to the overhanging sequence of the asymmetric adapter, and which together add sequences necessary for nucleic acid sequencing; sequencing the double adapter-ligated barcode-tagged nucleic acid fragments beginning with the barcode region followed by the target sequence; sorting a series of sequenced nucleic acid fragments into independent groups based on shared barcodes; and assembling each group of short nucleic acids into one or more longer nucleic acid sequences, independent of all other groups.

Sample Preparation

In some example aspects of the disclosure, nucleic acid samples are prepared as described below. Only one strand of the nucleic acid is described and set out below.

(1) A tripartite adapter is ligated to the end of the target molecule:

Ligated target-
NNNCCTACACGACGCTCTTCCGATCTNNNNNNNNNNNNNNNNNCCAGGAAT

AGTTATGTGCATTAATGAATGGCGCC (SEQ ID NO: 1)

(2) Target molecules with adapters at both ends are amplified and the PCR primer annealing region (i.e., the region after " . . . NNNNCC") is removed:

Ligated target-
NNNCCTACACGACGCTCTTCCGATCTNNNNNNNNNNNNNNNNNCC (SEQ ID NO: 2)

(3) Amplified target molecules are fragmented and circularized:

Ligated target end-
NNNCCTACACGACGCTCTTCCGATCTNNNNNNNNNNNNNNNNNCC (SEQ ID NO: 2)-ligated region of interest (4) Circularized DNA is fragmented and fragments containing adapter sequences are prepared for sequencing:

Adapter 1 (e.g., Illumina)-
CCTACACGACGCTCTTCCGATCTNNNNNNNNNNNNNNNNNCC (SEQ ID NO: 3)-ligated region of interest-
Adapter 2 (e.g., Illumina)

(5) Resulting sequencing read:
NNNNNNNNNNNNNNNNNCC—ligated region of interest (6) In the computational pipeline, the sequences at the start of the read are used to determine the sample and target molecule of origin:
NNNNNNNNNNNNNNNNNCC—ligated region of interest The 5' multiple N region determines the target molecule of origin. The "CC" region confirms the upstream sequence is a barcode. The 3' region contains sequence information for the ligated region of interest.

Sample Preparation for Barcode Pairing

In some aspects, samples are prepared for barcode pairing as described below. Only one strand of the nucleic acid is described and set out below.

(1) Tripartite adapter is ligated to the end of the target molecule:

(SEQ ID NO: 1)
Ligated target-
NNNCCTACACGACGCTCTTCCGATCTNNNNNNNNNNNNNNNNNCCAGGAA

TAGTTATGTGCATTAATGAATGGCGCC (2) Target molecules with adapters at both ends are amplified and the PCR primer annealing region (i.e., the region after " . . . NNNNCC"):

(SEQ ID NO: 2)
Ligated target-
NNNCCTACACGACGCTCTTCCGATCTNNNNNNNNNNNNNNNNNCC (3) Full-length amplified target molecules that avoid fragmentation are circularized:

Ligated target end-
NNNCCTACACGACGCTCTTCCGATCTNNNNNNNNNNNNNNNNNCC-

GGNNNNNNNNNNNNNNNNNAGATCGGAAGAGCGTCGTGTAGGNNN
(SEQ ID NO: 4)-Ligated target end (4) Circularized DNA is fragmented and fragments containing adapter sequences are prepared for sequencing:

Adapter 1 (e.g. Illumina)-
NNNNNNNNNNNNNNNNNCC-GGNNNNNNNNNNNNNNNN (SEQ ID NO: 5)-Adapter 2 (e.g., Illumina)

(5) Resulting sequencing read:

NNNNNNNNNNNNNNNNNCC-GGNNNNNNNNNNNNNNNN (SEQ ID NO: 5)-Adapter 2 (e.g., Illumina)

(6) In the computational pipeline, the two barcodes (i.e., the multiple "Ns" set out below at each end of the sequence) are identified as a pair:

(SEQ ID NO: 5)
NNNNNNNNNNNNNNNNNCC-GGNNNNNNNNNNNNNNNN

The 5' and 3' multiple N regions represent the paired barcodes.

Multiplexed Sample Preparation

In some aspects, multiplexed samples are prepared as described below. Only one strand of the nucleic acid is described and set out below.

(1) Tripartite adapter is ligated to the end of the target molecule. Underlined, bolded font indicates the index sequence (e.g., ATCACG) unique to each sample:

```
                                              (SEQ ID NO: 6)
Ligated target-
NNNCCTACACGACGCTCTTCCGATCTNNNNNNNNNNNNNNNNNNATCACG

CAGGAATAGTTATGTGCATTAATGAATGGCGCC
```

(2) Target molecules with adapters at both ends are amplified and the PCR primer annealing region (i.e., the region after " . . . NNATCACGC") is removed:

```
                                              (SEQ ID NO: 7)
Ligated target--
NNNCCTACACGACGCTCTTCCGATCTNNNNNNNNNNNNNNNNNNATCACGC
```

(3) PCR products deriving from multiple samples are mixed and processed together in a single tube from this point. Each contains a unique index sequence. Amplified target molecules are fragmented and circularized:

```
Ligated target end-
NNNCCTACACGACGCTCTTCCGATCTNNNNNNNNNNNNNNNNNNATCACGC
(SEQ ID NO: 7)-ligated region of interest
```

(4) Circularized DNA is fragmented and fragments containing adapter sequences are prepared for sequencing:

```
Adapter 1 (e.g., Illumina)-
CCTACACGACGCTCTTCCGATCTNNNNNNNNNNNNNNNNNNATCACGC
(SEQ ID NO: 8)-ligated legion of interest-
Adapter 2 (e.g., Illumina)
```

(5) Resulting sequencing read:

```
    NNNNNNNNNNNNNNNNNNATCACGC
      (SEQ ID NO: 9)-ligated region of interest
```

(6) In the computational pipeline, the sequences at the start of the read are used to determine the sample and target molecule of origin:

```
    NNNNNNNNNNNNNNNNNNATCACGC
      (SEQ ID NO: 9)-ligated region of interest
```

The 5' N region represents the barcode and determines the origin of the target molecule. The "ATCACG" region represents the index sequence and determines origin of the sample. The ligated region of interest contains the sequence information.

Multiplexed Sample Preparation for Barcode Pairing

In some aspects, multiplexed samples are prepared for barcode pairing as described below. Only one strand of the nucleic acid is described and set out below.

(1) Tripartite adapter is ligated to the end of the target molecule. Underlined, bolded font indicates the index sequence (e.g., ATCACG) unique to each sample:

```
                                              (SEQ ID NO: 6)
Ligated target-
NNNCCTACACGACGCTCTTCCGATCTNNNNNNNNNNNNNNNNNNATCACGCA

GGAATAGTTATGTGCATTAATGAATGGCGCC
```

(2) Target molecules with adapters at both ends are amplified and the PCR primer annealing region (i.e., the region after " . . . NNATCACGC") is removed:

```
                                              (SEQ ID NO: 10)
Ligated target--
NNNCCTACACGACGCTCTTCCGATCTNNNNNNNNNNNNNNNNNNATCACGC
```

(3) PCR products deriving from multiple samples are mixed and processed together in a single tube from this point. Each contains a unique index sequence (underlined font). Full-length amplified target molecules that avoid fragmentation are circularized:

```
    Ligated target end--
    NNNCCTACACGACGCTCTTCCGATCTNNNNNNNN

NNNNNNNN ATCACGC-GCGTGATNNNNNNNNN

NNNNNNAGATCGGAAGAGCGTCGTGTAGGNNN
      (SEQ ID NO: 11)-Ligated target end
```

(4) Circularized DNA is fragmented and fragments containing adapter sequences are prepared for sequencing:

```
    Adapter 1 (e.g., Illumina)-
    NNNNNNNNNNNNNNNN ATCACGC-GCGTGAT

NNNNNNNNNNNNNNNN
      (SEQ ID NO: 12)-Adapter 2

(e.g., Illumina)
```

(5) Resulting sequencing read:

```
        NNNNNNNNNNNNNNNNNNATCACGC-

GCGTGATNNNNNNNNNNNNNNNNN- (SEQ ID NO: 12)
```

(6) In the computational pipeline, the two barcodes are identified as a pair and the index determines the sample of origin. Matching indexes confirm intramolecular circularization:

```
NNNNNNNNNNNNNNNNNNATCACGC--GCGTGATNNNNNNNNNNNNNNNNN
(SEQ ID NO: 12)
```

The 5' and 3' multiple N regions represent the paired barcodes. The "ATCACG" region represents the index sequence and determines origin of sample. The "CGTGAT" sequence or region is the reverse complement of the first index sequence, confirming intramolecular circularization.

Computational Pipeline and Sequence Assembly

In some aspects, once a library created according to the methods of the disclosure has been sequenced, the sequencing data is processed to assemble the raw short nucleic acid sequences (or short reads) into synthetic long nucleic acid sequences (long reads). The "computational pipeline" or "processing pipeline" is as described below.

In some aspects, sequencing reads are trimmed to remove regions of low quality, as well as known adapter sequences.

A number of open-source tools are available for this purpose including, but not limited to, Trimmomatic, Skewer the FASTX-toolkit, Scythe and others.

In some aspects, sequencing reads are searched for barcode sequences. In some aspects, the first sixteen bases of the read are identified as a barcode if the subsequent bases match the known constant region in the tripartite adapter, e.g., "CC." The barcode sequence, the constant sequence, and any other adapter sequences (such as sequences left over from incomplete removal of the PCR primer region) are removed from the read. The remainder of the read constitutes sequence information from the molecule identified by the specific barcode. In some aspects, a hash table is created in which the barcode sequences are the keys and the sequence information is the values. That is, each distinct barcode defines a bin, and each sequence read is placed in the bin defined by its barcode. In some aspects, if paired-end reads are used, the reverse read is placed in the same bin as the forward read.

In some aspects, when barcode pairing data is available, those reads are analyzed to find paired barcodes. After trimming adapters and low-quality regions, reads are inspected for the expected pattern, e.g., barcode 1, defined sequence 1, reverse complement of defined sequence 2, reverse complement of barcode 2, and adapter sequence. Barcode pairs are extracted from sequences matching this pattern. In some aspects, a data structure is created to count how many times each barcode is paired with other barcodes. A true pair is verified when two barcodes are paired with each other more times than a threshold number and more times than either is paired with any other barcode. Once a true pair is verified, the sequence read bins corresponding to the two barcodes are merged into a single bin for assembly.

In some aspects, the sequences in each barcode-defined bin are assembled into synthetic long reads. Each bin is assembled independently of the other bins, allowing parallelization of assembly. A number of open-source assemblers are available and are described herein above.

In one aspect, the present disclosure includes a computational pipeline for assembling grouped reads. After quality checking each read for low-confidence calls and for sequences matching the adapters used in the protocol, the first bases can be split from the read and defined as the barcode. In some embodiments, a hash table is built that groups the subset of reads associated with each barcode. In some embodiments, each group is then assembled individually, with or without a reference genome, using standard alignment and assembly software (e.g., Bowtie 2, Velvet, or SPAdes).

In some embodiments, the method is used with nanopore sequencing platforms as described in U.S. Patent Publication Number 2014/0034497, which is herein incorporated by reference in its entirety. In some embodiments, the method is used with Pacific Biosciences sequencing platforms as described in U.S. Pat. No. 7,315,019 and U.S. Pat. No. 8,652,779, which are each herein incorporated by reference in their entirety. In some embodiments, the method is used with Illumina sequencing platforms as described in U.S. Pat. No. 7,115,400 and PCT Publication Number WO/2007/010252, which are incorporated by reference in their entirety. In some embodiments, the method is used with IonTorrent sequencing platforms as described in PCT Patent Publication Number WO/2008/076406, which is herein incorporated by reference in its entirety. In some embodiments, the method is used with Roche/454 sequencing platforms as described in U.S. Patent Number WO/2004/070005, which is herein incorporated by reference in its entirety.

In some embodiments, for which data is provided below as examples, the method comprises the operations of: (a) creating a target nucleic acid library (e.g., by mechanical shearing, PCR, restriction digestion, or another method); (b) preparing that library for adapter attachment (e.g., by end-repair and dT-tailing); (c) creating a mixture of adapter fragments (e.g., comprising regions that are identical among all members of the adapter population and a degenerate "barcode" region that is unique to each member of the population); (d) attaching one adapter to each end of each member of the target library (e.g., by ligation); (e) amplifying the adapter-ligated target molecules by PCR (e.g., using a single, uracil-containing oligonucleotide primer that is complementary to a constant region of the adapters lying 5' of the barcode sequence, to create many copies of each target molecule such that each copy of the same target molecule is attached to the same barcode sequences unique to that target molecule); (f) optionally removing the PCR primer sequence from the 5' end of each DNA strand (e.g., by digestion with USER enzyme); (g) randomly fragmenting the amplified copies of the targets (e.g., to create molecules with a barcode sequence at one end and a region of unknown sequence at the other end); (h) end-repairing the fragmented molecules (e.g., to create blunt ends while incorporating biotinylated nucleotides into the repaired ends); (i) circularizing the fragmented molecules (e.g., by blunt-end ligation to bring the barcode sequence into proximity with the unknown region of sequence from the interior of the original target molecule); (j) fragmenting the circularized molecules (e.g., to create linear molecules); (k) optionally attaching the biotinylated molecules to streptavidin-coated beads (e.g., to facilitate handling and purification); (l) ligating an asymmetric adapter to each end of the linear molecules; (m) amplifying the adapter-ligated fragments (e.g., by PCR using two oligonucleotide primers, the first of which is complementary to a constant sequence from the barcode-containing adapter, and the second of which is complementary to the overhanging sequence of the asymmetric adapter, and which together add sequences necessary for sequencing on a sequencing instrument); (n) sequencing the amplified DNA (e.g., on a massively parallel short-read instrument); (o) computationally identifying and grouping reads sharing the same barcode sequences; and (p) assembling each group of reads (e.g., defined by a shared barcode sequence into longer contiguous sequences describing the original target molecule).

The embodiment outlined above can generate two barcode-defined groups of reads corresponding to each original target molecule (e.g., defined by the two distinct barcode sequences in the adapters that ligated to the two ends of the target molecule). Each target molecule can be tagged with two different barcode sequences. Fragments containing one of the two barcode sequences can be pooled and assembled separately from those containing the other barcode sequence. In some embodiments the two barcode sequences are linked by a supplemental experimental preparation, allowing all reads containing either of the barcode sequences to be pooled and assembled together. In some embodiments, a subset of the PCR-amplified, barcode adapter-ligated target molecules is not fragmented. In some embodiments, this subset is physically separated from the fragmented population, and this separated fraction is not subjected to fragmentation. In some embodiments, fragmentation of the population is incomplete, and those molecules that escape fragmentation are used for barcode linking Circularization of intact molecules brings the two barcode sequences ligated to that target molecule into proximity. In some embodiments, the region containing the two barcode sequences is separated from the target molecule (for example, by PCR or restriction endonuclease digestion), converted into sequencing-ready molecules by the addition of appropriate adapter sequences, and sequenced in the same sequencing run as the main library or in a separate run. In some embodiments, during the bioinformatic processing pipeline, these linked barcode sequence pairs are identified, and groups of reads tagged with each of the barcode sequences are merged into a single group for assembly.

In some embodiments, barcode sequences can be linked as follows: (a) circularizing (a small percentage of) the products of the first PCR amplification while forgoing the fragmentation (e.g., such that the barcode sequences at each end are brought into proximity with one another); (b) digesting the circularized molecules (e.g., with a restriction endonuclease that recognizes a specific site in the constant regions of the barcode adapter (in a some embodiments, the restriction endonuclease SapI recognizes a site in the sequence of the Illumina TruSeq adapter sequences)); (c) ligating asymmetric adapters to the newly exposed sticky end or ends; (d) amplifying the adapter-ligated fragments (e.g., by PCR using two oligonucleotide primers, the first of which is complementary to a constant sequence from the barcode-containing adapter, and the second of which is complementary to the overhanging sequence of the asymmetric adapter, and which together add sequences necessary for sequencing on a sequencing instrument); (e) sequencing the amplified DNA (e.g., on a massively parallel short-read instrument); (f) identifying the two barcode sequences in the sequencing data; and (g) merging the two groups of reads in the primary sequencing data set defined by each of the linked barcodes (e.g., and assembling them together into longer sequences describing the target molecule that barcode adapters containing the two linked barcode sequences were ligated).

In some embodiments, as an alternative to downstream linkage of two distinct barcode sequences ligated to the two ends of the target molecule, both ends of the target molecule are tagged with the same barcode sequence. A single circularization barcode adapter can be ligated to the target molecule in lieu of two end adapters. The two ends of this adapter can ligate to the two ends of the same target molecule to form a circular molecule.

Methods that attach the same barcode sequence to both ends of the target molecule via circularization, including those described herein, have advantages that include: (1) target molecules that escape barcoding can be removed by exonucleases on the basis of remaining linear; and (2) barcoded molecules can be quantified by quantitative PCR (qPCR) by amplifying a short (e.g., 50-100 bp) amplicon corresponding to sequences within the circularization adapter, rather than needing to amplify the entire target molecule.

In some embodiments, the adapter contains a single barcode sequence. In some embodiments, the barcode sequence is flanked in the 5' direction on each strand by uracil bases. After circularization, enzymes (for example, the USER enzyme mix (New England Biolabs)) can excise the uracils and break the phosphate backbone. Each strand can be broken in the 5' direction of the barcode sequence, opening the circular molecule into a linear molecule with 5' single-stranded overhangs at each end that contain the same barcode sequence. In some embodiments, enzymatic extension of the 3' ends (for example, by Klenow exo– DNA polymerase or Taq DNA polymerase) copies the barcode sequence at each end, creating a fully double-stranded DNA molecule with the same barcode sequence at both ends. In some embodiments, extension by appropriate DNA polymerase enzymes leaves dA-tails useful for ligating additional adapters containing sequences that serve as PCR primer annealing sites for subsequent PCR amplification.

In some embodiments, the circularization adapter is prepared prior to ligation such that it contains two copies of the barcode sequence, or one copy of the barcode sequence and another copy of the reverse complement of that barcode sequence. In some embodiments, following circularization, the adapter is cut between the two barcodes prior to amplification. It can be advantageous to circularize the target around the barcode adapter such that the same barcode sequence becomes associated with both ends of the target molecule.

In some embodiments, adapters are attached by ligation. In some embodiments, ligation is facilitated by single-nucleotide tailing. In some embodiments, the adapters are dA-tailed and the targets are dT-tailed. In some embodiments, the adapters are dT-tailed and the targets are dA-tailed. In some embodiments, adapters are attached by blunt-end ligation. In some embodiments, adapters are incorporated during amplification. In some embodiments, adapter sequences are contained within PCR primers.

In some embodiments, interior regions of the amplified target molecule are exposed prior to circularization by fragmentation. In some embodiments, fragmentation is performed using the dsDNA fragmentase enzyme mixture from New England Biolabs, a mixture of two enzymes that creates random breaks in double-stranded DNA. Unlike exonucleases, fragmentase preserves both ends of the DNA molecule, both of which can give rise to productive circular molecules; unlike mechanical shearing, breaks are introduced along the length of the DNA molecule independent of the distance from an end or the size of the molecule; and the number of breaks per kilobase can be adjusted for different target molecule lengths by diluting the enzyme mixture or adjusting the reaction time. In some embodiments, fragmentation is achieved by mechanical shearing, or concatamerization by ligation followed by shearing.

In some embodiments, in place of mechanical or enzymatic fragmentation, fragments with random ends are generated during amplification with random (degenerate) or partially random oligonucleotide primers. In some embodiments, amplification is followed by further amplification with non-random primers. In some embodiments, amplification is followed by restriction digestion or other enzymatic treatments. In some embodiments, fragments with random ends are generated as described below in Example 8.

In some embodiments, barcode adapter-ligated target molecules are amplified with PCR. In some embodiments, the PfuCx Turbo DNA polymerase (Agilent) is used for PCR. This enzyme is compatible with uracil-containing primers, yet features a proofreading activity that reduces the error rate relative to Taq polymerases. In some embodiments, a single primer is used for PCR. Using a single primer has been shown to discourage the accumulation of primer dimers during PCR. In some embodiments, two or more distinct primers are used for PCR.

In some embodiments, the PCR mixture is supplemented with betaine, DMSO, or other additives or combinations thereof to reduce the sequence dependence of amplification efficiency, promoting a more even distribution of amplified products.

In some embodiments, the adapters that are attached to the two ends of a target molecule are identical. In some embodiments, the adapters that are attached to the two ends of a target molecule are distinct. In some embodiments, the adapters incorporate distinct PCR primer-annealing sequences and/or distinct sequencing primer-annealing sequences into the two ends of the target molecule. In some embodiments this is accomplished by adding a mixture of different adapters into the ligation mixture. In some embodiments a "forked" or "Y" adapter is used, comprising two oligonucleotides that are only partially complimentary, such that they anneal to form an adapter that is double stranded and ligation competent at one end, but forks into two non-complimentary single strands at the other end.

In some embodiments, amplification bias is reduced by a linear amplification stage prior to exponential amplification. In some embodiments, barcode-containing adapters with 3' overhangs are attached to the ends of the target molecule, such that only one of the two strands of the ligated target molecule is capable of annealing to a PCR primer at a set annealing temperature. In some embodiments, exponential amplification is triggered by the addition of a nested primer. In some embodiments, exponential amplification is triggered by a change in the annealing temperature.

In some embodiments, amplification is achieved by rolling-circle amplification (RCA) or hyperbranching rolling-circle amplification (HRCA). In some embodiments, a circularization adapter is ligated to the target, such that the two ends of the adapter ligate to the ends of the same target molecule to form a circular molecule. In some embodiments, the adapter contains a single barcode sequence, which is flanked in the 5' direction on each strand by nicking endonuclease recognition sequences. In some embodiments, the double-stranded DNA concatamers that result from RCA or HRCA are broken, by, for example, mechanical shearing or dsDNA fragmentase. In some embodiments, the resulting fragments are further treated with the nicking endonuclease, which introduce single-strand breaks on each side of the barcode, so that each strand of the barcode section becomes a 5' overhang at the end of the resulting fragments. In some embodiments, Klenow or another polymerase fills in these ends, copying the barcode to create a blunt end ready for circularization. In some embodiments, two loop adapters are ligated to the ends of the target to create a circular "dumbbell" structure that can be amplified by RCA or HRCA. In some embodiments, the resulting concatamers are fragmented and digested by a nicking endonuclease as described herein.

In some embodiments, some or all of the amplification is performed within emulsified compartments.

In some embodiments, fragmented PCR products are circularized by blunt-end ligation. In some embodiments, fragmented molecules are circularized with a bridging oligonucleotide or adapter, the creation of complementary sticky ends at the ends of the fragment, or the use of recombinases.

In some embodiments, short defined sequences are designed to follow the barcode sequence in the sequencing reads to positively distinguish true barcode sequences from spurious sequences. In some embodiments, these constant sequences are selected to promote incorporation of biotinylated deoxyribonucleotides (e.g., biotin-dCTP) into the ends of fragmented molecules during end-repair.

In some embodiments, size selection is used to enrich the library for long fragments to compensate for the diminished circularization efficiency of long fragments. In some embodiments, length-dependent binding to SPRI beads is used for size selection. In some embodiments, agarose or polyacrylamide electrophoresis gel purification is used for size selection.

In some embodiments, complete or partial sequencing primer sequences are included adjacent to the random barcode sequence in the barcode adapter. This sequence can anneal in downstream PCR to an oligonucleotide that adds the full sequencing primer sequence. In some embodiments, sequences corresponding to standard manufacturer-supplied sequencing primer mixtures are incorporated to maintain compatibility with such standard primer mixtures. In some embodiments, custom sequences are used, with a corresponding custom sequence primer in place of the standard sequencing primer mixture. Including the eventual sequencing primer sequence proximal to the barcode in the adapter can have at least two benefits:

(a) Because the sequencing read begins with the sequence directly downstream of the sequencing primer sequence, the barcode sequence is located at the beginning of one of the two paired-end sequencing reads. After the barcode sequence, the read continues directly into unknown region derived from the middle of the target molecule. This method can ensure that the random barcode is easily identified, and can avoid wasting sequencing capacity by repeatedly sequencing the region on the upstream side of the barcode (which derives from the same end of the original target molecule).

(b) The presence of a primer sequence adjacent to the barcode sequence can provide a simple way to distinguish DNA fragments containing barcodes from fragments that do not contain barcodes. These latter fragments can arise when a copy of the amplified target molecule is broken more than once, creating two end fragments with barcode sequences and one or more middle fragments without barcodes. Sequencing these barcode-free fragments wastes sequencing capacity because they contain no barcode sequence to link them to a parent DNA molecule.

In some embodiments, following fragmentation, circularization, and shearing, an asymmetric adapter is ligated to both ends the fragment. Is some embodiments, this adapter is composed of two oligonucleotides, one of which is longer than the other. In some embodiments, the shorter oligonucleotide is complimentary to a portion of the longer oligonucleotide, and upon annealing creates a ligation-competent adapter with a 3' dT-tail suitable for specific ligation to the dA-tailed fragment. In some embodiments, annealing creates a ligation-competent adapter with a 3' dA-tail suitable for specific ligation to the dT-tailed fragment. In some embodiments, annealing creates a ligation-competent adapter with a blunt end suitable for ligation to a blunt-ended fragment. In some embodiments, the adapter sequence is complimentary to a PCR primer that adds the second sequencing primer sequence by overlap-extension PCR, but only the longer of the two oligonucleotides is long enough to productively anneal to this primer during PCR. As a result, each of the two strands of the fragment can have an annealing-competent sequence at exactly one end. The second PCR primer in the reaction can anneal to the partial sequence adjacent to the barcode. As a result of this aspect, the desired fragment is in some cases the only exponentially amplified PCR product (e.g., which begins with a sequence complementary to at least part of the first sequencing primer, is followed by the barcode sequence and unknown sequence from the center of the target molecule, and ends with a sequence complementary to at least part of the second sequencing primer).

The method can be used to sequence the genome of an organism (e.g., an organism having multiple copies of each chromosome), single cell or virus haplotyping (e.g., B-cells, cancer stem cells, virus evolution), RNA sequencing (e.g., splice variants at multi-exon junctions, short sequence reads matching multiple sites in the genome), sequencing microbial populations (e.g., microbiome including pathogenecity islands, environmental microbiology including enzyme pathways like PKS or NRPS, sequencing of 16S rRNA including V4 region or full sequence.

Methods for Linking Genotype to Phenotype

Biopolymers such as proteins and nucleic acids can fold into three-dimensional structures and perform a diverse set of functions. In nature, these molecules perform a range of valuable functions: they efficiently catalyze chemical reactions, selectively bind desired target molecules, serve as mechanical scaffolds, assemble into materials, etc. A number of methods have been developed for the adaptation of natural biomolecules to perform tasks of interest to humans. Such tasks include catalyzing industrially important reactions or binding to medically relevant targets in the body. Evolutionary methods have been extensively used to modify natural biomolecules. These techniques use largely random methods to generate collections ("libraries") of variants, which are tested for the desired properties. Rational, computational, and intuitive methods are also used to design new molecules, modify natural molecules, or inform library creation. Methods for screening variants for desired properties generally fall into one of two classes. In the first class, a small enough number of variants is tested that each gene can be synthesized specifically, and each can be tested within a location (for example, a test tube or a microtiter plate well) that is known to contain that specific sequence. This type of experiment links information from any desired set of phenotypic assays with sequence information for each variant, but it is limited to a relatively small number of variants. In the second class, a larger number of variants are tested, but only a subset is selected for sequencing (nucleic acids are sequenced directly, while in the case of proteins the encoding nucleic acid is sequenced). The variant genes in this case are generally synthesized combinatorially, and their individual sequences are not known until they are determined by sequencing reactions. As before, this type of approach provides linked sequence-activity data for only a relatively small number of variants.

When multiple improved variants are found, it is often desirable to combine the causative mutations into a single variant, since the effects of beneficial mutations are often additive or compounding. Statistical methods are increasingly being incorporated into these approaches to help improve the search efficiency in the face of overwhelming combinatorial complexity. By sequencing a number of mutant genes and measuring the activity of the proteins they encode, the effects of individual mutations can be statistically isolated, and the best mutations can be identified more quickly. However, the need to either individually synthesize or individually sequence interesting variants drastically limits the amount of information that can be collected. Recently, "deep" sequencing has been used to simultaneously sequence thousands of mutants that survive a functional selection. This technique allows unprecedented statistical power. However, it is limited to binding proteins and enzymes with activity amenable to selections (for example, bond-forming enzymes or those whose activity can be linked to cell survival or growth). In addition, the prevalence of a mutant within the selected population is the only indication of its activity relative to other mutants.

In one aspect, the present disclosure fulfills a need for generation of large numbers of linked molecular genotype/phenotype pairs. In some embodiments, the genotype/phenotype pairs can be analyzed using statistical methods and can be optionally used to create biological molecules having superior and/or new properties.

In one aspect, the present disclosure fulfills a need for generation of large numbers of linked molecular genotype/phenotype pairs. In some embodiments, the genotype/phenotype pairs can be analyzed using statistical methods and can be optionally used to create biological molecules having superior and/or new properties.

In one embodiment, the sequences of nucleic acids are associated with positions on an array, and the phenotypes of the encoded variant molecules are determined in parallel at those positions. In some embodiments, measurements of the properties of interest of each variant are collected and linked to information allowing the identification, reproduction, or analysis of the sequence of each variant. This method can be applied to many types of biomolecular function, and it may provide a direct link between sequence information and one or more specific phenotypic characteristics. The methods described herein produce linked sequence-phenotype data for a large number of variants.

In one embodiment, the variant molecules are proteins or peptides. In other embodiment, the variant molecules are nucleic acids, small molecules encoded by nucleic acids, proteins or peptides containing non-natural amino acids, or non-protein foldamers, such as peptoids or beta-peptides, encoded by nucleic acids.

Next-generation sequencing machines use massively parallel arrays to sequence millions of DNA molecules simultaneously. The present method includes modification of these, or similar machines to measure enzyme activity at the same array position at which is sequenced all or part of the encoding gene, or a short barcode sequence that can be connected to the full gene sequence. An emulsion-based method can be used to attach an enzyme and its encoding DNA to the same microbead. Each enzyme can then be assayed for activity at the same position at which sequencing data that directly or indirectly identifies the genotype is collected. Statistical analysis of the millions of linked sequence/activity data points can then inform subsequent rounds of designs.

Read length limitations currently prevent more than a small stretch of sequence from being determined at once, but read lengths continue to increase, and within a few years sequencing of entire genes in a single read may be possible. For example, each position on the array can contain a nanopore-based sensor, which can detect enzymatic products as they pass through or occlude the pore, and also sequence the encoding DNA.

Alternatively, a sequence outside the coding region can be sequenced on the array. This region can be short enough to simplify and facilitate sequencing, yet long enough to serve as a unique identifier of the corresponding full-length gene sequence. Because this short barcode sequence can be determined on the array, at the same position as phenotypic data collection, the barcode can serve to link the array address of a particular variant with genetic information that can be used to track the variant after it is removed from its position on the array. The short barcode region can be amplified by emulsion PCR upstream to produce sufficient copies for sequencing. For example, these copies can be attached to the surface of the same microbead as the full gene and the protein product. The small size of this amplicon can be conducive for efficient amplification in emulsion PCR. The full gene can also be amplified in the same or a separate emulsion PCR as needed to increase protein expression. The barcode sequence can be completely degenerate (i.e., poly-N) or the degeneracy can be constrained to facilitate sequence determination. For example, the sequence can comprise positions allowed to be A or T alternating with positions allowed to be G or C, which can reduce or eliminate potential problems experienced by some sequencing methods when sequencing homopolymer runs. The degenerate region can also be flanked or interspersed with partially or fully defined positions to assist with quality control in downstream computational analysis.

Given a suitable long-read technology, the present disclosure includes sequencing a short barcode region on the array, collecting the variant genes off the array, amplifying and/or manipulating the DNA as needed to prepare it for long-read sequencing, and then sequencing the full-length genes with a long-read method to generate a single sequence that spans the barcode sequence and the full gene sequence. The full gene sequence can be thereby linked to the corresponding phenotypic information collected on the array by virtue of the barcode sequence, which is linked to the array position by sequencing on the array, and linked to the full gene sequence by a long read.

Sequencing can be based on measuring fluorescence or pH. Fluorescence is commonly used to measure enzymatic activity, as fluorogenic substrates can be created for many enzymatic activities of interest. Described herein is use of fluorescence-based machines to measure the activity of an enzyme and collect information that directly or indirectly determines the sequence of its co-localized encoding gene. Examples of cyclic array sequencing by ligation or by pyrosequencing include Shendure, J., Porreca, G. J., Reppas, N. B., Lin, X., McCutcheon, J. P., Rosenbaum, A. M., Church, G. M. (2005). Accurate multiplex polony sequencing of an evolved bacterial genome. *Science* (New York, N.Y.), 309(5741), 1728-32. doi:10.1126/science.1117389, which is hereby incorporated in its entirety, and Margulies, M., Egholm, M., Altman, W. E., Attiya, S., Bader, J. S., Bemben, L. a, Rothberg, J. M. (2005). Genome sequencing in microfabricated high-density picolitre reactors. *Nature*, 437(7057), 376-80. doi:10.1038/nature03959, each of which is hereby incorporated in its entirety.

For example, the Ion Torrent PGM calls bases by detecting the minute change in pH caused by the protons released when DNA polymerase incorporates a new base (Rothberg, J. M., Hinz, W., Rearick, T. M., Schultz, J., Mileski, W., Davey, M., . . . Bustillo, J. (2011). An integrated semiconductor device enabling non-optical genome sequencing. *Nature*, 475(7356), 348-52. doi:10.1038/nature10242, which is hereby incorporated in its entirety).

However, many other interesting reactions also cause pH changes. As described herein, an apparatus containing such chips may be used to provide massively parallel activity measurements and sequences of enzymes that catalyze any reaction involving the release or uptake of ions. The present method of collecting coupled activity and sequence data from enzymes with a wide range of activities rapidly accelerates understanding of enzyme function and the engineering of enzymes with novel activities.

Described herein are methods to co-locate nucleic acids and their encoded proteins on an array, such that an apparatus capable of the parallel measurement of one or more signals (e.g., via one or more sensors) such as fluorescence, luminescence, temperature change, or pH change can record both the sequence of all or part of the nucleic acid or a short barcode nucleic acid uniquely associated with the full nucleic acid, and the phenotype of the corresponding protein. In some cases, the one or more signals are proportional to a phenotype or relatable to a phenotype by a calibration curve. Sequence data and one or more types of phenotypic data may be collected in separate reactions, but they are linked by virtue of occurring at the same (or otherwise connected or related) physical locations on the array.

The methods may similarly be used to collect linked genotype and phenotype information from nucleic acid aptamers, proteins containing non-canonical amino acids, small molecules encoded by nucleic acids, proteins or peptides alone using protein sequencing methods, and so on.

In one embodiment, DNA molecules are attached to microbeads or any suitable solid support. Attachment can be achieved by any suitable method, including binding of a biotin or double-biotin group attached to the DNA to stepta-vidin or avidin proteins attached to the surface of the microbeads. This may result in each bead binding roughly one DNA molecule. The beads may also be incubated with biotinylated primers for use in the following emulsion PCR. The beads are then suspended in a solution containing PCR reagents, which is emulsified into a continuous oil phase. All or a portion of the DNA is then amplified by emulsion PCR, and some fraction of the synthesized DNA copies are attached to the bead. The emulsion is broken and the beads are pooled and washed. The beads are now ready for sequencing by technologies including the Ion Torrent, Roche/454, or Life Technologies APG systems. At this point, in one embodiment, the beads are incubated with biotinylated antibodies specific for a peptide tag. They are then washed and suspended in a solution containing the required components for cell-free protein synthesis and again emulsified into an immiscible phase. Within the emulsion droplets, the clonal DNA is transcribed to produce mRNA, which is translated to produce the encoded variant protein. The protein is fused to the peptide tag for which the bead-bound antibodies are specific, such that the produced protein becomes physically linked to the same bead to which is also linked its encoding DNA. The production of such microbead-DNA-protein complexes has been described in the literature (Stapleton J A, Swartz J R. Development of an In Vitro Compartmentalization Screen for High-Throughput Directed Evolution of [FeFe] Hydrogenases *PLoS ONE*. 2010; 5(12):e10554, which is hereby incorporated in its entirety.)

In one embodiment, the beads are then applied to an array and analyzed with an apparatus capable of (i) sequencing bead-bound DNA in parallel using technology such as that used in Ion Torrent, Roche/454, or Life Technologies APG systems, and (ii) delivering solutions to create the conditions for a desired protein assay, other than those used in the sequencing reaction, and measuring in parallel position-linked signals (e.g., fluorescence, luminescence, temperature change, or pH change) that correspond to the performance of each protein variant in the assay. Application of the parallel sequencing technology provides sequence information associated with each position on the array. All or part of the DNA can be sequenced, in one step or in multiple steps (e.g., each with different priming oligonucleotides). Prior or subsequent to sequencing, application of the parallel assay technology provides one or more measurements of the phenotype of the protein in one or more assays, again associated with each position on the array. Linked genotype-phenotype information can be generated for a large number of variants in parallel.

For example, the green fluorescent protein (GFP) is widely used as an in vivo marker in biological studies, and has been the target of much protein engineering to understand its function and to generate variants with improved properties such as stability, maturation speed, and altered spectral properties. The methods described herein may be used to rapidly gather a large amount of sequence-activity data for use in GFP engineering. A library of biotinylated genes encoding GFP variants tagged with unique barcode sequences may be generated, for example, by error-prone PCR with a degenerate barcode region designed into one of the primers. The genes are attached to microbeads and amplified by emulsion PCR. The barcode region alone can be separately amplified by emulsion PCR, such that many copies of the barcode sequence are attached to the microbead. The genes can be transcribed and translated by emulsion cell-free protein synthesis as described previously. The microbeads, which display clonal variant DNA and its encoded variant GFP protein, are applied to an array. The barcode DNA on each bead is sequenced in parallel using known next-generation sequencing technology. Following (or prior to) the sequencing stage, the GFP variant proteins attached to each bead are assayed. In one example, the array is exposed to light whose wavelength is controlled by one or more filters, and the machine measures the fluorescent light emitted from each position on the array that passes through a second set of one or more filters. Multiple measurements may be performed sequentially, changing the input and output filters with each measurement to acquire detailed information on the fluorescence properties of each variant. The temperature and chemical environment (e.g., the concentration of guanidinium hydrochloride or urea) may also be varied or titrated while measuring the fluorescent output of each variant, providing information on additional properties of the variants (e.g., stability). If a superior variant were present on the array, the linked sequence information collected in sequencing may be used to reproduce that protein for further characterization. Alternatively, the large number of linked sequence/phenotype measurements may be analyzed statistically to identify mutations or combinations thereof that are beneficial for GFP performance, and these mutations can be recombined in one or a few designed variants or in a new library for further rounds of screening. In one embodiment, a machine-learning algorithm is trained to predict the properties of a GFP variant of arbitrary sequence. The large datasets provided by the methods described herein may be useful in the engineering of new proteins and in furthering scientific understanding of how proteins and enzymes fold and function.

In some instances, emulsion PCR is less efficient with longer DNA templates. In some embodiments multiple sets of primers may be used in emulsion PCR, simultaneously or sequentially, to amplify shorter stretches of the DNA sequence. These short sequences lack an RNA polymerase promoter and are not transcribed in cell-free protein synthesis, but are suitable for sequencing. The entire gene can be represented in a set of such short amplicons, which can be sequenced sequentially on the array using different priming oligonucleotides. This embodiment may include emulsion PCR to amplify the entire gene if such amplification is necessary to eventually synthesize enough protein for the desired phenotypic assays.

Many other similar embodiments may be imagined by those familiar with the art. For example, emulsion PCR could be omitted, or replaced with in vitro transcription, followed in some embodiments by a reverse-transcription. Alternatively, biotinylated RNA could be transcribed in bulk solution and then attached to microbeads.

While the above descriptions have focused on the binding of molecules to microbeads, the method is not limited in this regard. Nucleic acids can be bound directly to surfaces such as glass. The encoded proteins can be synthesized prior to or following nucleic acid binding to the chip and bound to the same surface or to the nucleic acids themselves (e.g., by ribosome display, RNA display, or DNA display). Surface-bound nucleic acids can optionally be amplified before or after transcription or translation by methods including bridge PCR. Binding the nucleic acids to a surface may allow other high-throughput sequencing technologies to be used, including those developed by Illumina/Solexa and Helicos BioSciences. Alternatively, single nucleic acid/protein complexes such as those that result from ribosome display, RNA display, or DNA display can be sequenced by technologies such as those developed by Pacific Biosciences, or by nanopore sequencing.

In another embodiment, the active molecule is RNA rather than protein. In this case, a number of approaches can be used, including but not limited to the following:

(i) a protocol similar to the microbead-attachment protocol described above can be used, but the cell-free protein synthesis is replaced by in vitro transcription within the emulsion. The phenotypes of the resulting RNAs are measured as described above (e.g., pH changes).

(ii) a microbead-attachment protocol can be used, wherein the DNA and the microbead are co-compartmentalized during an in vitro transcription that results in decoration of the microbead with RNA. The RNA is then sequenced directly or reverse-transcribed to generate DNA for sequencing.

(iii) single molecules of RNA are attached to beads, surfaces, or surface-bound molecules such as polymerases, and sequenced directly or reverse-transcribed to generate DNA for sequencing, prior to or following single-molecule characterization.

In some embodiments, for example where enzymatic rates are of interest, methods are described herein for estimating approximately how many copies of the enzyme were bound to a given microbead during protein synthesis. This can be accomplished in a number of ways. For example, the enzyme can be linked at a defined stoichiometry to a molecule or fusion of known characteristics. Measurement of a signal from the array position specific to this calibration molecule allows determination of the number of copies of the molecule of interest at each position in the array. For example, the number of these control molecules can be determined by measuring fluorescence, luminescence, temperature change, or pH change as a result of enzymatic activity or binding to a probe molecule such as an antibody linked to a fluorescent molecule, an enzyme, or an enzymatic substrate.

In some embodiments, for example where binding is of interest, the molecule to be bound is conjugated or fused to an enzyme capable of generating a signal with a high turnover rate, so that each bound molecule generates an amplified signal to facilitate detection. In some embodiments, the substrate and/or product of this reaction is attached to microbeads or to the array surface to preserve the localization of the signal within the particular array position.

In another embodiment, the nucleic acid sequences to be tested are spotted or printed directly onto known positions on the array. This can be done by any one of a number of technologies, including ink-jet or photolithography-based methods. In some embodiments, the nucleic acid is RNA, but it can also be DNA, in which case it may be transcribed by any method that preserves the spatial information that locates the sequence on the array. Ligation between the DNA and corresponding RNA is one such mechanism. Array-bound RNA may be translated using methods such as ribosome display or RNA display, wherein the newly synthesized protein remains spatially associated with its encoding RNA or DNA or the array. Alternatively, peptides or proteins with specific sequences can be synthesized directly onto defined positions on the array by solid-phase synthesis. In these embodiments sequencing is not necessary, as the sequence of the nucleic acid printed in each location is known. Phenotypic characterization takes place in parallel on the array as described.

In another embodiment, oligonucleotides containing "barcode" sequences, each of which refer to a specific full-length variant gene, are printed onto an array. Nucleic acid/protein complexes then attach to the array by way of hybridization between the nucleic acid and the bound oligonucleotides. The nucleic acids contain complementary barcode sequences that allow specific annealing to a particular array-bound oligonucleotide. In some embodiments, nucleic acid/protein complexes (where the nucleic acid can be RNA or DNA, and can be complexed with its encoded protein by ribosome display, RNA display, DNA display, mutual attachment to a microbead, and so on) are synthesized and assembled in bulk solution and then directed to known positions on an array. On-array sequencing is therefore not needed, and long-read sequencing can be subsequently performed if necessary to link the barcode sequences with the full-length gene sequences. Parallel, location-linked phenotypic characterization takes place as described herein. The protein-associated nucleic acid could contain the open reading frame along with the barcode, or it could contain only the barcode. The latter scenario could be accomplished by, for example, binding a nucleic acid molecule comprising a barcode and an open reading frame to a microbead, and amplifying only the barcode section by emulsion PCR such that the bead becomes decorated with many copies of the barcode sequence. Alternatively, a method similar to DNA display could be used to attach a barcode sequence directly to the protein.

The methods can also be applied in many other areas of science and engineering. For example, it could be used to rapidly characterize unknown open reading frames from, e.g., environmental samples. These genes could be expressed, displayed on the array, and exposed sequentially to a battery of tests for common enzymatic activities, binding partners, biophysical properties, and the like.

The method may be used to modify the properties of an existing enzyme or ribozyme by directed evolution. A mutant library is generated from a starting parent gene. The library is analyzed using the described method, which provides data describing the complete or partial sequence and phenotype of each mutant. This data is used to generate a new mutant library, which can be based on one or more mutants with desirable properties identified by the method, or which can be combinatorially assembled from oligonucleotides containing one or more mutations identified by the method as being statistically associated with desirable phenotypes. This process is iteratively repeated for as many cycles as desired.

It may be desirable to sequence the nucleic acids more than once while maintaining their positions on the array, for example to ensure sequencing accuracy. Many parallel sequencing technologies have read lengths that are short relative to the length of a typical gene. In some embodiments, different regions of a nucleic acid may be sequenced in multiple sequential sequencing runs. These partial sequences are collected sequentially but remain associated with the same array position. The partial sequences may then be combined using overlapping regions or by comparison to a known parent or reference sequence. The partial sequences may be generated by sequencing regions of the same nucleic acid molecule. Alternatively, sections of the long nucleic acid polymer that contains the open reading frame can be individually amplified to create a number of smaller nucleic acid molecules, which remain associated with the parent, e.g. by binding to the same bead following emulsion PCR. These smaller nucleic acids can then be sequenced, and these partial sequences combined as described previously.

In some aspects, an array described herein comprises at least about 1, 2, $10^1$, $10^2$, $10^3$, $10^4$, $10^5$, $10^6$, $10^7$, $10^8$, $10^9$, $10^{10}$, $10^{11}$ or more sensors. In some aspects, an array described herein comprises at most about $10^{11}$, $10^{10}$, $10^9$, $10^8$, $10^7$, $10^6$, $10^5$ $10^4$, $10^3$, $10^2$, $10^1$, 2 sensors or 1 sensor. A sensor may measure a signal associated with a signal associated with fluorescence, pH change, temperature change, luminescence, or any combination thereof. In some aspects, an array described herein may be interrogated by a sensor. Such a sensor may measure a signal associated with a signal associated with fluorescence, pH change, luminescence, temperature change or any combination thereof associated with the array. In some aspects, an array comprises one or more chemical field-effect transistor (chemFET) sensors.

In some aspects, a phenotype described herein may be any phenotype of interest. Non-limiting examples of phenotypes include enzyme specificity, binding affinity, binding specificity and stability when exposed to a chemical condition or a temperature. In some aspects, a method includes contacting proteins to a plurality of solutions comprising substrates at a plurality of concentrations. In some aspects, a method includes contacting proteins to a plurality of solutions comprising ligands at a plurality of concentrations. In some aspects, a method includes measuring a phenotype at a plurality of temperatures.

Computer Control Systems

Figure 9:
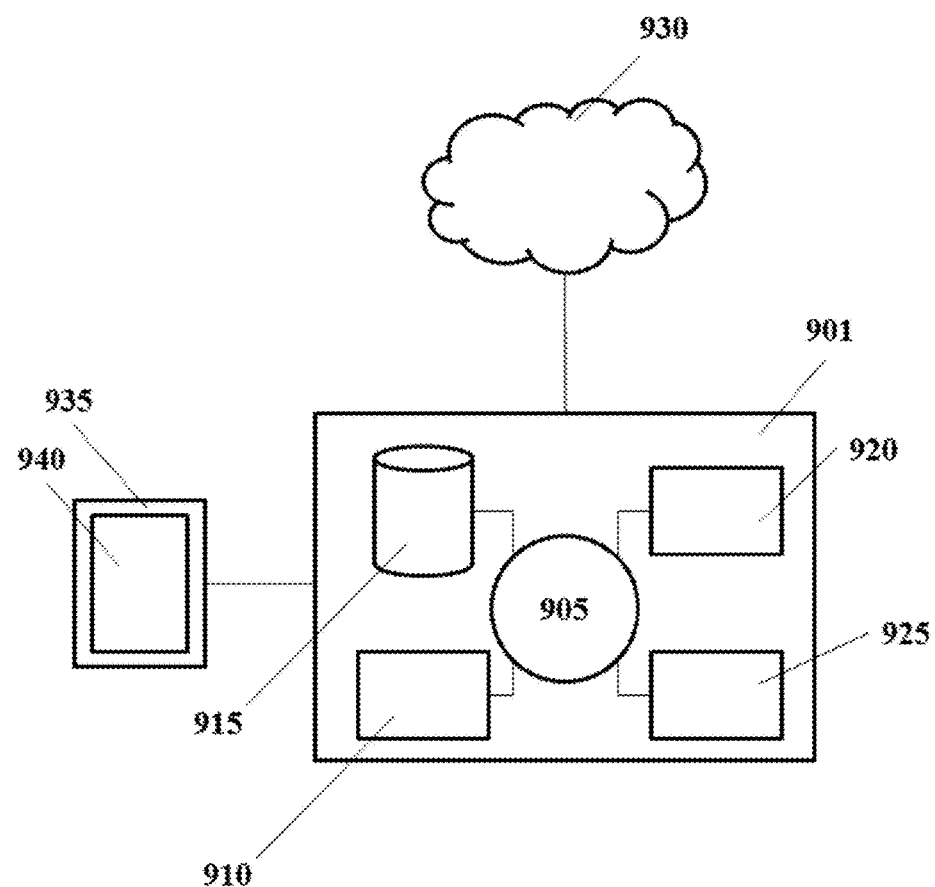
FIG. 9 schematically depicts an example computer control system described herein.

The present disclosure provides computer control systems that are programmed to implement methods of the disclosure. FIG. 9 shows a computer system 901 that is programmed or otherwise configured to operate instrumentation (e.g. a thermal cycler, fluid handling apparatuses including pumps and valves, a sequencing instrument, a sequencing platform, etc.), analyze and store sequencing reads, perform sequence assembly, store results of a sequence assembly, display data (e.g., results of sequencing analysis, instrument operational parameters, etc). The computer system 901 can regulate various aspects of devices (e.g., thermal cyclers, fluid handling apparatuses including pumps and valves, sequencing instrumentation, sequencing platforms, etc.), sequence read analysis methods and sequence assembly methods described herein. The computer system 901 can be an electronic device of a user or a computer system that is remotely located with respect to the electronic device. The electronic device can be a mobile electronic device.

The computer system 901 includes a central processing unit (CPU, also "processor" and "computer processor" herein) 905, which can be a single core or multi core processor, or a plurality of processors for parallel processing. The computer system 901 also includes memory or memory location 910 (e.g., random-access memory, read-only memory, flash memory), electronic storage unit 915 (e.g., hard disk), communication interface 920 (e.g., network adapter) for communicating with one or more other systems, and peripheral devices 925, such as cache, other memory, data storage and/or electronic display adapters. The memory 910, storage unit 915, interface 920 and peripheral devices 925 are in communication with the CPU 905 through a communication bus (solid lines), such as a motherboard. The storage unit 915 can be a data storage unit (or data repository) for storing data. The computer system 901 can be operatively coupled to a computer network ("network") 930 with the aid of the communication interface 920. The network 930 can be the Internet, an internet and/or extranet, or an intranet and/or extranet that is in communication with the Internet. The network 930 in some cases is a telecommunication and/or data network. The network 930 can include one or more computer servers, which can enable distributed computing, such as cloud computing. The network 930, in some cases with the aid of the computer system 901, can implement a peer-to-peer network, which may enable devices coupled to the computer system 901 to behave as a client or a server.

The CPU 905 can execute a sequence of machine-readable instructions, which can be embodied in a program or software. The instructions may be stored in a memory location, such as the memory 910. The instructions can be directed to the CPU 905, which can subsequently program or otherwise configure the CPU 905 to implement methods of the present disclosure. Examples of operations performed by the CPU 905 can include fetch, decode, execute, and writeback.

The CPU 905 can be part of a circuit, such as an integrated circuit. One or more other components of the system 901 can be included in the circuit. In some cases, the circuit is an application specific integrated circuit (ASIC).

The storage unit 915 can store files, such as drivers, libraries and saved programs. The storage unit 915 can store user data, e.g., user preferences and user programs. The computer system 901 in some cases can include one or more additional data storage units that are external to the computer system 901, such as located on a remote server that is in communication with the computer system 901 through an intranet or the Internet.

The computer system 901 can communicate with one or more remote computer systems through the network 930. For instance, the computer system 901 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 901 via the network 930.

Methods as described herein can be implemented by way of machine (e.g., computer processor) executable code stored on an electronic storage location of the computer system 901, such as, for example, on the memory 910 or electronic storage unit 915. The machine executable or machine readable code can be provided in the form of software. During use, the code can be executed by the processor 905. In some cases, the code can be retrieved from the storage unit 915 and stored on the memory 910 for ready access by the processor 905. In some situations, the electronic storage unit 915 can be precluded, and machine-executable instructions are stored on memory 910.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 901 can include or be in communication with an electronic display 935 that comprises a user interface (UI) 940 for providing, for example, operation parameters of an instrument (e.g., a thermal cycler, a sequencing instrument, fluid handling instrumentation), instrument performance, parameters of a sequence assembly method, results and associated statistics of a sequence assembly data, etc. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 905. The algorithm can, for example, initiate electronic signals that are processed to operate instrumentation (e.g. a thermal cycler, fluid handling apparatuses including pumps and valves, a sequencing instrument, a sequencing platform, etc.), analyze and store sequencing reads, perform sequence assembly and/or store results, display data (e.g., results of sequencing analysis, instrument operational parameters, etc) to a user, transmit to or receive data from a remote computer system, etc.

EXAMPLES

Additional aspects and details of the invention will be apparent from the following examples, which are intended to be illustrative rather than limiting.

Example 1

Standard Protocols

Standard protocols used in many Examples of the disclosure were provided. A solution of two oligonucleotides (e.g., where the first (the barcode-containing oligo) was any of oligo 1, oligo 2, oligo 3, or oligo 4, and the second (the extension oligo) was any of oligo 5, oligo 6, or oligo 7, where oligo 5 is used with oligo 1 or oligo 4; oligo 6 is used with oligo 1, oligo 2, or oligo 4; and oligo 7 is used with oligo 3—the various oligos corresponding to those shown in Table 1 below), at 2 µM and 5 respectively in NEBuffer 2 (New England Biolabs (NEB), Ipswich, Mass.) was heated to 95° C. for 10 minutes and allowed to cool to 37° C. over 30 minutes. Five units of Klenow exo– (NEB) and 0.3 mM each dNTP (NEB) were added and the mixture was incubated at 37° C. for 60 minutes.

The library DNA to be sequenced was linearized and fragmented to the desired size by restriction digestion, fragmentation, or PCR as necessary. In some aspects, depending on the source of the nucleic acid and the goals of the project, the nucleic acid is fragmented into sizes from about 1 kb to about 20 kb. For example, genomic DNA is usually sheared to about 10 kb. In other aspects, genes of about 3 kb are the sequence of interest. The gene can be amplified from source DNA or cut out of a larger genome with restriction enzymes. The DNA to be sequenced was typically diluted to 50 µL at 10 ng/µL and fragmented into ~10 kb pieces with a g-TUBE (Covaris, Woburn, Mass.) by centrifugation at 4200 g according to the manufacturer's protocol.

The DNA was end-repaired with the NEBNext End Repair Module (NEB) according to the manufacturer's suggested protocol and purified with a Zymo DNA Clean & Concentrator column (Zymo Research, Irvine, Calif.) and eluted in 20 µL of buffer EB (an elution buffer used in eluting DNA). The DNA was then dT-tailed by incubation in 1×NEB buffer 2 with 1 mM dTTP (Life Technologies, Grand Island, N.Y.), 5 units Klenow exo–, and 10 units polynucleotide kinase at 37° C. for 1 hour.

250 fmol of library DNA and 5 pmol of barcoded tipartite adapters comprising an outer PCR primer region, an inner sequencing primer region, and a central barcode region were ligated with TA/Blunt MasterMix (NEB) according to the manufacturer's protocol, purified with a Zymo column or with gel purification with size selection with the Qiagen Gel Extraction kit and eluted in 20 µL of buffer EB. The tripartite adapters, see, e.g., oligo 1 in Table 1, are designed so that barcode number takes into consideration target number. For example, an adapter comprising a 16N barcode works for about 10 to about 20 million target sequences.

Two single-stranded oligonucleotides are ordered from a supplier, annealed together, and the shorter one is extended to form the double-stranded adapter. The number of possible barcode sequences is $4^n$, where n is the number of degenerate bases. That number should be at least 100 times higher than the number of DNA molecules to be tagged to ensure that each molecule receives two unique tags. For example, n=16 has been used in experiments described herein. $4^{16}$=4.3 billion. In various aspects, the barcode is made shorter (to maximize the portion of the sequencing read that reads target sequence) or longer (to ensure that no two molecules get identical barcodes).

Oligo 5, oligo 6 and oligo 7, shown in Table 1 below, represent both the shorter adapter extension oligo described herein above and the PCR primer (see Rungpragayphan et al., J. Mol. Biol. 318:395-405, 2002). Theoretically, the extension oligo may be any sequence long enough for primer annealing during PCR. The extension oligo anneals to the barcode-containing oligo and is extended by Klenow exo⁻ polymerase, copying the barcode and forming a dA-tailed double-stranded adapter. The region on the 5' end of the barcode-containing oligo is the sequence from the Illumina Universal sequencing primer. If a different sequencing primer is used for sequencing, the barcode-containing oligo should be modified accordingly.

The adapters were ligated at both ends of the DNA. A single adapter is ligated to each end of the nucleic acid by including an overhang on the 3'strand of the non-ligating end, thus blocking concatamerization on the end of the adapter. Library molecules that failed to ligate to an adapter at both ends were removed by incubation with 10 units of exonuclease III (NEB) and 20 units of exonuclease I (NEB) in NEBuffer 1 for 45 minutes at 37° C., followed by 20 minutes at 80° C.

Oligo 2, shown in Table 1 below, comprises an example of one strand of the tripartite adapter. The oligo, from 5' to 3', comprises: (1) NNN, which is an optional degenerate 5' end to reduce sequence bias of ligation, (2) CCTACACGACGCTCTTCCGATCT (SEQ ID NO: 13), which is the annealing sequence for oligo 11 (shown in Table 1 below), which adds the Illumina TruSeq Universal adapter during the final limited-cycle PCR; (3) NNNNNNNNNNNNNNNN, which is the degenerate barcode sequence; (4) CC, which is a short defined sequence to confirm that the previous bases comprise the barcode and to promote biotin-dCTP incorporation during end repair; (5) AGGAATAGTTATGTGCATTAATGAATGG (SEQ ID NO: 14), which is an annealing sequence for oligo 6 (shown in Table 1 below), which both extends oligo 2 (shown in Table 1 below) to form the double-standard tripartite adapter and is the primer for the first PCR; and (6) CGCC, which is a short overhanging sequence to prevent ligation on this end of the tripartite adapter, and which can be extended to include a primer annealing site for linear amplification.

The ligation product was quantified with the Quant-It kit (Life Technologies) and diluted to about 10,000 molecules per µL to impose a complexity bottleneck. A complexity bottleneck sets the number of molecules that are amplified, matching the sequencing capacity to ensure that each molecule accumulates enough sequencing reads to assemble long synthetic reads. In this example, ten thousand molecules of adapter-ligated DNA were amplified by PCR using a PfuCx polymerase (Agilent Technologies, Santa Clara, Calif.) or LongAmp Taq DNA polymerase (NEB) and a single primer (e.g., oligo 6 shown in Table 1 below) at 0.5 mM. The following thermocycling conditions were carried out: 92° C. for 2 minutes, followed by 40 cycles of 92° C. for 20 seconds, 55° C. for 20 seconds, and 68° C. for 3 minutes/kb, and followed by a final hold at 68° C. for 10 minutes.

The PCR products were purified with a Zymo column or a Qiagen Gel Extraction kit and eluted in 50 μL of buffer EB. Between 200 ng and one μg of DNA was mixed with 1 unit of USER enzyme in a 45 μL reaction volume and incubated for 30 minutes at 37° C. Two μL of 1:5 diluted dsDNA fragmentase (NEB), 100 μg/mL bovine serum albumin, and 5 μL of dsDNA fragmentase buffer were added and the mixture incubated on ice for 5 minutes. 0.5-2 μL of dsDNA fragmentase (NEB) (volume adjusted based on amount and length of DNA to be fragmented) were then added and the mixture incubated at 37° C. for 15 minutes. The reaction was stopped by addition of 5 μL of 0.5 M EDTA and fragmentation was confirmed by the presence of a smear on an agarose gel. The DNA was purified with a Zymo column or 0.8 volumes of Ampure XP beads (Beckman Coulter, Brea, Calif.), and eluted in 20 μL of buffer EB.

Two μL of 10×NEBuffer 2 were added and fragmented DNA was incubated with 0.5 μL of "*E. coli* DNA ligase for fragmentase" (NEB) for 20 minutes at 20° C. Three units of T4 DNA polymerase (NEB), 5 units of Klenow fragment (NEB), and 50 μM of biotin-dCTP (Life Technologies) were added; and the reaction was incubated for 10 minutes at 20° C. Fifty μM dGTP, dTTP, and dATP were added and the mixture was incubated for an additional 15 minutes, purified with a Zymo column or 1 volume of Ampure XP beads, eluted in 20 μL of buffer EB, and quantified by absorbance at 260 nm.

200-1000 ng of DNA at a final concentration of 1 ng/μL were mixed with 3000 units of T4 DNA ligase and T4 DNA ligase buffer to 1×, and incubated at 16° C. for 16 hours. Linear DNA was digested by the addition of 10 units of T5 exonuclease and incubation at 37° C. for 60 minutes. Circularized DNA was purified with a Zymo column and eluted in 130 μL of buffer EB. The DNA was fragmented with an S2 disruptor (Covaris, Inc., Woburn, Mass.) to lengths of about 500 bp to about 800 bp.

Twenty μL of Dynabeads M-280 Streptavidin Magnetic Beads (Life Technologies) were washed twice with 200 μL of 2×B&W buffer (1×B&W buffer: 5 mM Tris-HCl (pH 7.5), 0.5 mM EDTA, 1 M NaCl) and resuspended in 100 μL of 2×B&W buffer. The DNA solution was mixed with this bead solution and incubated for 15 minutes at 20° C. The beads were washed three times with 200 μL of 1×B&W buffer, and twice in 200 μL of buffer EB. At this point, 15% (30 μL) of the beads were removed to a new tube for two-tube barcode pairing (see below). The remaining beads were resuspended in NEBNext End Repair Module solution (New England BioLabs Inc., Ipswich, Mass.) (42 μL water, 5 μL End Repair Buffer, and 2.5 μL End Repair Enzyme Mix), incubated at 20° C. for 30 minutes, washed three times with 200 μL of 1×B&W buffer, and then twice with 200 μL of buffer EB. The beads were resuspended in NEBNext A-tailing Module solution (NEB), incubated at 37° C. for 30 minutes, and washed three times with 200 μL of 1×B&W buffer, and then twice with 200 μL of buffer EB.

A 15 μM equimolar mixture of two oligonucleotides (e.g., oligos 8 and 9, as set out in Table 1 below) in 1×T4 DNA ligase buffer was incubated at 95° C. for 10 minutes and allowed to slowly cool to room temperature. The beads were resuspended in a solution comprising 5 μL of NEB Blunt/TA ligase master mix (NEB), 0.3 μL of 15 μM adapter oligo solution, and 4 μL of water. The mixture was incubated for 15 minutes at room temperature. The beads were washed three times with 200 μL of 1×B&W buffer, and twice with 200 μL of buffer EB. The beads were resuspended in a 50 μL PCR solution comprising 36 μL of water, 10 μL of 5× Phusion HF DNA polymerase buffer, 1.25 μL of each of 10 μM solutions of the standard Illumina Index and Universal primers (oligos 5 and 6 (set out below in Table 1), and 0.02 units/μL Phusion DNA polymerase (Thermo Fisher Scientific, Inc., Skokie, Ill.). The following thermocycling program was used: 98° C. for 30 seconds, followed by 18 cycles of 98° C. for 10 seconds, 60° C. for 30 seconds, and 72° C. for 30 seconds, and a final hold at 72° C. for 5 minutes. The supernatant was retained and the beads discarded.

The PCR product was purified with 0.7 volumes of Ampure XP beads and eluted in 10 μL buffer EB, or 500-900 bp fragments were size-selected on an agarose gel, gel-purified with the MinElute Gel Extraction kit, and eluted in 15 μL of buffer EB. The size distribution of the DNA was measured with an Agilent bioanalyzer and cluster-forming DNA was quantified by qPCR. The DNA fragments were sequenced on a MiSeq, NextSeq or HiSeq sequencer (Illumina) with standard Illumina primers. Illumina provides primer mixes with their sequencing reagent kits that include sequencing primers compatible with all of their various sequencing preparation kits. For example, multiple sequencing kits, each with their own sequences, are available, and the primer mixture contains primers compatible with all of the kits. Oligos 8 and 9, set out in Table 1 below, anneal to one another to form the asymmetric adapter. Oligos 10 and 11, set out in Table 1 below, are PCR primers that add the complete Illumina flowcell sequences. Sequences used in oligo 2, 10, and 11, as set out in Table 1 below, are from the Illumina Small RNA Kit. One oligo anneals to the asymmetric adapter, while the other oligo anneals to a region of the barcode adapter that is now on the interior of the fragment.

The Illumina sequences were taken from Illumina to ensure compatibility with the standard sequencing primer mix, but these sequences can be made longer or shorter or replaced entirely if corresponding custom sequencing primers are used. In this Example, 16-base random barcodes were used, but any length is adaptable for use. Additionally, the sequences can be less than completely degenerate (e.g., allowing only 1, 2, or 3 nucleotides at some or all positions). In the sequences used in this Example, there was a 2-base constant region outside the barcodes. However, this region of bases can be modified, i.e., made shorter or longer, or omitted altogether.

Moreover, two separate protocols were developed for barcode pairing, a two-tube protocol and a one-tube protocol. The one-tube protocol has the advantage of sample preparation occurring entirely in a single tube. A mixture of two or more barcode-containing adapters is ligated to the dT-tailed target fragments (e.g., a mixture of oligo 1 and oligo 2 as shown in Table 1). The adapters differ in their sequencing primer region. Sequences were derived from the Illumina Universal and Index primer sequences, respectively. As a result, approximately half of the target fragments will have different sequencing regions in the adapters that ligate to the two ends. Following PCR, some fraction of the full-length copies will avoid fragmentation, and circularization will bring the two barcodes together. Downstream limited-cycle PCR (lcPCR) will fail to amplify molecules that have the same adapter at each end because the identical sequencing regions outside the barcode regions will form a tight hairpin upon becoming single stranded. However, in molecules with different adapters at the ends, no hairpin will form, and addition of a primer complementary to the second sequencing region enables amplification of the paired barcodes. In the computational pipeline, paired-barcode reads are identified, trimmed of adapter sequences, and parsed to extract the barcode pairs.

The two-tube protocol adds the complexity of splitting the library preparation into two tubes for the last third of the protocol, one tube to generate barcoded target reads and a second solely to generate paired barcode reads. The advantage is improved control of the fraction of the eventual short reads of each type. In this protocol, only one adapter sequence is used, so all target molecules ligate the same adapter at both ends. As a result, all molecules derived from circularized full-length amplicons will form a tight hairpin during lcPCR, and no paired-barcode reads will be present in the main sequencing sample. Following attachment to streptavidin-coated beads and prior to ligation of asymmetric adapters, a fraction (~15%) of the beads are moved to a second tube. SapI digestion cuts a site in the sequencing region (taken from the Illumina Multiplexing Sample Prep Oligo Only Kit), leaving sticky ends. Y-shaped adapters are ligated to the sticky ends to provide PCR annealing regions, and subsequent lcPCR adds the requisite sequencing adapter regions and a multiplexing index that allows barcode-pairing reads to be identified during analysis.

Two-tube barcode pairing: Bead-bound DNA was digested with 10 units of SapI in 1× CutSmart buffer in a 20 µL total volume for 1 h at 37° C. The beads were washed three times with 200 µL of 1×B&W buffer and twice with 200 µL of buffer EB. A 15 µM equimolar mixture of two oligonucleotides (oligos 12 and 13, as set out in Table 1 below) in 1×T4 DNA ligase buffer was incubated at 95° C. for 2 minutes and allowed to cool to room temperature over 30 minutes. The beads were resuspended in a solution comprising 5 µL of NEB Blunt/TA ligase master mix, 0.5 µL of 15 µM adapter oligo solution, and 4 µL of water. The mixture was incubated for 15 minutes at 4° C. and 15 minutes at 20° C. The beads were washed twice with 200 µL of 1×B&W buffer and twice with 200 µL of buffer EB. For amplification by limited-cycle PCR, the beads were resuspended in a 50 µL PCR solution comprising 36 µL of water, 10 µL of 5× Phusion HF DNA polymerase buffer, 1.25 µL of each of 10 µM solutions of two primers (oligos 11 and 14, as set out in Table 1 below, with oligo 14 (as shown in Table 1) selected to have a different multiplexing index than oligo 10 (as shown in Table 1) used above), and 0.02 units/µL Phusion DNA polymerase (Thermo Fisher Scientific). The following thermocycling program was used: 98° C. for 30 seconds, followed by 18 cycles of 98° C. for 10 seconds, 60° C. for 30 seconds, and 72° C. for 30 seconds, and a final hold at 72° C. for 5 minutes. The supernatant was retained and the beads discarded. DNA was purified with 1.8 volumes of Ampure XP beads and eluted in 10 µL buffer EB. The expected product size of ~170 bp was confirmed by agarose gel electrophoresis and Agilent bioanalyzer. Cluster-forming DNA was quantified by qPCR. The DNA fragments were mixed with the main library so as to comprise 1-5% of the total molecules, and sequenced on an Illumina MiSeq, NextSeq, or HiSeq with standard Illumina primer mixtures.

Single-tube barcode pairing: Oligos 1 and 2 (as shown in Table 1) were mixed, extended with oligo 6 (as shown in Table 1), and ligated to dT-tailed target fragments as above. The library preparation protocol was carried out as above, except that no extra barcode-pairing was completed. Limited-cycle PCR was performed with 1.25 µL of a 10 micromolar solution oligo 15, as set out in Table 1 below, in addition to oligos 10 and 11 as shown in Table 1.

Complexity determination: The protocol includes quantification of doubly barcoded fragments prior to PCR. Doubly barcoded fragment concentration was estimated in three ways: quantitative PCR with a quenched fluorescent probe (oligo 19, as set out in Table 1 below), dilution series endpoint PCR, and quantification by next-generation sequencing. For the latter, barcoded molecules were purified and serially diluted. Four dilutions were amplified with oligo 6 and four versions of oligo 16, as set out in Table 1 below, containing different multiplexing index sequences. The resulting products were mixed and sequenced with 50-bp single-end reads on an Illumina MiSeq. Reads were demultiplexed and unique barcodes at each dilution were counted. When combined with the multiplexed library preparation strategy, which enables further demultiplexing on the basis of an index in the forward read, many samples can be quantified in a single MiSeq run.

TABLE 1

Oligonucleotide sequences

| OLIGO NO. | Oligonucleotide Sequence |
|---|---|
| 1 | 5'-/5Phos/NNN GTTCAGAGTT CTACAGTCCGACGATCNNNNNNNN NNNNNNNN CCAGGAATAGTTATG TGCATTAATGAATGG CCGC-3' (SEQ ID NO: 15) |
| 2 | 5'-/5Phos/NNN CCTACACGAC GCTCTTCCGATCTNNNNNNNNNN NNNNN ACAGGAATAGTTATGTGC ATTAATGAATGG CCGC-3' (SEQ ID NO: 16) |
| 3 | 5'-/5Phos/NNN CCTACACGAC GCTCTTCCGATCTNNNNNNNNNN NNNNN ACAATTCCTATCGTTCAC GTCGTGTCGCCATTTAGTGTCCAG TCTGA-3 (SEQ ID NO: 17) |
| 4 | 5'-/5Phos/NNN CCTACACGAC GCTCTTCCGATCTNNNNNNNNNN NNNNN CCAGGAATAGTTATGTGC ATTAATGAATGG CGCC-3' (SEQ ID NO: 18) |
| 5 | 5'-CCATTCAT/ideoxyU/AATG CACA/ideoxyU/AACTATTCC/ 3deoxyU/G*G-31 (SEQ ID NO: 19) |
| 6 | 5'-CCATTCAT/ideoxyU/AATG CACA/ideoxyU/AACTATTCC/ ideoxyU/G-3' (SEQ ID NO: 20) |
| 7 | 5'-ACACGACG/ideoxyU/GAAC GA/ideoxyU/AGGAAT/ ideoxyU/G*T-3' (SEQ ID NO: 21) |
| 8 | 5'-CCGAGAATTCCA*T-3' (SEQ ID NO: 22) |
| 9 | 5'-/5Phos/TGGAATTCTCGG G TGCCAAGG-3' (SEQ ID NO: 23) |
| 10 | 5'-CAAGCAGAAGACGGCATACGA (SEQ ID NO: 24) (Index) GTGACTGGAGTT CCTTGGCACCCGAGAATTCCA-3' (SEQ ID NO: 25) |

TABLE 1-continued

Oligonucleotide sequences

| OLIGO NO. | Oligonucleotide Sequence |
|---|---|
| 11 | 5'-AATGATACGGCGACCACCGAG ATCTACACTCTTTCCCTACACGAC GCTCTTCCGATC*T-3' (SEQ ID NO: 26) |
| 12 | 5'-ACACTCTTTCCCTACACGAC GCTCTTCC-3' (SEQ ID NO: 27) |
| 13 | 5'-/5Phos/A*TC GGAAGAGC ACACGTCT (SEQ ID NO: 28) |
| 14 | 5'-CAAGCAGAAGACGGCATACGA (SEQ ID NO: 24) (Index) GTGACTGGAGTTC AGACGTGTGCTCTTCCGATC* T-3' (SEQ ID NO: 29) |
| 15 | 5'-AATGATACGGCGACCACCGAG ATCTACACGTTCAGAGTTCTACAG TCCGA-3' (SEQ ID NO: 30) |
| 16 | 5'-CAAGCAGAAGACGGCATACGA GAT (SEQ ID NO: 24) (Index) GTGACTGGAGTT C AGACGTGTGCTCTTCCGATCCC ATTCATTAATGCACATAACTATTC C-3' (SEQ ID NO: 31) |
| 17 | 5'-CCATTCATTAATGCACATAAC TATTCCTGGNNNNNNNNNNNNNNN NGATCGTCGGACTGTAGAACTCTG AAC T$_{30}$VN-3' (SEQ ID NO: 32) |
| 18 | 5'-GCGGCCATTCATTAATGCACA TAACTATTCCTGT NNNNNNNNNN NNNNNNAGATCGGAAGAGCGTCGT GTAGG TrGrG+G-3' (SEQ ID NO: 33) |
| 19 | 5'-/56-FAM/CCT ACA CGA/ ZEN/CGC TCT TCC GAT CT/ 3IABkFQ/-3' (SEQ ID NO: 34) |
| 20 | 5'-NNN CCTACACGACGCTCTTC CGATCTNNNNNNNNNNNNNNNNNN (SEQ ID NO: 10) (Index) CAGGAATAGTTATGTG CATTAATGAATGG CGCC-3' (SEQ ID NO: 35) |

Key:
/5Phos/ = 5' phosphate group
/ideoxyU/ = internal deoxyuracil base
/3deoxyU/ = 3' deoxyuracil base
* = phosphorothioate linkage
rG = riboG
+G = locked nucleic acid G
N = mixture of A, T, G, and C
V = mixture of A, G, and C
T$_{30}$ = 30 consecutive Ts
lcPCR = limited-cycle PCR
Index = 6-base Illumina TruSeq Small RNA multiplexing index sequence
/56-FAM/ = probe fluorophore
/ZEN/ = probe quencher
/3IABkFQ/ = probe quencher Example 2

Testing Barcode Fidelity

Example 2 illustrates experiments carried out to test barcode fidelity. In general, a given barcode should be associated with a single target molecule, i.e., barcode fidelity. With barcode fidelity, every read tagged with that barcode should be derived from that single target molecule and should contain nucleotide sequence from that single target molecule alone.

Chimera formation during library preparation is problematic to barcode fidelity when sequencing a mixed population of target molecules. Once formed, chimeras are difficult to identify and filter out, and can confound assembly or lead to reconstruction of spurious sequences. Fortunately, the high coverage to which each target molecule is sequenced renders the method tolerant to a moderate level of chimera formation, in the same way that it ameliorates the effect of NGS error rates. Assuming 20-fold coverage at a chimera formation rate of 10%, half of the aligned calls at a given locus are erroneous only 0.005% of the time.

To test barcode fidelity of the method with homologous targets, a mixture of three linearized plasmids, each about 3 kb in length with homologous but distinct inserts, were sequenced. Each of the DNA plasmids, containing different mutants of the outer membrane protein A (OmpA) gene of *E. coli*, were purified from *E. coli*, linearized by restriction digestion, and mixed at known ratios. The resulting sample contained molecules of three known sequences, each at a different concentration. The target sequences were highly homologous and, thus, susceptible to recombination during PCR.

Following library preparation, sequencing, and barcode-mediated read sorting, the reads associated with each barcode were searched for short sequences unique to each target. The experiments showed that in the majority of cases, the contaminating reads were too few to confound analysis (see FIG. 2). About 80% of barcodes were confidently assigned to one target.

Example 3

Sequencing *Escherichia coli* BL21

Genomic DNA was isolated from the model organism *Escherichia coli* BL21 using a MasterPure™ DNA Purification Kit (Epicentre, Madison, WI) and sheared into fragments of an average length of about 3.5 kb using a Hydro-Shear DNA Shearing System (Digilab, Marlborough, MA). The fragment pool was converted to a sequencing-ready library following the protocol described herein and sequenced on a MiSeq sequencing instrument (Illumina, Inc., San Diego, CA) with a 250 bp paired-end read reagent kit. De-multiplexed reads were processed using a custom computational pipeline, i.e., computer programs designed to process the sequencing data and assemble the synthetic long reads. Groups of reads sharing barcode sequences were assembled into long contiguous sequences or "contigs," using the Velvet assembler, i.e., an algorithm package designed to assemble contigs from sequence information.

743,538 paired-end read pairs were trimmed to remove barcodes, spurious sequences, adapter sequences, and regions of low quality. The read pairs were sorted into barcode-defined groups. Barcode-defined groups were assembled with Velvet into 644 contigs, wherein the contigs had lengths greater than 1,000 bp. The longest contig was 4,423 bp, and the end of the distribution is in concordance with the 3.5 kb average length of the sheared genomic fragments, indicating that complete target molecule sequences were reconstructed from some of the barcode groups using Velvet.

A histogram of barcode frequencies in the sequencing results revealed the expected bimodal distribution. There is a bimodal distribution because there are two types of barcodes: true barcodes (seen many times each) and false barcodes caused by sequencing errors (seen only a few times each). A peak at low numbers of times seen corresponds to spurious barcodes resulting from sequencing errors; these reads were discarded with no significant loss in efficiency. A second peak, centered near 500 times seen per barcode, corresponded to the true barcodes. This peak was much broader than the ideal peak that would result from random selection from an equal population of all barcodes, implying that PCR amplification is biased, over-amplifying some targets at the expense of others. This bias could be magnified by other parts of the protocol.

Bias, in some aspects, can be reduced by modifications to the protocol. For example, in some aspects, bias is reduced by adding a linear amplification phase prior to exponential PCR, or by optimizing PCR conditions (e.g., primer sequences, extension times, annealing temperatures, etc). Still, given the low and rapidly declining cost of sequencing, the current levels of bias do not result in prohibitive inefficiency.

The relationship between the number of reads associated with a barcode and the longest contig assembled from those reads indicated that additional reads aid assembly (as expected) up to about 1000 reads. However, not only do barcodes that are seen more than 1000 times gain no extra advantage, the length of their longest contigs drops off. In some aspects, this may be a result of extra sequencing errors that confound assembly accumulating in excess reads, or indicate that the most frequently seen barcodes derive from spurious sequences.

The complexity bottleneck (a restriction on the number of barcoded molecules) imposed upon the mixed DNA population by dilution prior to PCR can be chosen for each experiment as a function of the length of the target molecules and the number of sequencing reads available. For example, in this experiment, the true complexity bottleneck was estimated to have been on the order of 1000 (about 700,000 reads divided by ~500 reads per barcode). Thus, the complexity (number of barcoded molecules) is bottlenecked (restricted) prior to PCR to optimize sequence assembly. If too many molecules are amplified in PCR, the sequencing reads are spread out among them to the point that full-length sequences cannot be assembled. If too few, then fewer than an optimal number of sequences are assembled. The choice of complexity depends on the number and length of reads to be generated, the length of the target molecules, and whether barcode pairing is used. In various aspects, determining the number of barcoded molecules in a sample is done by qPCR, dilution-series PCR, digital PCR, specific degradation of molecules lacking two adapters followed by quantification, or sequencing.

A BLAST search of the assembled contigs against known genomes confirmed that the majority of the contigs aligned to the *E. coli* genome with high accuracy. Contigs of length greater than 250 bp were submitted to the query. The contigs that aligned with the reference genome matched with 99.95% agreement, for an error rate of 0.05%. It is notable that this 0.05% error rate represents a ceiling on the error rate of the method, because the sequenced strain may have accumulated mutations that differentiate it from the reference, and because there is potential to optimize the assembly algorithm for greater accuracy.

In every barcode pool alignment that was examined, about 80% of the reads aligned within the same 3-4 kb region. The other 20% aligned to other areas of the genome in a seemingly random manner, likely as a result of intermolecular circularization during library preparation. This fraction is reducible through optimization of the circularization conditions, but this randomly scattered minority of fragments does not typically confound assembly or other applications of the method.

Example 4

Sequencing *Geoglobus ahangari*

Genomic DNA was isolated from the archaea *Geoglobus ahangari* using the Masterpure™ DNA Purification Kit (Epicentre) and sheared into fragments of an average length of 3.5 kb using a HydroShear DNA Shearing System (Digilab). The fragment pool was converted to a sequencing-ready library according to the protocol provided above and sequenced on a MiSeq instrument (Illumina) with a 250 bp paired-end read reagent kit. De-multiplexed reads were processed using a custom computational pipeline, as described herein. Groups of reads sharing barcode sequences were assembled into contigs using the Velvet assembler. 2.3 million paired-end read pairs were trimmed to remove barcodes, spurious sequences, adapter sequences, and regions of low quality, and sorted into barcode-defined groups. Using the Velvet assembler, the resultant barcode groups were assembled into 1497 contigs of lengths greater than 1,000 bp. The longest contig was 4,507 bp, and the end of the distribution is in concordance with the 3.5 kb average length of the sheared genomic fragments, indicating that Velvet was able to reconstruct complete target molecule sequences from some of the barcode groups.

*Geoglobus ahangari* contigs were used to improve an existing, incomplete draft genome for this organism. The draft genome contained 50 disconnected contigs. Long reads from the method disclosed herein allowed the 50 disconnected contigs to be collapsed into 30 contigs, containing no unresolved ("N") bases. This experiment demonstrated that the long contigs derived from methods of the disclosure dramatically improved the draft genome of *Geoglobus ahangari* by resolving ambiguities in short-read assemblies.

The bimodal distribution of barcode frequencies was less pronounced in the *Geoglobus* data, indicating potentially more severe PCR bias compared to the *E. coli* data. The true complexity bottleneck is estimated to have been on the order of about 4000 (about 2.3 million reads divided by ~500 reads per barcode).

Example 5

Sequencing *Tuberosum solanum*

Genomic DNA was isolated from a doubled monoploid variety of an important food crop, i.e., *Tuberosum solanum* (the potato), and sheared into fragments of an average length of 3.5 kb using a HydroShear DNA Shearing System (Digilab). The fragment pool was converted to a sequencing-ready library according to the protocol set out above and sequenced on a MiSeq instrument (Illumina) with a 250 bp paired-end read reagent kit. De-multiplexed reads were processed using a custom computational pipeline, as described herein. Groups of reads sharing barcode sequences were assembled using the Velvet assembler.

10.2 million paired-end read pairs were trimmed to remove barcodes, spurious sequences, adapter sequences, and regions of low quality, and sorted into barcode-defined groups. Using the Velvet assembler, the resultant barcode groups were assembled into 1,508 contigs of length greater than 1,000 bp. The longest contig was 5,249 bp, and the end of the distribution was in concordance with the 3.5 kb average length of the sheared genomic fragments, indicating that Velvet was able to reconstruct complete target molecule sequences from some of the barcode groups.

The sequencing results revealed the expected bimodal distribution. The true complexity bottleneck was estimated to have been on the order of about 4000 (about 10.2 million reads divided by ~3000 reads per barcode).

Assembled reads were analyzed further using bioinformatics. A blind test was carried out because the experimenters did not have access to the potato reference genome during contig assembly. The potato contigs were aligned to an existing draft genome maintained by the Potato Genome Consortium. Approximately 70-90% of the contigs aligned to the reference genome, depending on the stringency of the alignment parameters (minimum 98% agreement). The high sequence agreement between the long contigs and the draft genome highlighted the accuracy of contigs generated by methods of the disclosure, in contrast to previously known long-read technology. A Basic Local Alignment Search Tool (BLAST, NIH) search returned hits to potato, as well as related organisms, including tomato and nightshade. Potato is a tetraploid organism. Long reads, such as those obtained by methods of the disclosure, are instrumental to resolving the haplotype of each chromosome.

Example 6

Sequencing *Escherichia coli* Strain MG1655

Sequencing libraries were prepared from genomic DNA isolated from *E. coli* strain MG1655. Genomic DNA was sheared and size-selected to a range of about 5-10 kb. About 8 million 150 bp paired-end read pairs were filtered and trimmed to remove barcodes, adapter sequences, and regions of low quality and then sorted into barcode-delineated groups, as described herein. Barcode pairing resolved 1,186 distinct barcode pairs, whose read groups were merged prior to assembly. Independent assembly of each group with the SPAdes assembler (Bankevich et al., *J. Computational Biology* 19(5): 455-77, 2012) yielded 2,826 contigs of length greater than 1,000 bp.

To determine the fidelity of assembly, the largest contig assembled from each barcode-defined group was aligned to the MG1655 reference genome (Hayashi et al., Mol. Syst. Biol. 2:0007, 2006). Alignment of grouped reads to the reference genome showed a non-uniform distribution of coverage across the fragment length, with coverage dropping off along the length of the target sequence. Barcode pairing reduced the impact of the coverage drop because coverage from one barcode is high in the region where coverage from its pair is low. Coverage is the number of short reads that align to a given location on the long target sequence. Coverage drops from one end of the target to the other, presumably because circularization is less efficient for longer molecules. Coverage from reads with the partner barcode is a mirror image: high on the other end, and dropping toward the first end. The sum of the two profiles is therefore relatively smoothed. This experiment showed that assembly of longer molecules requires high average read depths. Merging the paired read groups resulted in a smoother distribution of coverage (see FIG. 1B.)

The length distribution of the assembled contigs had an N50 (half of the total assembled bases are in contigs greater than the N50) of 6 kb and a maximum assembly length of 11.6 kb (see FIG. 1C). The error rate when contigs were aligned back to the reference MG1655 genome was only about 0.1%. Thus, the experiment showed that the method described herein was used to assemble contigs with an N50 of 6 kb with about 99.9% accuracy.

Example 7

Sequencing *Gelsemium sempervirens*

Sequencing libraries were prepared from genomic DNA isolated from Carolina jasmine (*Gelsemium sempervirens*), a plant with a complex and previously unsequenced genome. 149,447 contigs longer than 1 kb, with an N50 of 4 kb, were assembled. The assembled long reads aligned with high stringency to a draft assembly of the *Gelsemium sempervirens* genome, and increased the maximum scaffold length from about 197,779 bp to about 365,589 bp. Thus, the experiment showed that the method described herein was used to assemble contigs with an N50 of 4 kb (see FIG. 1C), and was useful in assembling a large portion of a previously unsequenced genome.

Example 8

Library Preparation for Synthetic Long Read Assembly from mRNA Samples

Full-length reverse transcripts were prepared with primers, where the primers included oligo 17 and oligo 18, as set out in Table 1 below, respectively. Barcoded full-length reverse transcripts were then processed and sequenced, starting from library quantification. The barcoded cDNA product was amplified, broken, circularized, and prepared for sequencing. From mRNA isolated from HCT116 and HepG2 cells, we assembled 28,689 and 16,929 synthetic reads, respectively, of lengths between 0.5 and 4.6 kb. Synthetic reads spanned multiple splice junctions, with a median of 2.0 spanned junctions per synthetic read for both samples and a maximum of 35 spanned junctions. Examination of the synthetic reads revealed examples of differential splicing between the HCT116 and HepG2 cell lines, as well as a novel transcript in the HCT116 cell line.

Example 9

Multiplexed Sample Preparation

Two *E. coli* strains were isolated from each of twelve recombination treatment populations (See e.g., Souza et al. Journal of Evolutionary Biology 10:743-769, 1997). Genomic DNA was isolated from each of the twenty-four strains, sheared, end-repaired, and dT-tailed as described above in separate tubes. Twenty-four barcode adapters (oligo 20, as set out in Table 1 below), identical except for distinct 6-bp multiplexing index regions adjacent to the barcode sequence, were prepared and ligated to the genomic fragments as described above. Adapter-ligated DNA was PCR amplified as above. Purified PCR products were quantified and equal amounts were combined into a single mixture. This mixture was prepared for sequencing following the other parts of the above protocol. Sequencing reads were demultiplexed by project according to standard 6-bp index read, then further demultiplexed by strain according to the barcode-adjacent multiplexing index identified in the forward read, sorted by barcode, and assembled in parallel. The summed lengths of the synthetic reads longer than 1 kb exceeded twofold genome coverage for sixteen out of the twenty-four strains, with a median genome coverage of 2.3 fold and median N50 of 4.1 kb.

Example 10

Fragment Generation Based on Extension of Random Primers

In some embodiments, fragments with randomly determined ends are created by annealing primers of random or partially random sequences. Each such primer anneals to a complimentary region of the target molecule and is extended by a polymerase. In some cases, the polymerase is capable of strand displacement. In some instances, Bst polymerase is used. In some embodiments, phi29 polymerase is used. In some cases, Vent polymerase is used. In some embodiments, this operation is preceded by linear or exponential amplification of the targets. In some embodiments, the targets are not amplified beforehand. In some cases, a mixture including template molecules and random primers is melted at 95° C. and quenched to 0° C. to allow primer annealing. Bst polymerase can be added and the mixture can be slowly warmed to 65° C. by ramping or stepping. In some cases, primers complementary to the adapter ends of the target are present or are added, and prime the single-stranded DNA synthesized following random priming at its 3' end. Extension by a DNA polymerase generates double-stranded DNA fragments with the known adapter end sequence at one end and a random sequence from the interior of the target molecule at the other end. In some embodiments, multiple rounds of this linear amplification and fragment generation are performed. In some embodiments, additional rounds are performed by heating the mixture to e.g. 95° C. to melt the double-stranded DNA duplexes, cooling to promote random primer annealing, and if necessary adding additional DNA polymerase. In some embodiments, the target molecule adapters contain one or more biotinylated nucleotides that allow them to specifically bind to streptavidin-coated beads, so that the newly generated fragments can be easily separated from the original targets between rounds of amplification. In some embodiments, the random primers contain defined sequences at their 5' end and random sequences at their 3' end, so that the resulting ssDNA or dsDNA contains known sequences at both ends. In some embodiments, the known sequences are the same. In some embodiments, they are different. In some cases, fragments are subsequently amplified by PCR using one or more primers complementary to the known end sequences. In some embodiments, DNA fragments created by linear or exponential amplification contain known end sequences that are reverse complements of each other and contain one or more deoxyuracil bases in the 5' ends. A combination of uracil-DNA glycosylase (UDG) and exonuclease VIII can then be used to remove the 5' ends, leaving long single-stranded complimentary sequences that can anneal to increase the efficiency of intramolecular circularization. In some embodiments, treatment with UDG and exonuclease VIII is preceded by treatment with Klenow fragment or a similar enzyme to remove nontemplated deoxyadenosine bases added to the 3' ends during extension. In some cases, the known end sequences contain sequences that can be recognized by recombinase enzymes that circularize the fragment by recombination. In some embodiments, circularization is by blunt-end ligation.

In some cases, circularized fragments are fragmented by mechanical or enzymatic (e.g. fragmentase, transposons) methods and prepared for sequencing by ligating adapters and performing lcPCR as described herein.

In some embodiments, circularized fragments are amplified by rolling-circle amplification (RCA) or hyperbranching rolling-circle amplification (HRCA). In some cases, RCA or HRCA is primed with random primers or partially random primers. In some embodiments, amplification is primed by one or more primers of defined sequence. In some instances, amplification is performed in the presence of up to 100% dUTP in place of dTTP, to allow the product be specifically degraded later. In some embodiments, RCA or HCRA is followed by mechanical or enzymatic fragmentation, adapter ligation, and PCR as described herein. In some embodiments, RCA or HRCA is followed directly by PCR or limited-cycle PCR. In some embodiments, PCR is primed with one primer complementary to the defined sequence at the 5' end of the partially random primer used for RCA or HRCA, and a second primer complementary to a sequence in the barcode adapter proximal to the barcode sequence. In some embodiments, the PCR primers are complementary to these sequences, but additionally contain 5' extensions that add further sequences necessary for sequencing. In some cases, RCA or HCRA products containing deoxyuracil are subsequently degraded to enrich for PCR products.

With reference to FIG. 8A, a mixture of target DNA molecules, with barcode adapters attached to the ends according to methods described herein, is prepared with the desired complexity (number of distinct molecules). The barcode adapters contain an end region of defined sequence (X), a degenerate barcode region (B) that is different for every target molecule but defined for a given individual molecule, and a defined region ($I_1$) complementary to some or all of one of the two eventual sequencing primers, such as a standard sequencing primer (e.g., Illumina) or a custom primer. Optionally, the molecules are amplified by linear or exponential methods to create $10^1$-$10^5$ copies of each uniquely barcoded molecule. The target molecules are melted into single-stranded DNA by heating or exposure to alkaline or other denaturing conditions. One or more random or partially random primers are then annealed along the length the target molecules by rapid quenching to 0-4° C. The primers depicted here are partially random, with a random 3' region and a defined 5' region (sequence Y).

Continuing with FIG. 8A and FIG. 8B, a strand-displacing DNA polymerase, such as Bst DNA polymerase, is added to the primer-annealed target DNA mixture. The temperature is ramped or stepped up to 65° C., and the polymerase extends each of the random 3' primer ends annealed along the length of the target molecule, displacing extended molecules in front of it as it goes and releasing them into solution. One end of the newly synthesized single-stranded DNA molecules is defined by the partially random primer and contains the Y sequence followed by a sequence complementary to the region of the target molecule to which a specific primer from the degenerate mixture annealed. The other end is defined by a sequence complementary to the end sequence of the target molecule, which comprises $I_1$-B-X. A primer with a sequence complementary to X is present in the mixture, and is designed with an annealing temperature greater than 65° C., allowing it to anneal to the ends of the newly synthesized displaced molecules and prime synthesis of the second strand, creating double-stranded DNA. The result is a collection of target fragments, with no mechanical or enzymatic shearing needed. If desired, multiple cycles of melting, annealing, and strand-displacement amplification can be performed to increase the yield of DNA. If desired, deoxyadenosine overhangs added by the Bst polymerase in a template-independent fashion can be removed by incubation with e.g. Klenow DNA polymerase to create blunt-ended dsDNA.

Continuing with FIG. 8A and FIG. 8B, fragments synthesized can be circularized by blunt-end ligation. Alternatively, to improve circularization efficiency of long fragments, sticky-end ligation can be performed, as shown here. If sequences X and Y in the partially random primers and the second-strand primers are synthesized so that they contain deoxyuracil bases, the USER enzyme mix (UDG and endonuclease VIII) can excise the 5' ends of each strand of the dsDNA to leave sticky ends of programmable length. If X and Y are reverse-complements, the sticky ends will be complementary, and will anneal to one another to promote ligation.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for processing a polynucleotide comprising a target nucleotide sequence, said method comprising:
   (a) attaching a first adapter comprising an outer polymerase chain reaction (PCR) primer region or a nucleic acid amplification region, an inner sequencing primer region, and a central barcode region to a 5' end and a 3' end of a linear nucleic acid molecule from among a plurality of linear nucleic acid molecules derived from the polynucleotide, to form barcode-tagged molecules;
   (b) replicating the barcode-tagged molecules to obtain a library of barcode-tagged molecules;
   c) fragmenting the barcode-tagged molecules, thereby generating first linear barcode-tagged fragments comprising the central barcode region of the first adapter at one end and a region of unknown sequence from an interior portion of the target nucleotide sequence at the other end;
   (d) circularizing the first linear barcode-tagged fragments comprising the central barcode region of the first adapter at one end and the region of unknown sequence from the interior portion of the target nucleotide sequence at the other end, thereby yielding circularized barcode-tagged fragments comprising the central barcode region in proximity with the region of unknown sequence;
   (e) fragmenting the circularized barcode-tagged fragments into second linear barcode-tagged fragments; and
   (f) attaching a second adapter to each end of the second linear barcode-tagged fragments to form double adapter-ligated barcode-tagged nucleic acid fragments.

2. The method of claim 1, further comprising fragmenting the polynucleotide into the plurality of linear nucleic acid molecules prior to attaching the first adapter.

3. The method of claim 1, wherein the first adapter attached at the 5' end of the linear nucleic acid molecule comprises a different barcode than the first adapter attached at the 3' end of the linear nucleic acid molecule.

4. The method of claim 1, wherein the first adapter attached at the 5' end of the linear nucleic acid molecule and the first adapter attached at the 3' end of the linear nucleic acid molecule comprise the same barcode.

5. The method of claim 1, wherein the replicating the barcode-tagged molecules is carried out by PCR.

6. The method of claim 1, wherein the replicating the barcode-tagged molecules is carried out using a primer complementary to the outer PCR primer region.

7. The method of claim 1, further comprising removing the outer PCR primer region from the barcode-tagged molecules.

8. The method of claim 7, wherein the removing the outer PCR primer region is carried out before circularizing the first linear barcode-tagged fragments.

9. The method of claim 1, wherein the fragmenting the barcode-tagged molecules of (c) or the circularized barcode-tagged fragments of (e) is carried out by an enzyme.

10. The method of claim 1, wherein the fragmenting the barcode-tagged molecules of (c) or the circularized barcode-tagged fragments of (e) is carried out at random locations on nucleic acid sequences of the barcode-tagged molecules or at random locations on nucleic acid sequences of the circularized barcode-tagged fragments, respectively.

11. The method of claim 1, further comprising sequencing the double adapter-ligated barcode-tagged nucleic acid fragments, or derivatives thereof, beginning with the central barcode region followed by the region of unknown sequence.

12. The method of claim 11, wherein the sequencing is paired-end sequencing.

13. The method of claim 1, further comprising selecting the plurality of linear nucleic acid molecules on the basis of size prior to attaching the first adapter.

14. The method of claim 1, further comprising sequencing the double adapter-ligated barcode-tagged nucleic acid fragments, or derivatives thereof, to yield nucleic acid sequence information for the polynucleotide, wherein the polynucleotide comprises a length of at least about 500 bases.

15. The method of claim 14, wherein the sequencing is paired-end sequencing.

16. The method of claim 1, further comprising sequencing the double adapter-ligated barcode-tagged nucleic acid fragments, or derivatives thereof, to yield nucleic acid sequence information for the polynucleotide, wherein the nucleic acid sequence information comprises greater than about 95% fidelity to the target nucleotide sequence of the polynucleotide.

17. The method of claim 16, wherein the sequencing is paired-end sequencing.

18. The method of claim 1, wherein the polynucleotide comprising the target nucleotide sequence originates from genomic deoxyribonucleic acid (DNA).

19. The method of claim 1, wherein (a)-(f) are carried out in one container.

20. The method of claim 1, further comprising (g) replicating all or part of the double adapter-ligated barcode-tagged nucleic acid fragments.

21. The method of claim 20, further comprising:
(h) sequencing the double adapter-ligated barcode-tagged nucleic acid fragments, or derivatives thereof, thereby generating a series of sequenced nucleic acid fragment reads;
(i) sorting the series of sequenced nucleic acid fragment reads into independent groups, thereby generating groups of reads; and
(j) assembling each of the groups of reads into a nucleic acid sequence comprising the target nucleotide sequence.

22. The method of claim 21, wherein (a)-(h) are carried out in one container.

23. The method of claim 21, wherein sorting the series of sequenced nucleic acid fragment reads into independent groups is based on shared barcodes between individual sequenced nucleic acid fragment reads of the series of sequenced nucleic acid fragment reads.

24. The method of claim 21, wherein assembling each of the groups of reads is carried out independent of all other groups of reads.

25. The method of claim 21, further comprising selecting the double adapter-ligated barcode-tagged nucleic acid fragments on the basis of size prior to the sequencing.

26. The method of claim 21, wherein the sequencing is paired-end sequencing.

27. The method of claim 1, wherein the first adapter further comprises a sample identifier sequence that identifies the barcode-tagged molecules, or derivatives thereof, with a sample comprising the polynucleotide.

28. The method of claim 1, further comprising, prior to (a), providing a first container comprising the plurality of linear nucleic acid molecules and a second container comprising other linear nucleic acid molecules derived from another polynucleotide, and (i) in the first container, generating the barcode-tagged molecules from the plurality of linear nucleic acid molecules, wherein each of the barcode-tagged molecules comprises a first common identifier sequence that identifies the barcode-tagged molecules in the first container comprising the plurality of linear nucleic acid molecules, and (ii) in the second container, generating other barcode-tagged molecules from the other linear nucleic acid molecules, wherein each of the other barcode-tagged molecules comprises a second common identifier sequence that identifies the other barcode-tagged molecules in the second container comprising the other linear nucleic acid molecules.

29. The method of claim 28, wherein (b) is performed with the barcode-tagged molecules from the first container and the second container in a pool.

30. The method of claim 28, wherein (c) is performed with a library of barcode-tagged molecules from the first container and a library of barcode-tagged molecules from the second container in a pool.

* * * * *